US008697085B2

(12) United States Patent
Dale

(10) Patent No.: US 8,697,085 B2
(45) Date of Patent: Apr. 15, 2014

(54) **GROUP A *STREPTOCOCCUS* MULTIVALENT VACCINE**

(75) Inventor: James B. Dale, Memphis, TN (US)

(73) Assignee: University of Tennessee Research Foundation, Knoxville, TN (US)

(*) Notice: Subject to any disclaimer, the term of this patent is extended or adjusted under 35 U.S.C. 154(b) by 0 days.

(21) Appl. No.: 13/525,020

(22) Filed: Jun. 15, 2012

(65) Prior Publication Data

US 2012/0321657 A1 Dec. 20, 2012

Related U.S. Application Data

(60) Provisional application No. 61/641,448, filed on May 2, 2012, provisional application No. 61/498,397, filed on Jun. 17, 2011.

(51) Int. Cl.
*A61K 39/09* (2006.01)
*C07K 14/315* (2006.01)

(52) U.S. Cl.
USPC .................. 424/192.1; 424/244.1; 424/252.3; 530/350

(58) Field of Classification Search
None
See application file for complete search history.

(56) References Cited

U.S. PATENT DOCUMENTS

| | | | |
|---|---|---|---|
| 4,284,537 | A | 8/1981 | Beachey |
| 4,454,121 | A | 6/1984 | Beachey |
| 4,521,334 | A | 6/1985 | Beachey |
| 4,597,967 | A | 7/1986 | Beachey |
| 4,705,684 | A | 11/1987 | Beachey |
| 4,919,930 | A | 4/1990 | Beachey et al. |
| 5,124,153 | A | 6/1992 | Beachey et al. |
| 6,063,386 | A | 5/2000 | Dale et al. |
| 6,419,932 | B1 | 7/2002 | Dale |
| 6,716,433 | B1 | 4/2004 | Dale |
| 7,063,850 | B1 | 6/2006 | Dale |
| 7,074,416 | B2 | 7/2006 | Dale |
| 7,160,547 | B2 | 1/2007 | Dale |
| 7,255,863 | B2 | 8/2007 | Dale |
| 7,270,827 | B2 | 9/2007 | Reddish et al. |
| 7,402,316 | B2 | 7/2008 | Dale |
| 7,407,664 | B2 | 8/2008 | Beall et al. |
| 7,811,585 | B2 | 10/2010 | Martin et al. |
| 7,883,710 | B2 | 2/2011 | Beall et al. |
| 2009/0035259 | A1 | 2/2009 | Dale |

FOREIGN PATENT DOCUMENTS

WO 00/37648 A1 6/2000

OTHER PUBLICATIONS

McNeil et al 2005 , Clinical Infectious diseases 41: 114-22.*
Luca-Harari et al 2009, J.Clin.Microbiol, 47(4) :1155.*
Ahmed et al., "Streptococcal protective antigens (Spa): a new family of type-specific proteins of group A streptococci," *European Journal of Clinical Microbiology & Infectious Diseases 29*(1):51-57, Jan. 2010.
Bronze et al., "Epitopes of streptococcal M proteins that evoke antibodies that cross-react with human brain," *Journal of Immunology 151*(5):2820-2828, Sep. 1, 1993.
Carapetis et al., "The global burden of group A streptococcal diseases," *The Lancet Infectious Diseases 5*(11):685-594, Nov. 2005.
Courtney et al., "Anti-phagocytic mechanisms of *Streptococcus pyogenes*: binding of fibrinogen to M-related protein," *Molecular Microbiology 59*(3):936-947, 2006.
Dale, "Current Status of Group A Streptococcal Vaccine Development," *Advances in Experimental Medicine and Biology 609*:53-63, 2008.
Dale, "Group A streptococcal vaccines," *Infectious Disease Clinics of North America 13*(1):227-243, Mar. 1999, 18 pages.
Dale et al., "Multiple, heart-cross-reactive epitopes of streptococcal M proteins," *Journal of Experimental Medicine 161*(1):113-122, Jan. 1, 1985.
Dale et al., "Multivalent Group A Streptococcal Vaccine Elicits Bactericidal Antibodies against Variant M Subtypes," *Clinical and Diagnostic Laboratory Immunology 12*(7):833-836, Jul. 2005.
Dale et al., "New 30-Valent M Protein-Based Vaccine Evokes Cross-Opsonic Antibodies Against Non-Vaccine Serotypes of Group A Streptococci," *Vaccine*. Oct. 26, 2011; 29(46):8175-8178. doi:10.1016/j.vaccine.2011.09.005., 9 pages.
Dale et al., "New protective antigen of group A streptococci," *Journal of Clinical Investigation 103*(9):1261-1268, May 1, 1999.
Dale et al., "Protective antigenic determinant of streptococcal M protein shared with sarcolemmal membrane protein of human heart," *Journal of Experimental Medicine 156*(4):1165-1176, Oct. 1, 1982.
Facklam et al., "*emm* Typing and Validation of Provisional M Types for Group A Streptococci," *Emerging Infectious Diseases 5*(2):247-253, Apr.-Jun. 1999.
Hu et al., "Immunogenicity of a 26-Valent Group A Streptococcal Vaccine," *Infection and Immunity 70*(4):2171-2177, Apr. 2002.
Husmann et al., "Expression of the Arp protein, a member of the M protein family, is not sufficient to inhibit phagocytosis of *Streptococcus pyogenes*," *Infection and Immunity 63*(1):345-348, Jan. 1995.
Johnsson et al., "Identification of the IgA-binding region in streptococcal protein Arp," *Journal of Immunology 153*(8):3557-3564, Oct. 15, 1994.
Kellermayer et al., "Release of Potassium, Lipids, and Proteins From Nonionic Detergent Treated Chicken Red Blood Cells," *Journal of Cellular Physiology 159*:197-204, 1994.
Kotloff et al., "Safety and Immunogenicity of a Recombinant Multivalent Group A Streptococcal Vaccine in Healthy Adults," (Reprinted) *Journal of the American Medical Association 292*(6):709-715, Aug. 11, 2004.
Luca-Harari et al., "Clinical and Microbiological Characteristics of Severe *Streptococcus pyogenes* Disease in Europe," *Journal of Clinical Microbiology 47*(4):1155-1165, Apr. 2009.

(Continued)

*Primary Examiner* — Padma V Baskar
(74) *Attorney, Agent, or Firm* — Seed IP Law Group PLLC

(57) ABSTRACT

Immunogenic compositions are provided herein that are useful for inducing an immune response specific against group A *streptococcus* (GAS). Immunogenic compositions provided herein are multivalent and comprise a plurality of immunogenic peptides or fusion polypeptides comprising the immunogenic peptides that induce an immune response against GAS. The immunogenic compositions provided herein induce an immune response against the GAS serotypes represented by an immunogenic peptide (derived from an M protein or Spa protein) comprised within the immunogenic composition and also induce an immune response against serotypes that are unrepresented by any immunogenic peptide included in the immunogenic composition. Methods for using the compositions for inducing an immune response against GAS and for treating or reducing the likelihood of occurrence of a GAS infection are also provided.

17 Claims, 12 Drawing Sheets

(56) References Cited

OTHER PUBLICATIONS

McLellan et al., "Spa Contributes to the Virulence of Type 18 Group A Streptococci," *Infection and Immunity 69*(5):2943-2949, May 2001.

McNeil et al., "Safety and Immunogenicity of 26-Valent Group A Streptococcus Vaccine in Healthy Adult Volunteers," *Clinical Infectious Diseases 41*:000-000, Oct. 15, 2005, 9 pages.

O'Loughlin et al., "The Epidemiology of Invasive Group A Streptococcal Infection and Potential Vaccine Implications: United States, 2000-2004," *Clinical Infectious Diseases 45*(7):853-862, Oct. 1, 2007.

Shulman et al., "Group A Streptococcal Pharyngitis Serotype Surveillance in North America, 2000-2002," *Clinical Infectious Diseases 39*(3):325-332, Aug. 1, 2004.

Shulman et al., "Seven-Year Surveillance of North American Pediatric Group A Streptococcal Pharyngitis Isolates", *Clinical Infectious Diseases 49*(1):78-84, Jul. 1, 2009.

Steer et al., "Group A streptococcal vaccines: facts versus fantasy," *Current Opinion in Infectious Diseases 22*(6):544-552, 2009.

Steer et al., "Global *emm* type distribution of group A streptococci: systematic review and implications for vaccine development," *The Lancet Infectious Diseases 9*(10):611-616, Oct. 2009.

* cited by examiner

Fusion Polypeptide 1

| M1 | M3.1 | M6.4 | M2 | M18 | M28 | M12 | SPA | M1 | 451 AA |
|---|---|---|---|---|---|---|---|---|---|
| 1-50 | 22-71 | (1-25)2 | (2-26)2 | 1-50 | 1-50 | 1-50 | 1-50 | 1-50 | |

Fusion Polypeptide 2

| M4 | M5.0 | M11 | M75 | M19 | M29.2 | M14.3 | M24 | M4 | 451 AA |
|---|---|---|---|---|---|---|---|---|---|
| 1-50 | (1-25)2 | 1-50 | 1-50 | (1-25)2 | 1-50 | 1-50 | 1-50 | 1-50 | |

Fusion Polypeptide 3

| M77 | M22 | M73 | M89 | M58 | M44 | M78 | M118 | M77 | 451 AA |
|---|---|---|---|---|---|---|---|---|---|
| 1-50 | 1-50 | 1-50 | 1-50 | 1-50 | 1-50 | 1-50 | 1-50 | 1-50 | |

Fusion Polypeptide 4

| M83.1 | M82 | M81 | M87 | M49.1 | M92 | M114 | M83.1 | 401 AA |
|---|---|---|---|---|---|---|---|---|
| 1-50 | 1-50 | 1-50 | 1-50 | 1-50 | 1-50 | 1-50 | 1-50 | |

Polynucleotide Encoding Fusion Polypeptide 1 (SEQ ID NO:17)

AGATCTCGAT CCCGCGAAAT TAATACGACT CACTATAGGG GAATTGTGAG CGGATAACAA
TTCCCCTCTA GAAATAATTT TGTTTAACTT TAAGAAGGAG ATATCATATG AACGGTGACG
GTAACCCGCG TGAAGTTATC GAAGACCTGG CTGCTAACAA CCCGGCTATC CAGAACATCC
GTCTGCGTCA CGAAAACAAA GACCTGAAAG CTCGTCTGGA AAACGCTATG GAAGTTGCTG
GTCGTGACTT CAAACGTGCT CTGCTGGACC AGGTTACCCA GCTGTACACC AAACACAACT
CCAACTACCA GCAGTACAAC GCTCAGGCTG GTCGTCTGGA CCTGCGTCAG AAAGCTGAAT
ACCTGAAAGG TCTGAACGAC TGGGCTGAAC GTCTGCTGCA GGAACTGAAC CGTGTTTTCC
CGCGTGGTAC CGTTGAAAAC CCGGACAAAG CTCGTGAACT GCTGAACAAA TACGACGTTG
AAAACCGTGT TTTCCCGCGT GGTACCGTTG AAAACCCGGA CAAAGCTCGT GAACTGCTGA
ACAAATACGA CGTTGAAAAC TCCAAAAACC CGGTTCCGGT TAAAAAAGAA GCTAAACTGT
CCGAAGCTGA ACTGCACGAC AAAATCAAAA ACCTGTCCAA AAACCCGGTT CCGGTTAAAA
AAGAAGCTAA ACTGTCCGAA GCTGAACTGC ACGACAAAAT CAAAAACCTG GCTCCGCTGA
CCCGTGCTAC CGCTGACAAC AAAGACGAAC TGATCAAACG TGCTAACGAC TACGAAATCC
AGAACCACCA GCTGACCGTT GAAAACAAAA AACTGAAAAC CGACAAAGAA CAGCTGACCA
AAGAAAACGA CGACCTGAAA GCTGAATCCC CGAAATCCAC CGAAACCTCC GCTAACGGTG
CTGACAAACT GGCTGACGCT TACAACACCC TGCTGACCGA ACACGAAAAA CTGCGTGACG
AATACTACAC CCTGATCGAC GCTAAAGAAG AAGAACCGCG TTACAAAGCT GACCACTCCG
ACCTGGTTGC TGAAAAACAG CGTCTGGAAG ACCTGGGTCA GAAATTCGAA CGTCTGAAAC
AGCGTTCCGA ACTGTACCTG CAGCAGTACT ACGACAACAA ATCCAACGGT TACAAAGGTG
ACTGGTACGT TCAGCAGCTG GACTCCGTTT CCGGTCTGGA AGTTGCTGAC CCGTCCGACT
CCAAAAAACT GATCGAACTG GGTCTGGCTA AATACCTGAA CGACAAACTG CCGTTCAAAA
CCAAAGAAGA CTCCGAAATC CTGTCCGAAC TGCGTGACGT TCTGAAAAAC AACGGTGACG
GTAACCCGCG TGAAGTTATC GAAGACCTGG CTGCTAACAA CCCGGCTATC CAGAACATCC
GTCTGCGTCA CGAAAACAAA GACCTGAAAG CTCGTCTGGA AAACGCTATG GAAGTTGCTG
GTCGTGACTT CAAACGTGCT CACCACCACC ACCACCACTA G 1481

*Fig. 2A*

Fusion Polypeptide 1 (MW: 52,782, pI: 6.48) (SEQ ID NO:9)

MNGDGNPREV IEDLAANNPA IQNIRLRHEN KDLKARLENA MEVAGRDFKR ALLDQVTQLY
TKHNSNYQQY NAQAGRLDLR QKAEYLKGLN DWAERLLQEL NRVFPRGTVE NPDKARELLN
KYDVENRVFP RGTVENPDKA RELLNKYDVE NSKNPVPVKK EAKLSEAELH DKIKNLSKNP
VPVKKEAKLS EAELHDKIKN LAPLTRATAD NKDELIKRAN DYEIQNHQLT VENKKLKTDK
EQLTKENDDL KAESPKSTET SANGADKLAD AYNTLLTEHE KLRDEYYTLI DAKEEEPRYK
ADHSDLVAEK QRLEDLGQKF ERLKQRSELY LQQYYDNKSN GYKGDWYVQQ LDSVSGLEVA
DPSDSKKLIE LGLAKYLNDK LPFKTKEDSE ILSELRDVLK NNGDGNPREV IEDLAANNPA
IQNIRLRHEN KDLKARLENA MEVAGRDFKR AHHHHHH 457

*Fig. 2B*

Polynucleotide Encoding Fusion Polypeptide 2 (SEQ ID NO:18)

AGATCTCGAT CCCGCGAAAT TAATACGACT CACTATAGGG GAATTGTGAG CGGATAACAA
TTCCCCTCTA GAAATAATTT TGTTTAACTT TAAGAAGGAG ATATACCATG GCTGAAATCA
AAAAACCGCA GGCTGACTCC GCTTGGAACT GGCCGAAAGA ATACAACGCT CTGCTGAAAG
AAAACGAAGA ACTGAAAGTT GAACGTGAAA AATACCTGTC CTACGCTGAC GACAAAGAAA
AAGACCCGCA GTACCGTGCT GCTGTTACCC GTGGTACCAT CAACGACCCG CAGCGTGCTA
AAGAAGCTCT GGACAAATAC GAACTGGAAA ACCACGCTGT TACCCGTGGT ACCATCAACG
ACCCGCAGCG TGCTAAAGAA GCTCTGGACA AATACGAACT GGAAAACCAC ACCGAAGTTA
AAGCTGCTGG TCAGTCCGCT CCGAAAGGTA CCAACGTTTC CGCTGACCTG TACAACTCCC
TGTGGGACGA AAACAAAACC CTGCGTGAAA AACAGGAAGA ATACATCACC AAAATCCAGA
ACGAAGAAAC CAAAAACAAA GAAGAAGAAC GTACCTTCAC CGAACTGCCG TACGAAGCTC
GTTACAAAGC TTGGAAATCC GAAAACGACG AACTGCGTGA AAACTACCGT CGTACCCTGG
ACAAATTCAA CACCGAACAG GGTAAAACCA CCCGTCTGGA AGAACAGAAC CGTGTTCGTT
ACACCCGTCA CACCCCGGAA GACAAACTGA AAAAAATCAT CGACGACCTG GACGCTAAAG
AACACCGTGT TCGTTACACC CGTCACACCC CGGAAGACAA ACTGAAAAAA ATCATCGACG
ACCTGGACGC TAAAGAACAC CGTGTTTACA TCACCCGTCG TATGACCAAA GAAGACGTTG
AAAAAATCGC TAACGACCTG GACACCGAAA ACCACGGTCT GAAACAGCAG AACGAACAGC
TGTCCACCGA AAAACAGGGT CTGGAAGAAC AGAACAAACA GCTGTCCACC GACCGTGTTT
CCCGTTCCAT GTCCCGTGAC GACCTGCTGA ACCGTGCTCA GGACCTGGAA GCTAAAAACC
ACGGTCTGGA ACACCAGAAC ACCAAACTGT CCACCGAAAA CAAAACCCTG CAGGAACAGG
CTGAAGCTCG TCAGAAAGAA GTTGCTACCC GTTCCCAGAC CGACACCCTG GAAAAAGTTC
AGGAACGTGC TGACAAATTC GAAATCGAAA ACAACACCCT GAAACTGAAA AACTCCGACC
TGTCCTTCAA CAACAAAGCT CTGAAAGACC ACAACGACGA ACTGACCGAA GCTGAAATCA
AAAAACCGCA GGCTGACTCC GCTTGGAACT GGCCGAAAGA ATACAACGCT CTGCTGAAAG
AAAACGAAGA ACTGAAAGTT GAACGTGAAA AATACCTGTC CTACGCTGAC GACAAAGAAA
AAGACCCGCA GTACCGTGCT CACCACCACC ACCACCACTA G 1481

*Fig. 2C*

Fusion Polypeptide 2 (MW: 54,174; pI: 5.87) (SEQ ID NO:10)

```
MAEIKKPQAD SAWNWPKEYN ALLKENEELK VEREKYLSYA DDKEKDPQYR AAVTRGTIND
PQRAKEALDK YELENHAVTR GTINDPQRAK EALDKYELEN HTEVKAAGQS APKGTNVSAD
LYNSLWDENK TLREKQEEYI TKIQNEETKN KEEERTFTEL PYEARYKAWK SENDELRENY
RRTLDKFNTE QGKTTRLEEQ NRVRYTRHTP EDKLKKIIDD LDAKEHRVRY TRHTPEDKLK
KIIDDLDAKE HRVYITRRMT KEDVEKIAND LDTENHGLKQ QNEQLSTEKQ GLEEQNKQLS
TDRVSRSMSR DDLLNRAQDL EAKNHGLEHQ NTKLSTENKT LQEQAEARQK EVATRSQTDT
LEKVQERADK FEIENNTLKL KNSDLSFNNK ALKDHNDELT EAEIKKPQAD SAWNWPKEYN
ALLKENEELK VEREKYLSYA DDKEKDPQYR AHHHHHH  457
```

*Fig. 2D*

Polynucleotide Encoding Fusion Polypeptide 3 (SEQ ID NO:19)

AGATCTCGAT CCCGCGAAAT TAATACGACT CACTATAGGG GAATTGTGAG CGGATAACAA
TTCCCCTCTA GAAATAATTT TGTTTAACTT TAAGAAGGAG ATATACCATG GAAGGTGTTT
CCGTTGGTTC CGACGCTTCC CTGCACAACC GTATCACCGA CCTGGAAGAA GAACGTGAAA
AACTGCTGAA CAAACTGGAC AAAGTTGAAG AAGAACACAA AAAAGACCAC GAACAGCTGG
AAAAAAAATC CGAAGACGTT GAATCCTCCA ACAACGCTGA ATCCTCCAAC ATCTCCCAGG
AATCCAAACT GATCAACACC CTGACCGACG AAAACGAAAA ACTGCGTGAA GAACTGCAGC
AGTACTACGC TCTGTCCGAC GCTAAAGAAG AAGAACCGCG TTACAAAGCT GACAACCAGT
CCCCGGCTCC GGTTAAAAAA GAAGCTAAAA AACTGAACGA AGCTGAACTG TACAACAAAA
TCCAGGAACT GGAAGAAGGT AAAGCTGAAC TGTTCGACAA ACTGGAAAAA GTTGAAGAAG
AAAACAAAAA AGTTAAAGAA GACTCCGACA ACATCAACCG TTCCGTTTCC GTTAAAGACA
ACGAAAAAGA ACTGCACAAC AAAATCGCTG ACCTGGAAGA AGAACGTGGT GAACACCTGG
ACAAAATCGA CGAACTGAAA GAAGAACTGA AAGCTAAAGA AAAATCCTCC GACTCCTCCC
GTGAAGTTAC CAACGAACTG ACCGCTTCCA TGTGGAAAGC TCAGGCTGAC TCCGCTAAAG
CTAAAGCTAA AGAACTGGAA AAACAGGTTG AAGAATACAA AAAAAACTAC GAAACCCTGG
AAAAAGGTTA CGACGACCTG GCTGAATCCC GTTCCGTTTC CCAGGGTTCC GTTTCCCTGG
AACTGTACGA CAAACTGTCC GACGAAAACG ACATCCTGCG TGAAAAACAG GACGAATACC
TGACCAAAAT CGACGGTCTG GACAAAGAAA ACAAAGAATA CGCTTCCCAG GAATCCCAGA
ACTCCCGTTC CATCACCAAC GAACAGCTGA TCGACAAACT GGTTGAAGAA AACAACGACC
TGAAAGAAGA ACGTGCTAAA TACCTGGACC TGCTGGACAA CCGTGAAAAA GACCCGCAGT
ACCGTGCTCT GATGGGTGAA GCTGAAAAAA AAGTTGAAGT TGCTGACTCC AACGCTTCCT
CCGTTGCTAA ACTGTACAAC CAGATCGCTG ACCTGACCGA CAAAAACGGT GAATACCTGG
AACGTATCGA AGAACTGGAA GAACGTCAGA AAAACCTGGA AAAACTGGAA GAAGGTGTTT
CCGTTGGTTC CGACGCTTCC CTGCACAACC GTATCACCGA CCTGGAAGAA GAACGTGAAA
AACTGCTGAA CAAACTGGAC AAAGTTGAAG AAGAACACAA AAAAGACCAC GAACAGCTGG
AAAAAAAATC CGAAGACGTT CACCACCACC ACCACCACTA G 1481

*Fig. 2E*

Fusion Polypeptide 3 (MW: 53,086; pI: 4.68) (SEQ ID NO:11)

```
MEGVSVGSDA SLHNRITDLE EEREKLLNKL DKVEEEHKKD HEQLEKKSED VESSNNAESS
NISQESKLIN TLTDENEKLR EELQQYYALS DAKEEEPRYK ADNQSPAPVK KEAKKLNEAE
LYNKIQELEE GKAELFDKLE KVEEENKKVK EDSDNINRSV SVKDNEKELH NKIADLEEER
GEHLDKIDEL KEELKAKEKS SDSSREVTNE LTASMWKAQA DSAKAKAKEL EKQVEEYKKN
YETLEKGYDD LAESRSVSQG SVSLELYDKL SDENDILREK QDEYLTKIDG LDKENKEYAS
QESQNSRSIT NEQLIDKLVE ENNDLKEERA KYLDLLDNRE KDPQYRALMG EAEKKVEVAD
SNASSVAKLY NQIADLTDKN GEYLERIEEL EERQKNLEKL EEGVSVGSDA SLHNRITDLE
EEREKLLNKL DKVEEEHKKD HEQLEKKSED VHHHHHH  457
```

*Fig. 2F*

Polynucleotide Encoding Fusion Polypeptide 4 (SEQ ID NO:20)

AGATCTCGAT CCCGCGAAAT TAATACGACT CACTATAGGG GAATTGTGAG CGGATAACAA
TTCCCCTCTA GAAATAATTT TGTTTAACTT TAAGAAGGAG ATATACCATG GACAACCCGC
GTTACACCGA CGCTCACAAC GCTGTTACCC AGGGTCGTAC CGTTCCGCTG CAGAACCTGC
TGCACGAAAT GGACAAAAAC GGTAAACTGC GTTCCGAAAA CGAAGAACTG AAAGCTGACC
TGCAGAAAAA AGAACAGGAA GACTCCTCCT CCCGTGACAT CACCGAAGCT GGTGTTTCCA
AATTCTGGAA ATCCAAATTC GACGCTGAAC AGAACCGTGC TAACGAACTG GAAAAAAAAC
TGTCCGGTTA CGAAAAAGAC TACAAAACCC TGGAACAGGA ATACGAAAAC GCTGGTTCCG
AAGAAAACGT TCCGAAACAG CAGTACAACG CTCTGTGGGA AGAAAACGAA GACCTGCGTG
GTCGTGAACG TAAATACATC GCTAAACTGG AAAAAGAAGA AATCCAGAAC GGTGAACTGA
ACGAAAAAAA CCGTAAACTG GAATCCCCGC GTGAAGTTAC CAACGAACTG GCTGCTTCCG
TTTGGAAAAA AAAAGTTGAA GAAGCTAAAG AAAAAGCTTC CAAACTGGAA AAACAGCTGG
AAGAAGCTCA GAAAGACTAC TCCGAAATCG AAGGTAAACT GGAACAGTTC GTTGAAAAAA
AAGTTGAAGC TGCTGAAAAC AACGTTTCCT CCGTTGCTCG TCGTGAAAAA GAACTGTACG
ACCAGATCGC TGACCTGACC GACAAAAACG GTGAATACCT GGAACGTATC GGTGAACTGG
AAGAACGTCA GAAAAACCTG GACGACCGTT CCGTTTCCAC CAACTCCGGT TCCGTTTCCA
CCCCGTACAA CAACCTGCTG AACGAATACG ACGACCTGCT GGCTAAACAC GGTGAACTGC
TGTCCGAATA CGACGCTCTG AAAGAAAAAC AGGACAAAAA CCAGGAAGAA AACTCCAAAA
ACCCGGCTCC GGCTCCGGCT TCCGCTGTTC CGGTTAAAAA AGAAGCTACC AAACTGTCCG
AAGCTGAACT GTACAACAAA ATCCAGGAAC TGGAAGAAGG TAAAGCTGAA CTGTTCGACA
AACTGGAAAA AGTTGAAGAA GACAACCCGC GTTACACCGA CGCTCACAAC GCTGTTACCC
AGGGTCGTAC CGTTCCGCTG CAGAACCTGC TGCACGAAAT GGACAAAAAC GGTAAACTGC
GTTCCGAAAA CGAAGAACTG AAAGCTGACC TGCAGAAAAA AGAACAGGAA CACCACCACC
ACCACCACTA G

*Fig. 2G*

Fusion Polypeptide 4 (MW: 47,136; p I: 4.99) (SEQ ID NO:12)

MDNPRYTDAH NAVTQGRTVP LQNLLHEMDK NGKLRSENEE LKADLQKKEQ EDSSSRDITE
AGVSKFWKSK FDAEQNRANE LEKKLSGYEK DYKTLEQEYE NAGSEENVPK QQYNALWEEN
EDLRGRERKY IAKLEKEEIQ NGELNEKNRK LESPREVTNE LAASVWKKKV EEAKEKASKL
EKQLEEAQKD YSEIEGKLEQ FVEKKVEAAE NNVSSVARRE KELYDQIADL TDKNGEYLER
IGELEERQKN LDDRSVSTNS GSVSTPYNNL LNEYDDLLAK HGELLSEYDA LKEKQDKNQE
ENSKNPAPAP ASAVPVKKEA TKLSEAELYN KIQELEEGKA ELFDKLEKVE EDNPRYTDAH
NAVTQGRTVP LQNLLHEMDK NGKLRSENEE LKADLQKKEQ EHHHHHH 407

*Fig. 2H*

GROUP A *STREPTOCOCCUS* MULTIVALENT VACCINE

CROSS-REFERENCE TO RELATED APPLICATIONS

This application claims benefit under 35 U.S.C. §119(e) of U.S. Provisional Patent Application No. 61/498,397 filed Jun. 17, 2011, and U.S. Provisional Patent Application No. 61/641,448 filed May 2, 2012, which are each incorporated herein by reference in their entirety.

STATEMENT OF GOVERNMENT INTEREST

This invention was made with government support under Grant Numbers AI-010085, AI-060592, and 5T35DK007405 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 920098_414_SEQUENCE_LISTING.txt. The text file is 93 KB, was created on Jun. 14, 2012, and is being submitted electronically via EFS-Web.

BACKGROUND

1. Technical Field

Safe and effective vaccines to prevent group A streptococcal (GAS) infections are needed. A multivalent vaccine is described herein that induces an immune response against multiple GAS serotypes and that may be useful for immunizing subjects in need thereof.

2. Description of the Related Art

Efforts to develop safe and effective vaccines to prevent group A streptococcal (GAS) infections have been ongoing for decades. Although a number of GAS antigens have been identified as potential vaccine components (see, e.g., Steer et al., *Curr. Opin. Infect. Dis.* 22:544-52 (2009)), the lead candidates are the type-specific peptides representing the amino-terminal regions of the surface M proteins (see, e.g., Kotloff et al., *JAMA* 292:709-15 (2004); McNeil et al., *Clin. Infect. Dis.* 41:1114-22 (2005)).

The major burden of disease in North America, Europe, and other economically developed regions and countries is uncomplicated pharyngitis and serious, invasive infections (see, e.g., Carapetis et al., *The Lancet Infectious Diseases* 5:685-94 (2005)). The global burden of GAS infections is most significant in poor countries where acute rheumatic fever (ARF) and rheumatic heart disease (RHD) are rampant (see, e.g., Carapetis et al., supra). Vaccine prevention of the infections that trigger ARF using M protein-based vaccines has been considered a challenge because the GAS emm types present in developing countries differ compared to economically developed areas of the world (see, e.g., Steer et al., *The Lancet Infectious Diseases* 9:611-16 (2009)). Immunogenicity of a 26-valent M protein-based vaccine in pre-clinical (see, e.g., Hu et al., supra) and clinical studies (see, e.g., McNeil et al., supra) has been reported. However, the 26-valent vaccine does not provide protection against infection by a sufficient number of different GAS serotypes for optimum benefit and use in both developing and developed countries. Accordingly, a need exists for development of improved therapeutics and vaccines, which can be economically produced, for treating and preventing GAS infections.

BRIEF SUMMARY

Briefly, provided herein are immunogenic peptides, fusion polypeptides, and immunogenic compositions comprising these immunogenic peptides and fusion polypeptides, capable of inducing an immune response against multiple strains of GAS. The immunogenic compositions described herein are a significant improvement to immunogenic compositions previously described in the art for preventing or treating GAS infections. Methods for using the immunogenic compositions are also provided. The various embodiments of the immunogenic peptides, fusion polypeptides, and immunogenic compositions and methods are summarized below.

Embodiment 1. An immunogenic composition comprising at least 31 immunogenic peptides, wherein each immunogenic peptide is different and comprises at least 25 contiguous amino acids from the amino terminal portion of a different M protein or a Spa protein, wherein each different M protein is independently selected from the M protein of group A *streptococcus* (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18, and wherein the immunogenic composition induces an immune response against GAS.

Embodiment 2. The immunogenic composition of Embodiment 1, wherein at least four of the different immunogenic peptides are linked in tandem to form a fusion polypeptide.

Embodiment 3. The immunogenic composition of Embodiment 1 or Embodiment 2 comprising a first fusion polypeptide, a second fusion polypeptide, a third fusion polypeptide, and a fourth fusion polypeptide that each comprises at least six of the different immunogenic peptides linked in tandem.

Embodiment 4. The immunogenic composition of Embodiment 3, wherein the first fusion polypeptide comprises eight of the different immunogenic peptides linked in tandem, wherein each of the eight immunogenic peptides comprises at least 25 contiguous amino acids from the amino terminal portion of a different M protein or the Spa protein, wherein each different M protein is independently selected from the M protein of GAS serotype 1, 2, 3, 6, 12, 18, and 28, and the Spa protein is from GAS serotype 18.

Embodiment 5. The immunogenic composition of Embodiment 4, wherein the immunogenic peptide located at the carboxy terminal end of the first fusion polypeptide is a duplicate of the immunogenic peptide located at the amino terminal end of the first fusion polypeptide.

Embodiment 6. The immunogenic composition of Embodiment 5, wherein the immunogenic peptide that is duplicated comprises at least 25 contiguous amino acids from the amino terminal portion of the M protein of GAS serotype 1.

Embodiment 7. The immunogenic composition of any one of Embodiments 3-6, wherein the second fusion polypeptide comprises eight of the different immunogenic peptides linked in tandem, and wherein each of the eight immunogenic peptides comprises at least 25 contiguous amino acids from the amino terminal portion of a different M protein independently selected from the M protein of GAS serotype 4, 5, 11, 14, 19, 24, 29, and 75.

Embodiment 8. The immunogenic composition of Embodiment 7, wherein the immunogenic peptide located at the carboxy terminal end of the second fusion polypeptide is a duplicate of the immunogenic peptide located at the amino terminal end of the second fusion polypeptide.

Embodiment 9. The immunogenic composition of Embodiment 8, wherein the immunogenic peptide that is duplicated comprises at least 25 contiguous amino acids from the amino terminal portion of the M protein of GAS serotype 4.

Embodiment 10. The immunogenic composition of any one of Embodiments 3-9, wherein the third fusion polypeptide comprises eight of the different immunogenic peptides linked in tandem, and wherein each of the eight immunogenic peptides comprises at least 25 contiguous amino acids from the amino terminal portion of a different M protein independently selected from the M protein of GAS serotype 22, 44, 58, 73, 77, 78, 89, and 118.

Embodiment 11. The immunogenic composition of Embodiment 10, wherein the immunogenic peptide located at the carboxy terminal end of the third fusion polypeptide is a duplicate of the immunogenic peptide located at the amino terminal end of the third fusion polypeptide.

Embodiment 12. The immunogenic composition of Embodiment 11, wherein the immunogenic peptide that is duplicated comprises at least 25 contiguous amino acids from the amino terminal portion of the M protein of GAS serotype 77.

Embodiment 13. The immunogenic composition of any one of Embodiments 3-12, wherein the fourth fusion polypeptide comprises seven of the different immunogenic peptides linked in tandem, and wherein each of the seven immunogenic peptides comprises at least 25 contiguous amino acids from the amino terminal portion of a different M protein independently selected from the M protein of GAS serotype 49, 81, 82, 83, 87, 92, and 114.

Embodiment 14. The immunogenic composition of Embodiment 13, wherein the immunogenic peptide located at the carboxy terminal end of the fourth fusion polypeptide is a duplicate of the immunogenic peptide located at the amino terminal end of the fourth fusion polypeptide.

Embodiment 15. The immunogenic composition of Embodiment 14, wherein the immunogenic peptide that is duplicated comprises at least 25 contiguous amino acids from the amino terminal portion of the M protein of GAS serotype 83.

Embodiment 16. The immunogenic composition of any one of Embodiments 1-15, wherein each of the immunogenic peptides comprises (a) the at least 25 contiguous amino acids from the amino terminal portion of the different M protein or the Spa protein in duplicate; (b) at least 40 contiguous amino acids from the amino terminal portion of the different M protein or the Spa protein; (b) at least 45 contiguous amino acids from the amino terminal portion of the different M protein or the Spa protein; or (d) at least 50 contiguous amino acids from the amino terminal portion of the different M protein or the Spa protein.

Embodiment 17. An immunogenic composition comprising:

(a) a first fusion polypeptide comprising an amino acid sequence at least 85% identical to the amino acid sequence set forth in SEQ ID NO:1;

(b) a second fusion polypeptide comprising an amino acid sequence at least 85% identical to the amino acid sequence set forth in SEQ ID NO:2;

(c) a third fusion polypeptide comprising an amino acid sequence at least 85% identical to the amino acid sequence set forth in SEQ ID NO:3; and (d) a fourth fusion polypeptide comprising an amino acid sequence at least 85% identical to the amino acid sequence set forth in SEQ ID NO:4, wherein the immunogenic composition induces an immune response against group A *streptococcus*.

Embodiment 18. The immunogenic composition of Embodiment 17 wherein (a) the first fusion polypeptide comprises an amino acid sequence at least 90% identical to the amino acid sequence set forth in SEQ ID NO:1; (b) the second fusion polypeptide comprises an amino acid sequence at least 90% identical to the amino acid sequence set forth in SEQ ID NO:2; (c) the third fusion polypeptide comprises an amino acid sequence at least 90% identical to the amino acid sequence set forth in SEQ ID NO:3; and (d) the fourth fusion polypeptide comprises an amino acid sequence at least 90% identical to the amino acid sequence set forth in SEQ ID NO:4.

Embodiment 19. The immunogenic composition of Embodiment 17, wherein (a) the first fusion polypeptide comprises an amino acid sequence at least 95% identical to the amino acid sequence set forth in SEQ ID NO:1; (b) the second fusion polypeptide comprises an amino acid sequence at least 95% identical to the amino acid sequence set forth in SEQ ID NO:2; (c) the third fusion polypeptide comprises an amino acid sequence at least 95% identical to the amino acid sequence set forth in SEQ ID NO:3; and (d) the fourth fusion polypeptide comprises an amino acid sequence at least 95% identical to the amino acid sequence set forth in SEQ ID NO:4.

Embodiment 20. The immunogenic composition of Embodiment 17, wherein (a) the first fusion polypeptide comprises an amino acid sequence at least 97% identical to the amino acid sequence set forth in SEQ ID NO:1; (b) the second fusion polypeptide comprises an amino acid sequence at least 97% identical to the amino acid sequence set forth in SEQ ID NO:2; (c) the third fusion polypeptide comprises an amino acid sequence at least 97% identical to the amino acid sequence set forth in SEQ ID NO:3; and (d) the fourth fusion polypeptide comprises an amino acid sequence at least 97% identical to the amino acid sequence set forth in SEQ ID NO:4.

Embodiment 21. The immunogenic composition of Embodiment 17, wherein (a) the first fusion polypeptide comprises the amino acid sequence set forth in SEQ ID NO:1; (b) the second fusion polypeptide comprises the amino acid sequence set forth in SEQ ID NO:2; (c) the third fusion polypeptide comprises the amino acid sequence set forth in SEQ ID NO:3; and (d) the fourth fusion polypeptide comprises the amino acid sequence set forth in SEQ ID NO:4.

Embodiment 22. The immunogenic composition of any one of Embodiments 1-21, further comprising a pharmaceutically acceptable excipient.

Embodiment 23. The immunogenic composition of any one of Embodiments 1-22, further comprising a pharmaceutically acceptable adjuvant.

Embodiment 24. The immunogenic composition of any one of Embodiments 1-23, wherein the immune response against group A *streptococcus* comprises an immune response against at least each of GAS 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118 serotypes.

Embodiment 25. A method for inducing an immune response against group A *streptococcus* in a subject, comprising administering to the subject the immunogenic composition of any one of Embodiments 1-24.

Embodiment 26. A method for reducing the likelihood of occurrence of a group A *streptococcus* infection in a subject, comprising administering to the subject the immunogenic composition of any one of Embodiments 1-24.

Embodiment 27. A method for preventing or treating a group A *streptococcus* infection in a subject, comprising administering to the subject the immunogenic composition of any one of Embodiments 1-24.

Embodiment 28. The immunogenic composition of any one of Embodiments 1-24 for use in preventing or treating a group A *streptococcus* infection.

Embodiment 29. Use of the immunogenic composition of any one of Embodiments 1-24 for the manufacture of a vaccine to prevent or treat a group A *streptococcus* infection.

Embodiment 30. The immunogenic composition of any one of Embodiments 1-24 for preventing or treating a group A *streptococcus* infection.

Embodiment 31. A fusion polypeptide comprising:

(a) an amino acid sequence at least 85% identical to the amino acid sequence set forth in SEQ ID NO:1;

(b) an amino acid sequence at least 85% identical to the amino acid sequence set forth in SEQ ID NO:2;

(c) an amino acid sequence at least 85% identical to the amino acid sequence set forth in SEQ ID NO:3; or (d) an amino acid sequence at least 85% identical to the amino acid sequence set forth in SEQ ID NO:4, wherein the fusion polypeptide induces an immune response against group A *streptococcus*.

Embodiment 32. The fusion polypeptide of Embodiment 31 comprising:

(a) an amino acid sequence at least 90% identical to the amino acid sequence set forth in SEQ ID NO:1;

(b) an amino acid sequence at least 90% identical to the amino acid sequence set forth in SEQ ID NO:2;

(c) an amino acid sequence at least 90% identical to the amino acid sequence set forth in SEQ ID NO:3; or (d) an amino acid sequence at least 90% identical to the amino acid sequence set forth in SEQ ID NO:4.

Embodiment 33. The fusion polypeptide of Embodiment 31 comprising:

(a) an amino acid sequence at least 95% identical to the amino acid sequence set forth in SEQ ID NO:1;

(b) an amino acid sequence at least 95% identical to the amino acid sequence set forth in SEQ ID NO:2;

(c) an amino acid sequence at least 95% identical to the amino acid sequence set forth in SEQ ID NO:3; or (d) an amino acid sequence at least 95% identical to the amino acid sequence set forth in SEQ ID NO:4.

Embodiment 34. The fusion polypeptide of Embodiment 31 comprising:

(a) an amino acid sequence at least 97% identical to the amino acid sequence set forth in SEQ ID NO:1;

(b) an amino acid sequence at least 97% identical to the amino acid sequence set forth in SEQ ID NO:2;

(c) an amino acid sequence at least 97% identical to the amino acid sequence set forth in SEQ ID NO:3; or (d) an amino acid sequence at least 97% identical to the amino acid sequence set forth in SEQ ID NO:4.

Embodiment 35. The fusion polypeptide of Embodiment 31 comprising:

(a) the amino acid sequence set forth in SEQ ID NO:1;

(b) the amino acid sequence set forth in SEQ ID NO:2;

(c) the amino acid sequence set forth in SEQ ID NO:3; or (d) the amino acid sequence set forth in SEQ ID NO:4.

Embodiment 36. An isolated polynucleotide encoding the fusion polypeptide of any one of Embodiments 31-35.

Embodiment 37. A recombinant expression vector comprising the isolated polynucleotide of Embodiment 36 operatively linked to at least one expression control region.

Embodiment 38. An isolated host cell transfected, transduced, or transformed with the recombinant expression vector of Embodiment 37.

Embodiment 39. A process for producing the fusion polypeptide of any one of Embodiments 31-35, the method comprising:

(a) culturing the isolated host cell of Embodiment 38; and (b) isolating the fusion polypeptide from the host cell culture.

Embodiment 40. A method for detecting an antibody that specifically binds to the fusion polypeptide of any one of Embodiments 31-35 in a biological sample suspected of containing the antibody, the method comprising:

(a) contacting the biological sample with (i) an immunogenic peptide comprising at least 25 contiguous amino acids of the amino terminal portion of an M protein or a Spa protein, wherein the M protein is selected from the M protein of group A *streptococcus* (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18;

(ii) a dimeric peptide, wherein each peptide of the dimeric peptide is different and comprises at least 25 contiguous amino acids of the amino terminal portion of a different M protein or a Spa protein, wherein each different M protein is independently selected from the M protein of group A *streptococcus* (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18; or (iii) the fusion polypeptide of any one of Embodiments 31-35; and (b) detecting specific binding of the immunogenic peptide, dimeric peptide, or fusion polypeptide with the biological sample, thereby indicating that the biological sample contains the antibody.

As used herein and in the appended claims, the singular forms “a,” “and,” and “the” include plural referents unless the context clearly dictates otherwise. Thus, for example, reference to “a polypeptide” may refer to one or more polypeptides, or a plurality of such polypeptides, and reference to “a cell” or “the cell” includes reference to one or more cells and equivalents thereof (e.g., plurality of cells) known to those skilled in the art, and so forth. Similarly, reference to “a composition” includes a plurality of such compositions, and refers to one or more compositions unless the context clearly dictates otherwise. When steps of a method are described or claimed, and the steps are described as occurring in a particular order, the description of a first step occurring (or being performed) “prior to” (i.e., before) a second step has the same meaning if rewritten to state that the second step occurs (or is performed) “subsequent” to the first step. The term “about” when referring to a number or a numerical range means that the number or numerical range referred to is an approximation within experimental variability (or within statistical experimental error), and thus the number or numerical range may vary between 1% and 15% of the stated number or numerical range. The term “comprising” (and related terms such as “comprise” or “comprises” or “having” or “including”) is not intended to exclude that in other certain embodiments, for example, an embodiment of any composition of matter, composition, method, or process, or the like, described herein, may “consist of” or “consist essentially of” the described features.

As used herein, the term “isolated” means that a material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such a nucleic acid could be part of a vector and/or such nucleic acid or polypeptide could be part of a composition, and still be isolated in that the vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons). Amino acids may be referred to herein according to the single letter and three letter codes, which are understood according to common textbook knowledge in the art, and therefore with which a person skilled in the art is familiar. The term "fusion polypeptide" used herein may also be used interchangeably with "fusion protein," and unless specifically indicated otherwise, the two terms are not meant to indicate molecules that have distinguishable properties or characteristics.

BRIEF DESCRIPTION OF THE DRAWINGS

FIG. 2A-2H provides the nucleotide sequences of four synthetic polynucleotides (FIGS. 2A (SEQ ID NO:17); 2C (SEQ ID NO:18); 2E (SEQ ID NO:19); and 2G (SEQ ID NO:20)) and the respective amino acid sequence of the encoded constituent recombinant polypeptides (FIGS. 2B (SEQ ID NO:9); 2D (SEQ ID NO:10); 2F (SEQ ID NO:11); and 2H (SEQ ID NO:12)). Each polynucleotide was synthesized to contain an upstream T7 promoter, ribosome binding site, start codon (ATG in bold, beginning at position 108 of each of FIG. 2A, 2C, 2E, 2G), 3' polyhistidine motif, and a termination codon.

FIG. 4B provides a graphic of the level of bactericidal antibodies evoked by the 30-valent M protein-based GAS immunogenic composition. Immune serum from one of the rabbits immunized with 800 μg doses of the immunogenic composition was used in bactericidal assays against all serotypes of GAS represented in the immunogenic composition. Percent killing was calculated as described in the Examples.

DETAILED DESCRIPTION

Figure 1:
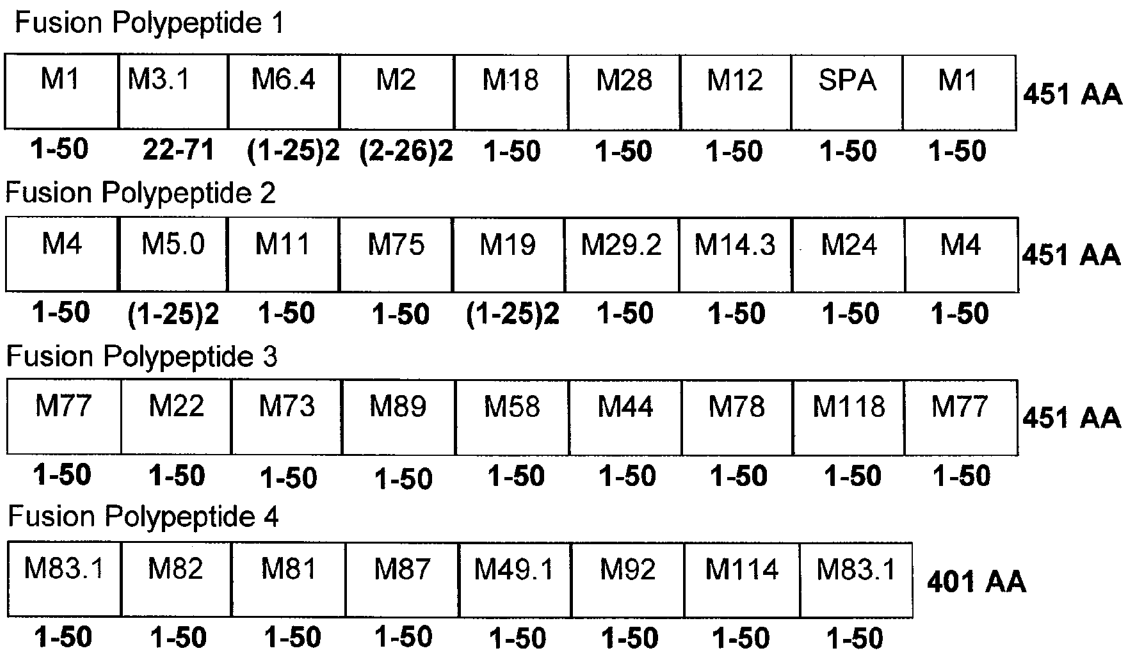
FIG. 1 presents a schematic diagram of four proteins comprising a 30-valent M protein-based GAS immunogenic composition.

Provided herein are immunogenic compositions that are capable of evoking (i.e., inducing) an immune response against multiple strains of group A *streptococcus* (GAS) and that represent a significant improvement to immunogenic compositions previously described in the art. As described herein, the combination of immunogenic peptides derived from GAS strains in the multivalent immunogenic compositions evoke immune responses not only against the GAS strains from which the immunogenic peptides were derived but also against multiple additional strains of GAS not represented by immunogenic peptides in the composition.

Group A *streptococcus* (*Streptococcus pyogenes*) has two major, surface-exposed anti-phagocytic factors, capsule and M protein, which allow these organisms to colonize and survive in a host. The cell surface M protein of group A *streptococci* (GAS) is one of the major virulence factors for this pathogen. The M protein, which is encoded by the emm gene, extends from the cell surface as an α-helical coiled-coil dimer that appears as a fibril on the surface of a GAS bacterium. The M proteins form an antigenically diverse group and GAS strains have been serologically categorized according to M protein serotypes. More than 120 M protein serotypes have been identified, and within some serotypes, subtypes have also been identified. By way of example, the M proteins of GAS serotype 3 include related subtypes, which are designated as 3.0, 3.1, 3.2, etc. Antibodies to the M protein can facilitate opsonophagocytosis by phagocytic cells present in blood.

As described herein and by way of example, a 30-valent immunogenic composition (which may also be referred to herein and in the art as a vaccine) was constructed that contains immunogenic peptides derived from the M protein of GAS serotypes prevalent in North America, Europe, and developing countries. Selection of serotypes represented in the composition was based on available epidemiology and serotype prevalence of GAS infections in North America and Europe (see, e.g., Shulman et al., *Clin. Infect. Dis.* 39:325-32 (2004)); Shulman et al., *Clin. Infect. Dis.* 49:78-84 (2009); O'Loughlin et al., *Clin. Infect. Dis.* 45:853-62 (2007); Luca-Harari et al., *J. Clin. Microbiol.* 47:1155-65 (2009)), and in some developing countries (see, e.g., Steer et al., supra). These immunogenic compositions also contain an immunogenic peptide from a protein referred to in the art as Spa, which evokes antibodies that cross react with more than one GAS serotype. The immunogenic compositions described herein, such as the composition comprising thirty different M protein peptide immunogens and a Spa peptide immunogen, more adequately represents the epidemiology of pharyngitis and invasive GAS infections.

In addition, the immunogenic compositions described herein include an immunogenic peptide derived from the M protein of the GAS serotype 4. GAS serotype 4 causes a significant portion of GAS disease, approximately 9% of uncomplicated pharyngitis in North America and 5% of invasive GAS infections in Europe (see, e.g., Shulman et al., *Clin. Infect. Dis.* 2009, supra; Luca-Harari et al., supra). A member of the M protein family called Arp4 (see, e.g., Johnsson et al., *J. Immunol.* 153:3557-64 (1994)) present on the cell surface of GAS serotype 4 bacteria was initially believed not to be required for virulence or for resistance to phagocytosis, unlike other members of the M protein family (see, e.g., Husmann et al., *Infect. Immun.* 63:345-48 (1995)). Upon further experimentation, an immunogenic peptide from the amino terminal end of the Arp4 (M4) protein that evokes opsonic antibodies in an immunized host was identified (see, e.g., Courtney et al., supra). The addition of an M4 immunogenic peptide to a GAS immunogenic composition improves the efficacy of multivalent vaccines with respect to both uncomplicated and complicated infections by increasing, from approximately 78% to 90%, the number of GAS strains to which such a multivalent immunogenic composition induces an immune response.

Distinct from M protein, a polypeptide designated Spa (Streptococcal protective antigen) contains epitopes that induce production of opsonic, protective antibodies. Spa polypeptides may be serotype specific, such as the Spa polypeptide from GAS serotype 36, whereas other Spa polypeptides, such as Spa polypeptide isolated from GAS serotype 18, evoke antibodies that bind to multiple GAS serotypes. The Spa polypeptide of GAS serotype 18 induces antibodies that bind to and are protective against serotypes 3 and 28 as well as serotype 18 (see, e.g., U.S. Pat. No. 7,063,850; Ahmed et al., *Eur. J. Clin. Microbiol. Infect. Dis.* 29:51-57 (2010) Epub 2009 Oct. 29; McLellan et al., *Infect. Immun.* 69:2943-49 (2001); Dale et al., *J. Clin. Invest.* 103:1261-68 (1999)).

In one embodiment, an immunogenic composition is provided that comprises four different fusion proteins that each comprise seven or eight GAS M protein or GAS Spa protein immunogenic fragments linked in tandem. An exemplary composition was immunogenic in rabbits and evoked bactericidal antibodies against all serotypes of GAS represented by immunogenic peptides included in the composition. In addition, unexpectedly and in contrast to a 26-valent immunogenic composition previously described in the art, antisera obtained from animals immunized with the exemplary 30-valent composition described herein also contained significant levels of bactericidal antibodies against GAS serotypes from which an immunogenic peptide fragment was not included in the composition (i.e., a non-vaccine GAS serotype or non-represented GAS serotype). Therefore, the potential efficacy of the immunogenic compositions described herein, such as the 30-valent immunogenic composition, may extend well beyond the serotypes represented by the subunit M peptides and the Spa peptide. This and other embodiments and uses therefor are described in greater detail herein.

Immunogenic Compositions

In one embodiment, an immunogenic composition is provided that comprises a plurality of GAS immunogenic peptide. In a particular embodiment, the immunogenic composition comprises at least 31 different immunogenic peptides. Each immunogenic peptide comprises an amino acid sequence that is located at the amino (also called herein and in the art, $NH_2$) terminal portion of one of 31 different GAS polypeptides, respectively. In a particular embodiment, each of at least 30 different immunogenic peptides is derived from the amino acid sequence of at least 30 M proteins from 30 different GAS serotypes, respectively. Each immunogenic peptide of an M protein comprises at least 25 contiguous amino acids from the amino terminal portion of the M protein. The compositions described herein also comprise an immunogenic peptide that comprises at least 25 contiguous amino acids from the amino terminal portion of a Spa polypeptide, which in particular embodiments is the Spa polypeptide expressed and present on the cell surface of GAS serotype M18 strains. In another particular embodiment, an immunogenic composition is provided that comprises at least four fusion polypeptides that comprise the plurality of immunogenic peptides (e.g., at least 31 different immunogenic peptides derived from GAS M proteins or GAS Spa proteins).

The amino terminal regions of M proteins have been shown to evoke antibodies with the greatest bactericidal (protective) activity and are least likely to cross-react with human tissues (see, e.g., Dale, *Adv. Exp. Med. Biol.* 609:53-63 (2008)). One approach has been to construct recombinant hybrid proteins containing M protein peptides combined into multivalent vaccines designed to elicit opsonic antibodies against epidemiologically important serotypes of group A *streptococci* (see, e.g., Dale, *Inf. Dis. Clin. N Amer.* 13:227-43 (1999); Hu et al., *Infect. Immun.* 70:2171-77 (2002)).

The anti-GAS immunogenic compositions described herein provide a significant improvement compared with previously described vaccine compositions. In one embodiment, a 30-valent immunogenic composition is provided that includes immunogenic peptides of M proteins and a Spa protein that evoked an immune response not only against each GAS serotype represented by an M protein immunogenic peptide but also, significantly, to more non-vaccine serotypes (i.e., GAS serotypes not represented in the immunogenic composition by an M protein immunogenic peptide or a Spa immunogenic peptide). Importantly, in addition, the immunogenic compositions described herein include an immunogenic peptide from the M protein of GAS serotype 4 (see, e.g., Courtney et al., *Molec. Microbiol.* 59:936-47 (2006)). GAS serotype 4 causes approximately 9% of uncomplicated pharyngitis in North America and 5% of invasive GAS disease in Europe (see, e.g., Shulman et al., *Clin. Infect. Dis.* 49:78-84 (2009); Luca-Harari et al., *J. Clin. Microbiol.* 47:1155-65 (2009))); therefore, inclusion of an M4 immunogenic peptide greatly improves the efficacy of a multivalent GAS vaccine.

The immunogenic compositions comprising GAS immunogenic peptides described herein evoke an immune response against GAS and more particularly against each of the GAS serotypes that are represented in the vaccine and from which the immunogenic peptides were derived. In addition, the immunogenic compositions described herein evoke an immune response against GAS serotypes from which an immunogenic peptide was not obtained and therefore not included in the immunogenic composition (also called herein non-vaccine GAS serotypes or non-represented GAS serotypes). Terms, such as "30-valent" or "26-valent," used herein refer to the number of GAS serotypes from which immunogenic peptides were obtained or derived. The number of immunogenic peptides included in an immunogenic composition may be greater than the indicated valency. For example, the immunogenic compositions comprising 31 immunogenic peptides described herein may be referred to as a 30-valent composition because the Spa immunogenic peptide (described herein and in the art) included in the composition can be obtained from GAS serotype M18, and an immunogenic peptide from the M protein of serotype M18 is also included in the vaccine composition.

Immunogenic compositions were designed and constructed to provide compositions that evoke an immune response against the greatest number of clinically relevant GAS serotypes regardless of geographic location. Accordingly, to maximize clinical use and efficacy, GAS serotypes prevalent in one or more geographic areas, which may be determined from epidemiological data available in the art, may serve as the source of M protein immunogenic fragments or other GAS polypeptide immunogenic fragments (e.g., a Spa immunogenic fragment). GAS serotypes represented by immunogenic fragments in immunogenic compositions described herein include those that cause non-invasive infections (e.g., pharyngitis, impetigo, erysipelas, and cellulitis)

and GAS serotypes that cause invasive infections (e.g., GAS infections of the blood (bacteremia), muscle, and lung (pneumonia), necrotizing fasciitis, and streptococcal toxic shock syndrome), and nonsuppurative sequelae such as acute rheumatic fever, reactive arthritis, and glomerulonephritis (see, e.g., Cunningham, *Clin. Microbiol. Rev.* 13:470 (2000)).

Epidemiology data may be obtained from public and/or private local, national, and international organizations and investigators. By way of example, serotypes of GAS from which immunogenic peptides of M proteins may be selected for use in immunogenic compositions based on the epidemiology of non-invasive infections, for example, pharyngitis in pediatric subjects in North America (see, e.g., Shulman et al., *Clin. Infect. Dis.* 2009, supra); (2) invasive GAS infections (see, e.g., Active Bacterial Core Surveillance of the Emerging Infections Program Network, supported by the Centers for Disease Control and Prevention) (see, e.g., O'Loughlin et al., supra); (3) invasive infections in Europe (for example, as reported by the StrepEuro consortium, see Luca-Harari et al., supra); and/or (4) GAS serotypes prevalent in developing countries (see, e.g., Steer et al., *The Lancet Infectious Diseases* 9:611-16 (2006)). Also included in the immunogenic compositions described herein (e.g., the 30-valent vaccine composition) are M peptides from serotypes of GAS that are currently or have been historically considered "rheumatogenic" (see, e.g., Shulman et al., *Clin. Infect. Dis.* 42:441-47 (2006)). In addition, the amino-terminal peptide fragment of Spa18, a protective antigen that is expressed by at least several serotypes of group A *streptococci*, such as but not limited to, GAS serotype 18, GAS serotype 3, and GAS serotype 28, may be included in the multivalent immunogenic compositions described herein (see, e.g., Dale et al., *J. Clin. Invest.* 103:1261-68 (1999); U.S. Pat. No. 7,063,850; International Patent Application Publication No. WO 00/37648).

The amino acid sequences of M proteins and subtypes of M proteins are available in protein databases, such as GenBank, GenEMBL, and Swiss Prot databases. M protein sequences are also available at the Center for Disease Control (CDC) emm typing center website that may be found by accessing the Internet at cdc.gov/ncidod/biotech/strep/emmtypes. The amino acid sequence of Spa polypeptides are also available in public databases and described in Dale et al., *J. Clin. Invest.* 103:1261-68 (1999); U.S. Pat. No. 7,063,850; and International Patent Application Publication No. WO 00/37648. Criteria for subtyping of GAS M serotypes as currently used in the art is described by Facklam et al., *Emerg. Infect. Dis.* 5:247-53 (1999).

Also long known in the art, region(s) of M proteins comprise amino acid sequences that induce antibodies that cross-react with host tissue, for example, human heart (see, e.g., Dale et al., *J. Exp. Med.* 156:1165-76 (1982); Dale et al., *J. Exp. Med.* 161:113-22 (1985)), brain (see, e.g., Bronze et al., *J. Immunol.* 151:2820-28 (1993)), muscle, kidney, and cartilage. Accordingly, the design of the multivalent immunogenic compositions described herein includes analysis of amino acid sequences in M proteins to determine if each M protein has five or more contiguous amino acids in common with one or more human proteins and which therefore could potentially induce antibodies that might bind to human tissue. Immunogenic peptides of M proteins and fusion polypeptides comprising the immunogenic peptides included in the immunogenic compositions described herein lack five or more contiguous amino acids that are identical to five or more contiguous amino acids of a known human protein.

Comparison of the amino acid sequences of M proteins with human proteins can be accomplished using one or more of the several alignment programs available to the person skilled in the art. Such alignment tools (which may also be useful for comparing nucleotide sequences, such as those encoding an M protein) include, without limitation, software programs such as BlastP, BLAST, tBLAST, and MegAlign. Other software programs are provided in the Lasergene bioinformatics computing suite (DNASTAR®Madison, Wis.); CLUSTALW program (see, e.g, Thompson et al., *Nucleic Acids Res.* 22:4673-80 (1991)); and "GeneDoc" (Nicholas et al., *EMBNEW News* 4:14 (1991)). References for algorithms such as ALIGN or BLAST may be found in, for example, Altschul, *J. Mol. Biol.* 219:555-565, 1991; and Henikoff and Henikoff, *Proc. Natl. Acad. Sci. USA* 89:10915-10919, 1992. Algorithms including the Align and BLAST algorithms are available at the NCBI website (see [online] Internet at ncbi.nlm.nih.gov/cgi-bin/BLAST). Default parameters may be used. Additional methods available in the art for comparing nucleotide or amino acid sequences and determining optimal alignment include methods described, for example, in Peruski and Peruski, *The Internet and the New Biology: Tools for Genomic and Molecular Research* (ASM Press, Inc. 1997); Wu et al. (eds.), "Information Superhighway and Computer Databases of Nucleic Acids and Proteins," in *Methods in Gene Biotechnology*, pages 123-151 (CRC Press, Inc. 1997); and Bishop (ed.), *Guide to Human Genome Computing,* 2nd Ed. (Academic Press, Inc. 1998).

A GAS immunogenic peptide that may be used in the multivalent vaccine compositions (i.e., multivalent immunogenic compositions) described herein comprises an immunogenic portion of a full-length GAS polypeptide and may comprise at least 25, 30, 35, 40, 45, 50, 55, or 60 or more contiguous amino acids (or any number of amino acids between 25-30, 30-35, 35-40, 40-45, 45-50, 40-55, or 55-60, or more than 60 contiguous amino acids) of the amino terminal portion of the mature polypeptide (i.e., the polypeptide from which the signal peptide sequence has been removed). In certain particular embodiments, the immunogenic peptide may comprise at least 25, 30, 35, 40, 45, 50, 55, or 60 or more contiguous amino acids from the amino terminal portion of an M protein or a Spa protein (or any number of amino acids between 25-30, 30-35, 35-40, 40-45, 45-50, 40-55, or 55-60, or more than 60 contiguous amino acids from the amino terminal portion of an M protein or a Spa protein). An immunogenic portion of a mature or full-length GAS polypeptide has one or more epitopes that induces an immune response, which includes production of antibodies that specifically bind to the immunogenic peptide, and to the immunogenic portion within the mature and full-length polypeptide, and to GAS bacteria that express the polypeptide. In more particular embodiments, an immunogenic peptide comprises at least 25 or at least 50 contiguous amino acids from the amino terminal portion of an M protein or a Spa protein. In certain specific embodiments, one or more immunogenic peptides comprise at least 25 contiguous amino acids from the amino terminal portion of an M protein or a Spa protein, which immunogenic peptide is present in duplicate and the duplicates are directly linked in tandem. In other words and by way of illustration, if the immunogenic region selected includes amino acid residues 1-25 of the amino terminal portion of an M protein or Spa protein, the immunogenic peptide in duplicate includes amino acid residues 1-25 linked in tandem to a second repeat of amino acids 1-25 (i.e., amino acid residue 25 of the first duplicate bonds directly to amino acid residue 1 of the second duplicate).

In one embodiment, the multivalent immunogenic compositions comprise immunogenic peptides that are representative (or obtained from, derived from) at least 30 different GAS serotypes. In more specific embodiments, one of the GAS serotypes represented in the immunogenic composition described herein is M4, and an immunogenic peptide comprises an amino acid sequence that includes at least 25 contiguous amino acids from the amino terminal portion of the M4 protein. In other certain embodiments, an immunogenic composition comprises at least 31 immunogenic peptides that are representative of at least 30 different GAS serotypes. In more particular embodiments, the amino acid sequence of each of the 31 immunogenic peptides is different and each comprises at least 25, 30, 35, 40, 45, 50, 55, or 60 or more contiguous amino acids (or any number of amino acids between 25-30, 30-35, 35-40, 40-45, 45-50, 40-55, or 55-60, or more than 60 contiguous amino acids) from the amino terminal portion of the M protein from one of GAS serotypes (1) M1; (2) M2; (3) M3; (4) M4; (5) M5; (6) M6; (7) M11; (8) M12; (9) M14; (10) M18; (11) M19; (12) M22; (13) M24; (14) M28; (15) M29; (16) M44; (17) M49; (18) M58; (19) M73; (20) M75; (21) M77; (22) M78; (23) M81; (24) M82; (25) M83; (26) M87; (27) M89; (28) M92; (29) M114; (30) M118, and (31) from the amino terminal portion of the Spa protein from GAS serotype, for example, such as GAS serotype M18. In another more specific embodiment, one or more of the immunogenic peptides comprises at least 25 contiguous amino acids in duplicate. In another specific embodiment one or more of the immunogenic peptides comprises at least 40 contiguous amino acids or at least 45 contiguous amino acids. In still another specific embodiment, one or more of the immunogenic peptides comprises at least at least 50 contiguous amino acids. As used herein, when referring to GAS bacteria according to serotype, the bacteria may be called, for example, GAS serotype 3, GAS M serotype 3, or GAS serotype M3. When referring to the M protein of a particular serotype, the designation of the GAS serotype from which the M protein is derived, such as M3, is typically followed by the word protein or immunogenic peptide depending on the context (i.e., M3 protein or M3 immunogenic peptide).

Accordingly, in other words, the embodiment of an immunogenic composition described above comprises at least the following immunogenic peptides: an immunogenic peptide comprising at least 25 contiguous amino acids from the amino terminal portion of the M protein from GAS serotype 1; an immunogenic peptide comprising at least 25 contiguous amino acids from the amino terminal portion of the M protein from GAS serotype 2; an immunogenic peptide comprising at least 25 contiguous amino acids from the amino terminal portion of the M protein from GAS serotype 3; an immunogenic peptide comprising at least 25 contiguous amino acids from the amino terminal portion of the M protein from GAS serotype 4; an immunogenic peptide comprising at least 25 contiguous amino acids from the amino terminal portion of the M protein from GAS serotype 5; an immunogenic peptide comprising at least 25 contiguous amino acids from the amino terminal portion of the M protein from GAS serotype 6; an immunogenic peptide comprising at least 25 contiguous amino acids from the amino terminal portion of the M protein from GAS serotype 11; an immunogenic peptide comprising at least 25 contiguous amino acids from the amino terminal portion of the M protein from GAS serotype 12; an immunogenic peptide comprising at least 25 contiguous amino acids from the amino terminal portion of the M protein from GAS serotype 14; an immunogenic peptide comprising at least 25 contiguous amino acids from the amino terminal portion of the M protein from GAS serotype 18; an immunogenic peptide comprising at least 25 contiguous amino acids from the amino terminal portion of the M protein from GAS serotype 19; an immunogenic peptide comprising at least 25 contiguous amino acids from the amino terminal portion of the M protein from GAS serotype 22; an immunogenic peptide comprising at least 25 contiguous amino acids from the amino terminal portion of the M protein from GAS serotype 24; an immunogenic peptide comprising at least 25 contiguous amino acids from the amino terminal portion of the M protein from GAS serotype 28; an immunogenic peptide comprising at least 25 contiguous amino acids from the amino terminal portion of the M protein from GAS serotype 29; an immunogenic peptide comprising at least 25 contiguous amino acids from the amino terminal portion of the M protein from GAS serotype 44; an immunogenic peptide comprising at least 25 contiguous amino acids from the amino terminal portion of the M protein from GAS serotype 49; an immunogenic peptide comprising at least 25 contiguous amino acids from the amino terminal portion of the M protein from GAS serotype 58; an immunogenic peptide comprising at least 25 contiguous amino acids from the amino terminal portion of the M protein from GAS serotype 73; an immunogenic peptide comprising at least 25 contiguous amino acids from the amino terminal portion of the M protein from GAS serotype 75; an immunogenic peptide comprising at least 25 contiguous amino acids from the amino terminal portion of the M protein from GAS serotype 77; an immunogenic peptide comprising at least 25 contiguous amino acids from the amino terminal portion of the M protein from GAS serotype 78; an immunogenic peptide comprising at least 25 contiguous amino acids from the amino terminal portion of the M protein from GAS serotype 81; an immunogenic peptide comprising at least 25 contiguous amino acids from the amino terminal portion of the M protein from GAS serotype 82; an immunogenic peptide comprising at least 25 contiguous amino acids from the amino terminal portion of the M protein from GAS serotype 83; an immunogenic peptide comprising at least 25 contiguous amino acids from the amino terminal portion of the M protein from GAS serotype 87; an immunogenic peptide comprising at least 25 contiguous amino acids from the amino terminal portion of the M protein from GAS serotype 89; an immunogenic peptide comprising at least 25 contiguous amino acids from the amino terminal portion of the M protein from GAS serotype 92; an immunogenic peptide comprising at least 25 contiguous amino acids from the amino terminal portion of the M protein from GAS serotype 114; an immunogenic peptide comprising at least 25 contiguous amino acids from the amino terminal portion of the M protein from GAS serotype 118; and an immunogenic peptide comprising at least 25 contiguous amino acids from the amino terminal portion of the Spa protein from a GAS serotype, for example, such as GAS serotype 18. In certain particular embodiments as described herein, each aforementioned immunogenic peptide may comprise at least 25, 30, 35, 40, 45, 50, 55, or 60 or more contiguous amino acids from the amino terminal portion of the respective M protein or Spa protein (or any number of amino acids between 25-30, 30-35, 35-40, 40-45, 45-50, 40-55, or 55-60, or more than 60 contiguous amino acids from the amino terminal portion of the respective M protein or Spa protein). In another more specific embodiment, one or more of the immunogenic peptides comprises at least 25 contiguous amino acids in duplicate. In another specific embodiment one or more of the immunogenic peptides comprises at least 40 contiguous amino acids or at least 45 contiguous amino acids. In still another specific embodiment, one or more of the immunogenic peptides comprises at least at least 50 contiguous amino acids.

In other certain embodiments, an immunogenic composition may comprise 32, 33, 34, 35, 36, 37, 38, 39, 40, 41, 42, 43, 44, 45, or more different immunogenic peptides. The different immunogenic peptides may include the 31 immunogenic peptides from the amino terminal portions of the M proteins from GAS M serotypes 1; 2; 3; 4; 5; 6; 11; 12; 14; 18; 19; 22; 24; 28; 29; 44; 49; 58; 73; 75; 77; 78; 81; 82; 83; 87; 89; 92; 114; 118, and Spa protein from the GAS serotype 18 (as described above) and further comprise immunogenic peptides from the amino terminal portions of M proteins from at least one additional, different GAS serotype or subtype and/or one or more additional, different immunogenic peptide from the amino terminal portion of a Spa protein. Selection of additional immunogenic peptides may be informed by epidemiology data; lack of shared identity of 5 or more contiguous amino acids of the GAS protein with a human protein; immunogenicity, bactericidal, and/or protection data, including the capability of the one or more additional immunogenic peptides to increase the number of non-represented GAS serotypes recognized by antibodies produced in response to immunization with such an immunogenic composition.

As described herein and known to a person skilled in the art, the amino terminal portion of M proteins and Spa proteins comprise the regions of M proteins and Spa proteins that have one or more immunogenic epitopes which evoke a protective immune response but do not induce antibodies that cross-react with proteins expressed by human cells and tissues. As used herein the amino terminal portion of an M protein or a Spa protein refers to the mature protein, which is the expressed protein lacking the signal peptide sequence. As is well understood in the art, polypeptides that are secreted or are membrane bound proteins are translocated through or to the membrane, respectively, by a translocation apparatus that interacts with a signal peptide at the amino terminal end of a nascent polypeptide. In bacteria, a signal peptide sequence is typically cleaved from a nascently translated polypeptide in vivo by a bacterial protease to form the mature polypeptide. Accordingly, unless specified otherwise, a description herein of an immunogenic peptide as an immunogenic peptide comprising the amino acid sequence of residues 1-50 of an M protein (for example), residue 1 is at the amino terminus of the M protein in the absence of the signal peptide sequence. Exemplary amino acid sequences for immunogenic peptides are provided in SEQ. ID NOS:29-59 (see Sequence Listing and Table 1).

The term "amino terminal portion" of an M protein or a Spa protein is readily understood by a person having ordinary skill in the art as the portion or region of an polypeptide located in the amino terminal half of the polypeptide. The immunogenic peptides described herein that comprise amino acids from the amino terminal portion of an M protein or a Spa protein may, but not necessarily, comprise at least 25 contiguous amino acids from the amino terminal end of the respective M protein or Spa protein (i.e., amino acids 1-25 of the mature polypeptide). In other instances, an immunogenic peptide may comprise at least 25 contiguous amino acids derived from the amino terminal portion of an M protein or Spa protein that lack one or more amino acids located at the amino terminus of the mature protein (e.g., amino acids 2-26, 3-27, 4-28 and the like of the mature polypeptide). In other embodiments, and by way of example, the at least 25 contiguous amino acids may be derived from the amino terminal portion of the M protein or Spa protein that begins at amino acid position 5, 6, 7, 8, 9, 10, 11, 12, 13, 14, 15, 16, 17, 18, 19, 20, 21, 22, 23, 24, or 25. As described herein, the amino acid sequence of each immunogenic peptide is selected, at least in part, on the basis of the presence of at least one immunogenic epitope and the lack of at least five contiguous amino acids that are identical to at least five contiguous amino acids present in a known human protein.

In one embodiment, the immunogenic composition comprising at least 31 different immunogenic peptides contains each of the individual immunogenic peptides as separate peptides. In certain embodiments, the immunogenic composition may comprise 31, 32, 33, 34, 35, 36, 37, 38, 39, 40, 41, 42, 43, 44, 45, or more different immunogenic peptides and contains each of the individual immunogenic peptides as a separate peptide. Each of these immunogenic peptides may each be chemically synthesized or may be recombinantly produced according to techniques and methods described in greater detail herein and in the art. The individual peptides are then combined together and formulated in an immunogenic composition. Also as described in greater detail herein, the immunogenic compositions may comprise one or more pharmaceutically suitable excipients, and may further comprise one or more pharmaceutically suitable adjuvants. In still another embodiment, the immunogenic compositions comprise the at least 31 different immunogenic peptides as a combination of individual immunogenic peptides, dimeric peptides, and/or trimeric peptides.

In still other embodiments, at least four different immunogenic peptides may be linked together in tandem to form a fusion polypeptide for inclusion in an immunogenic composition. In certain embodiments, the immunogenic composition comprising at least 31 different immunogenic peptides (for example, 31, 32, 33, 34, 35, 36, 37, 38, 39, 40, 41, 42, 43, 44, 45, or more different immunogenic peptides) may include at least one, two, three, four, five, six, seven, or more fusion polypeptides, wherein each fusion polypeptide comprises at least four different immunogenic peptides linked together in tandem. In more particular embodiments, one or more fusion polypeptides included in an immunogenic composition may comprise 4, 5, 6, 7, 8, 9, 10, 11, 12, 13, 14, or 15, or more individual immunogenic peptides linked in tandem. In more specific embodiments, each fusion polypeptide comprising different immunogenic peptides linked in tandem and that is used in the immunogenic compositions described herein comprises at least 6, 7, 8, 9, or 10 different immunogenic peptides. In even more specific embodiments described herein, an immunogenic composition comprises at least 31 different immunogenic peptides, each from the amino terminal portion of a GAS M protein or Spa protein, and at least six, seven, eight or nine different immunogenic peptides are linked together in a manner that provides four fusion polypeptides. In still another specific embodiment, an immunogenic composition comprises at least 31 different immunogenic peptides, each from the amino terminal portion of a GAS M protein or Spa protein, and seven or eight different immunogenic peptides are linked together in tandem per fusion polypeptide in a manner that provides four fusion polypeptides. Stated another way, each of the at least 31 different immunogenic peptides is included in one of these four fusion polypeptides.

In more specific embodiments, an immunogenic composition comprises at least 31 different immunogenic peptides (e.g., immunogenic peptides from the amino terminal portions of the M proteins from GAS M serotypes 1; 2; 3; 4; 5; 6; 11; 12; 14; 18; 19; 22; 24; 28; 29; 44; 49; 58; 73; 75; 77; 78; 81; 82; 83; 87; 89; 92; 114; 118, and Spa protein from GAS serotype 18), wherein at least six, seven, eight, or nine different immunogenic peptides are linked together in tandem to form at least four fusion polypeptides. In one particular embodiment, each of the four fusion polypeptides comprises at least 7 or at least 8 different immunogenic peptides. In one embodiment, the immunogenic composition comprises four fusion polypeptides (which for convenience may be called a first fusion polypeptide, a second fusion polypeptide, a third fusion polypeptide, and a fourth fusion polypeptide) and each fusion polypeptide comprises 7 or 8 different immunogenic peptides independently selected from the at least 31 different immunogenic peptides. Which immunogenic peptides are included on each of the first, second, third, and fourth fusion polypeptides and the order with which the immunogenic peptides are linked may be readily determined by a person skilled in the art using methods and techniques described herein and routinely practiced in the art and does not require undue empirical, trial and error analysis to ensure optimization of the immunogenicity of each polypeptide. To determine that the amino acids located at the junction where two different immunogenic peptides are tandemly linked does not introduce a contiguous 5-amino acid sequence that shares identity with a human protein, the amino acid sequence of each fusion polypeptide is compared with the sequences of human proteins available in databases described herein and known to the person skilled in the art.

Fusion polypeptides comprising three or more different immunogenic peptides from the amino terminal portions of the M proteins and Spa proteins from GAS serotypes are constructed so that the immunogenic peptide located at the amino terminal end is repeated (i.e., duplicated) at the carboxy terminal end of the fusion polypeptide. In the absence of a duplicate immunogenic peptide at the carboxy terminal end of the fusion polypeptide, the immunogenicity of the penultimate and carboxy terminal peptide may be reduced or compromised. Without wishing to be bound by theory, repetition of the amino terminal peptide at the carboxy terminal end preserves the immunogenicity of all peptides included in the fusion protein and reduces or abrogates the need for inclusion of a non-GAS carrier protein, such as tetanus toxoid, keyhole limpet hemocyanin, or other protein or protein fragment, used in the art to enhance an immune response to an antigen of interest. See U.S. Pat. Nos. 6,716,433 and 7,402,316.

As described herein, the amino acid sequences of M proteins and Spa proteins are readily available in the art. Databases, such as provided at the CDC emm typing center website, may be accessed to determine the variability in the amino acid sequences within an M protein from a GAS serotype (referred to herein and in the art as GAS subtypes) or within a Spa protein from a GAS serotype. Alignment tools for comparison of the amino terminal portions of M proteins (or Spa proteins) can be used to identify amino acid residues within the amino terminal portion that may be variable. The amino acid sequences of the immunogenic peptides and fusion polypeptides described herein are exemplary, and immunogenic peptides and fusion polypeptides useful for inducing an immune response against GAS may include substitutions, insertions, and deletions of one or more amino acids that do not adversely affect (decrease or reduce in a statistically significant manner or biologically or clinical significant manner) the immunogenicity of the immunogenic peptide or fusion polypeptide. Immunogenicity of a variant peptide or variant fusion polypeptide that is substantially similar in a statistically, biologically, or clinically significant manner to the immunogenicity of an immunogenic peptide or fusion polypeptide, respectively, described herein is desired. Exemplary amino acid sequences for immunogenic peptides from the amino terminal portions of the M proteins from GAS M serotypes 1; 2; 3; 4; 5; 6; 11; 12; 14; 18; 19; 22; 24; 28; 29; 44; 49; 58; 73; 75; 77; 78; 81; 82; 83; 87; 89; 92; 114; 118, and Spa protein from GAS serotype 18 are provided in Table 1.

Also provided herein in more specific embodiments are immunogenic compositions that may be used in particular geographic regions. By way of example, provided herein in certain embodiments are immunogenic compositions that comprise at least 23 different immunogenic peptides (e.g., immunogenic peptides from the amino terminal portions of the M proteins from GAS M serotypes 1; 2; 3; 4; 5; 6; 11; 12; 14; 18; 19; 22; 24; 28; 29; 44; 58; 73; 75; 77; 78; 89; 118, and Spa protein from GAS serotype 18), wherein at least six, seven, eight, or nine different immunogenic peptides are linked together in tandem to form at least three or at least four fusion polypeptides. In one particular embodiment, an immunogenic composition comprises each of three fusion polypeptides that each comprises at least 7 or at least 8 different immunogenic peptides. In one embodiment, the immunogenic composition comprises three fusion polypeptides (which for convenience may be called a first fusion polypeptide, a second fusion polypeptide, and a third fusion polypeptide) and each fusion polypeptide comprises 7 or 8 different immunogenic peptides. This exemplary immunogenic composition comprises GAS serotypes that are more prevalent in GAS infections in North America than in other global regions, such as Europe. GAS M serotypes, such as 49, 81, 82, 83, 87, 92 and 114, are identified in Europe more frequently than in North America as the cause of a GAS infection.

In certain embodiments, an immunogenic peptide or fusion polypeptide described herein includes immunogenic peptide or fusion polypeptide species, respectively, that have one or more amino acid substitutions, insertions, or deletions (also called herein a variants). Immunogenic peptide species or a fusion polypeptide species comprising the immunogenic peptides described herein includes immunogenic peptide species and fusion polypeptide species, respectively, that have one or more amino acid substitutions, insertions, or deletions (also called herein a variant). Immunogenic peptide variants include those that comprise an amino acid sequence different from an exemplary amino acid sequence described herein of the immunogenic peptide and that comprise the amino acid sequence (at least 25 contiguous amino acids of the amino terminal portion of a Spa protein or M protein) of a different subtype of the same respective GAS serotype (see, e.g., Dale et al., *Clin. Diagn. Lab. Immunol.* 12:833-36 (2005); Facklam et al., *Emerg. Infect. Dis.* 5:247-53 (1999)). Fusion polypeptide variants include species comprising at least one immunogenic peptide variant. Amino acid sequences of M protein subtypes are available in public databases, including the CDC emm typing center website (supra).

Immunogenic peptide variants and fusion polypeptide variants also include those that have amino acid substitutions, deletions or insertions, which may be introduced during chemical synthesis or recombinant production, whichever method is used to produce the particular immunogenic peptide or fusion polypeptide. Immunogenic peptide variants and fusion polypeptide variants useful for inducing an immune response against GAS may also include substitutions, insertions, and deletions of one or more amino acids of the amino acid sequences described herein and that do not adversely affect or alter (decrease or reduce) the immunogenicity of the immunogenic peptide or fusion polypeptide in a statistically, biologically, or clinically significant manner. Stated another way, a variant of an immunogenic peptide or of a fusion polypeptide described herein retains immunogenicity exhibited by the immunogenic peptide or fusion polypeptide, respectively. As described herein, retention of immunogenicity includes the capability to evoke an immune response against GAS, such as production of antibodies that specifically bind to the cognate immunogenic peptide and/or fusion polypeptide, cognate full-length or mature M protein or Spa protein (either isolated or present on the cell surface of GAS bacteria), and which antibodies include those with bactericidal and phagocytic activity.

In general, an amino acid substitution that may be included in an immunogenic peptide or a fusion polypeptide is a conservative substitution. Conservative substitutions of amino acids are well known and may occur naturally in an M protein or Spa polypeptide or may be introduced when the peptide or fusion polypeptide is recombinantly produced. A variety of criteria understood by a person skilled in the art indicate whether an amino acid that is substituted at a particular position in an immunogenic peptide or fusion polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the peptide or polypeptide to the sequence of a second peptide or polypeptide, respectively, using any one of the algorithms, such as Align or the BLAST algorithm, or other algorithms described herein and practiced in the art.

Amino acid substitutions, deletions, and additions may be introduced into an immunogenic peptide or fusion polypeptide during chemical synthesis of the polynucleotide that encodes the peptide or fusion polypeptide. Alternatively, amino acid substitutions, deletions, and additions may be introduced into an immunogenic peptide or fusion polypeptide recombinantly using well-known and routinely practiced mutagenesis methods (see, e.g., Sambrook et al. *Molecular Cloning: A Laboratory Manual,* 3d ed., Cold Spring Harbor Laboratory Press, NY 2001)). Oligonucleotide-directed site-specific (or segment specific) mutagenesis procedures may be employed to provide an altered polynucleotide that has particular codons altered according to the substitution, deletion, or insertion desired. Alternatively, random mutagenesis techniques, such as alanine scanning mutagenesis, error prone polymerase chain reaction mutagenesis, and oligonucleotide-directed mutagenesis may be used to prepare immunogenic peptide and fusion polypeptide variants (see, e.g., Sambrook et al., supra). An immunogenic peptide variant or a fusion polypeptide variant includes an immunogenic peptide or fusion polypeptide, respectively, that has at least 85%, 90%, 92%, 95%, 97%, 98%, or 99% amino acid sequence identity to any of the exemplary immunogenic peptide and fusion polypeptide amino acid sequences provided herein, including in the sequence listing (for example, fusion polypeptides represented by SEQ ID NOS:1-12, and immunogenic peptides represented by SEQ ID NOS:29-59). Percent identity of one amino acid sequence to one or more additional sequences may be determined using any one of the alignment tools described herein and used in the art.

Given the description in the art and herein regarding regions of M proteins and Spa proteins that exhibit immunogenic activity and lack undesirable epitopes that induce antibodies that cross-react with proteins expressed on human cells, persons skilled in the art can readily determine which amino acids in the amino terminal portions of M proteins and Spa proteins may be more amenable to alteration (i.e., substitution, deletion, or addition of one or more amino acids) and which amino acids may not be amenable to change. Also given the description herein and given the many molecular biology, protein expression, and protein isolation techniques and methods routinely practiced in the art for introducing mutations in a peptide or polypeptide, isolating these peptides and polypeptides and variants thereof, and analyzing same, the desired immunogenicity can be made readily and without undue experimentation. Retention of immunogenicity includes the capability to evoke an immune response against GAS, such as production of antibodies that specifically bind to the cognate immunogenic peptide and/or fusion polypeptide, cognate mature M protein or Spa protein (either isolated or present on the cell surface of GAS bacteria), or cognate full-length M protein or Spa protein, and which antibodies include those with bactericidal and phagocytic activity.

Assays for assessing whether a variant of an immunogenic peptide of an M protein or of a Spa protein, or a fusion polypeptide comprising the immunogenic peptides, folds into a conformation comparable to the non-variant peptide or fusion polypeptide include, for example, the ability of the peptide or fusion polypeptide to react with mono- or polyclonal antibodies that are specific for native or unfolded epitopes, the retention of ligand-binding functions, and the sensitivity or resistance of the mutant peptide or fusion polypeptide to digestion with proteases (see Sambrook et al., supra). Immunogenic peptide variants and fusion polypeptide variants as described herein can be identified, characterized, and/or made according to these methods described herein or other methods known in the art, which are routinely practiced by persons skilled in the art.

Variants of individual immunogenic peptides and of fusion polypeptides comprising immunogenic peptides, can be prepared without altering a biological activity of the resulting molecule (i.e., without altering one or more immunogenic activities in a statistically significant, clinically significant, or biologically significant manner). As described in greater detail herein, for example, such substitutions are generally made by interchanging an amino acid with another amino acid that is included within the same group, such as the group of polar residues, charged residues, hydrophobic residues, and/or small residues, and the like. The effect of any amino acid substitution may be determined empirically merely by testing the resulting modified peptide or fusion polypeptide for the ability to function in a biological assay, or to bind to a cognate ligand or target molecule, such as a monoclonal or polyclonal antibody.

Exemplary Anti-GAS Immunogenic Composition Comprising Four Fusion Polypeptides

In one particular embodiment, an immunogenic composition useful for inducing an immune response against GAS comprises 31 different immunogenic peptides, and each immunogenic peptide is incorporated into one of four fusion polypeptides. Each immunogenic peptide is from the amino terminal portion of the M protein from one of GAS M serotypes 1; 2; 3; 4; 5; 6; 11; 12; 14; 18; 19; 22; 24; 28; 29; 44; 49; 58; 73; 75; 77; 78; 81; 82; 83; 87; 89; 92; 114; 118, or from the amino terminal portion of Spa protein from GAS serotype 18. Three fusion polypeptides (for convenience, called a first, second, and third fusion polypeptide, respectively) each comprise at least 8 different immunogenic peptides linked in tandem, and the fourth fusion polypeptide comprises at least 7 different immunogenic peptides linked in tandem. In a particular embodiment, the first fusion polypeptide comprises 8 immunogenic peptides, which are different, and each immunogenic peptide comprises at least 25 contiguous amino acids from the amino terminal portion of the M protein from one of GAS M serotypes 1, 2, 3, 6, 12, 18, 28, and from the amino terminal portion of the Spa protein from GAS serotype 18. Stated another way, a first fusion polypeptide comprises at least 8 different immunogenic peptides linked in tandem, and each immunogenic peptide comprises at least 25 contiguous amino acids from the amino terminal portion of one of M1 protein, M2 protein, M3 protein, M6 protein, M12 protein, M18 protein, M28 protein, and Spa 18 protein (i.e., the fusion polypeptide therefore comprises an immunogenic peptide from the amino terminal portion of M1 protein, an immunogenic peptide from the amino terminal portion of M2 protein, an immunogenic peptide from the amino terminal portion of M3 protein etc.). One of the immunogenic peptides is repeated at each of the amino and carboxy terminal ends of the fusion polypeptide. In a more particular embodiment, the first fusion polypeptide comprises duplicates (repeats) of the immunogenic peptide comprising at least 25 contiguous amino acids from the amino terminal portion of the M protein from GAS serotype 1; one duplicate is located at the amino terminal end of the fusion polypeptide and the second duplicate is located at the carboxy terminal end of the fusion polypeptide.

The second fusion polypeptide comprises 8 immunogenic peptides, which are different, and each immunogenic peptide comprises at least 25 contiguous amino acids from the amino terminal portion of the M protein from one of GAS M serotypes 4, 5, 11, 14, 19, 24, 29, and 75. Stated another way and similar to the description of the first fusion polypeptide, the second fusion polypeptide comprises at least 8 different immunogenic peptides linked in tandem, and each immunogenic peptide comprises at least 25 contiguous amino acids from the amino terminal portion of one of M4 protein, M5 protein, M11 protein, M14 protein, M19 protein, M24 protein, M29 protein, and M75 protein. One of the immunogenic peptides is repeated at each of the amino and carboxy terminal ends of the second fusion polypeptide. In a more particular embodiment, the second fusion polypeptide comprises duplicates (repeats) of the immunogenic peptide comprising at least 25 contiguous amino acids from the amino terminal portion of the M protein from GAS serotype 4; one duplicate is located at the amino terminal end of the fusion polypeptide and the second duplicate is located at the carboxy terminal end of the fusion polypeptide.

In certain embodiments, the third fusion polypeptide comprises 8 immunogenic peptides, which are different, and each immunogenic peptide comprises at least 25 contiguous amino acids from the amino terminal portion of the M protein from one of GAS M serotypes 22, 44, 58, 73, 77, 78, 89, and 118. Stated another way and as above, a third fusion polypeptide comprises at least 8 different immunogenic peptides linked in tandem, and each immunogenic peptide comprises at least 25 contiguous amino acids from the amino terminal portion of one of M22 protein, M44 protein, M58 protein, M73 protein, M77 protein, M78 protein, M89 protein, and M118 protein. One of the immunogenic peptides is repeated at each of the amino and carboxy terminal ends of the third fusion polypeptide. In a more particular embodiment, the third fusion polypeptide comprises duplicates (repeats) of the immunogenic peptide comprising at least 25 contiguous amino acids from the amino terminal portion of the M protein from GAS serotype 77; one duplicate is located at the amino terminal end of the fusion polypeptide and the second duplicate is located at the carboxy terminal end of the fusion polypeptide.

The fourth fusion polypeptide comprises 7 immunogenic peptides, which are each different, and each immunogenic peptide comprises at least 25 contiguous amino acids from the amino terminal portion of the M protein from one of GAS M serotypes 49, 81, 82, 83, 87, 92, and 114. Stated another way and as above, a fourth fusion polypeptide comprises at least 8 different immunogenic peptides linked in tandem, and each immunogenic peptide comprises at least 25 contiguous amino acids from the amino terminal portion of one of M49 protein, M81 protein, M82 protein, M83 protein, M87 protein, M92 protein, and M114 protein. One of the immunogenic peptides is repeated at each of the amino and carboxy terminal ends of the fourth fusion polypeptide. In a more particular embodiment, the fourth fusion polypeptide comprises duplicates (repeats) of the immunogenic peptide comprising at least 25 contiguous amino acids from the amino terminal portion of the M protein from GAS serotype 83; one duplicate is located at the amino terminal end of the fusion polypeptide and the second duplicate is located at the carboxy terminal end of the fusion polypeptide.

Each immunogenic peptide in each of the first, second, third, and fourth fusion polypeptides may comprise independently at least 25, 30, 35, 40, 45, 50, 55, or 60 or more contiguous amino acids from the amino terminal portion of the respective M protein or Spa protein (or any number of amino acids between 25-30, 30-35, 35-40, 40-45, 45-50, 40-55, or 55-60, or more than 60 contiguous amino acids from the amino terminal portion of the respective M protein or Spa protein). In another more specific embodiment, one or more of the immunogenic peptides comprises at least 25 contiguous amino acids in duplicate and each duplicate is in tandem (i.e., not separated by one or more immunogenic peptides from a different M or Spa protein of the fusion protein). In another specific embodiment one or more of the immunogenic peptides comprises at least 40 contiguous amino acids or at least 45 contiguous amino acids from the amino terminal portion of the respective M protein or Spa protein. In still another specific embodiment, one or more of the immunogenic peptides comprises at least 50 contiguous amino acids from the amino terminal portion of the respective M protein or Spa protein.

In certain specific embodiments, as discussed herein, the immunogenic peptides may be derived from subtypes of the respective M protein. For example, in certain specific embodiments, the immunogenic peptide from the M protein of GAS serotype 3 is from GAS serotype 3.1. In other specific embodiments, the immunogenic peptide from the M protein of GAS serotype 6 is from GAS serotype 6.4. In still another specific embodiment, the immunogenic peptide from the M protein of GAS serotype 5 is from GAS serotype 5.0 (parent subtype). In a certain particular embodiment, the immunogenic peptide from the M protein of GAS serotype 14 is from GAS serotype 14.3. In yet another specific embodiment, the immunogenic peptide from the M protein of GAS serotype 29 is from GAS serotype 29.2. In still yet another specific embodiment, the immunogenic peptide from the M protein of GAS serotype 49 is from GAS serotype 49.1. In still another specific embodiment, the immunogenic peptide from the M protein of GAS serotype 83 is from GAS serotype 83.1. If no subtype is designated, the M protein is derived from the subtype considered in the art as the "parent" subtype, such as, by way of illustration, M12.0, M18.0, M28.0, and the like.

In a more specific embodiment, the first fusion polypeptide comprising eight immunogenic peptides, which immunogenic peptides are independently from the amino terminal portion of the M protein from one of GAS M serotypes 1, 2, 3, 6, 12, 18, 28, and from the amino terminal portion of the Spa protein from GAS serotype 18 as described above, are linked in tandem in the following order from amino terminal to carboxy terminal: M1, M3.1, M6.4, M2, M18, M28, M12, Spa, and M1. Each of the M1, M18, M28, M12, and Spa immunogenic peptides comprises amino acid residues 1-50 from each of the respective mature M proteins or Spa protein. The immunogenic peptide representing the GAS serotype 3.1 comprises amino acid residues at positions 22-71 of the mature M3.1 protein. Each of the immunogenic peptides of the M3.1 protein and the M6.4 protein include amino acid residues 1-25 of the respective mature M protein linked directly in tandem to a duplicate (i.e., repeat) of residues 1-25. The immunogenic peptide of the M2 protein include amino acid residues 2-26 of the respective mature M protein linked directly in tandem to a duplicate (i.e., repeat) of residues 2-26. The second fusion polypeptide comprising eight immunogenic peptides, which immunogenic peptides are independently from the amino terminal portion of the M protein from one of GAS M serotypes 4, 5, 11, 14, 19, 24, 29, and 75, are linked in tandem in the following order from amino terminal to carboxy terminal: M4, M5.0, M11, M75, M19, M29.2, M14.3, M24, and M4. Each of the M4, M11, M75, M29.2, M14.3, and M24 immunogenic peptides comprises amino acid residues 1-50 from the amino terminal portion of the respective mature M protein. Each of the immunogenic peptides of the M5.0 protein and the M19 protein includes amino acid residues 1-25 of the respective mature M protein linked directly in tandem to a duplicate (i.e., repeat) of residues 1-25. The third fusion polypeptide comprising eight immunogenic peptides, which immunogenic peptides are independently from the amino terminal portion of the M protein from one of GAS M serotypes 22, 44, 58, 73, 77, 78, 89, and 118, are linked in tandem in the following order from amino terminal to carboxy terminal: M77, M22, M73, M89, M58, M44, M78, M118, and M77. Each of these M protein immunogenic peptides comprises amino acid residues 1-50 at the amino terminal portion of the respective mature M proteins. The fourth fusion polypeptide comprising seven immunogenic peptides, which immunogenic peptides are independently from the amino terminal portion of the M protein from one of GAS M serotypes 49, 81, 82, 83, 87, 92, and 114, are linked in tandem in the following order from amino terminal to carboxy terminal: M83.1, M82, M81, M87, M49.1, M92, M114, and M83.1. Each of these M protein immunogenic peptides comprises amino acid residues 1-50 at the amino terminal portion of the respective mature M proteins. See also FIG. 1.

Exemplary amino acid sequences for each of the specific embodiments of a first, second, third, and fourth fusion polypeptides are provided in SEQ ID NOS: 1, 2, 3, and 4, respectively. Any of the immunogenic peptides, dimeric peptides, and fusion polypeptides, including the exemplary fusion polypeptides described herein may further comprise a heterologous peptide or polypeptide at either the amino or carboxy terminus or both to facilitate expression, solubilization, stabilization, isolation, and/or detection. For example, when immunogenic peptides, dimeric peptides, or fusion polypeptides are produced according to recombinant methods, an initiating methionine residue at the amino terminus is typically included (see, for example, SEQ ID NOS: 5, 6, 7, and 8 corresponding to the first, second, third, and fourth fusion polypeptides, respectively). Examples of amino acid sequences that may be added at either the amino or carboxy terminal ends (also called polypeptide tags) to facilitate isolation, solubilization, stabilization, and/or detection of the peptide or fusion polypeptide include polyhistidine tags (e.g., 6-His tag), glutathione-S-transferase (GST), FLAG® epitope tag (DYKDDDDK, SEQ ID NO:60), beta-galactosidase, alkaline phosphatase, chitin binding protein (CBP), XPRESS™ epitope tag (DLYDDDDK, SEQ ID NO:61; Invitrogen Life Technologies, Carlsbad, Calif.) maltose binding protein (MBP), thioredoxin (a solubilization tag), and poly(NANP) (a solubilization tag) (see, e.g., U.S. Pat. No. 5,011,912; Hopp et al., (*Bio/Technology* 6:1204 (1988)). If the peptide, dimeric peptide, or fusion polypeptide is recombinantly produced, the affinity sequence may be supplied by a vector, such as, for example, a hexa-histidine tag that is provided in pBAD/His (Invitrogen). Alternatively, the affinity sequence may be added either synthetically or engineered into the primers used to recombinantly generate the nucleic acid coding sequence (e.g., using the polymerase chain reaction). Additional methods and techniques for using polypeptide tags are routinely practiced in the art and available from commercial vendors who manufacture systems and kits for adding tags to a peptide or polypeptide of interest. By way of illustration, the first, second, third, and fourth fusion polypeptides may incorporate a polyhistidine tag to facilitate purification (see, e.g., SEQ ID NOS:9-12, respectively).

A fusion polypeptide variant includes a fusion polypeptide, that has at least 85%, 90%, 92%, 95%, 97%, 98%, or 99% amino acid sequence identity to any of the exemplary fusion polypeptide amino acid sequences provided herein, including in the sequence listing (e.g., SEQ ID NOS:1-12). Fusion polypeptides useful for inducing an immune response against GAS may include substitutions, insertions, and deletions of one or more amino acids of any of the aforementioned amino acid sequences and that do not adversely affect or alter (decrease or reduce) the immunogenicity of the fusion polypeptide in a statistically, biologically, or clinically significant manner Stated another way, a variant of a fusion polypeptide described herein retains immunogenicity exhibited by the parent or non-variant fusion polypeptide. As described herein, retention of immunogenicity includes the capability to evoke an immune response against GAS, such as production of antibodies that specifically bind to the cognate immunogenic peptide and/or fusion polypeptide, cognate mature or full-length M protein or Spa protein (either isolated or present on the cell surface of GAS bacteria), and which antibodies include those with bactericidal and phagocytic activity.

As described in the Examples, immunization of animals with an immunogenic composition comprising each of the above described exemplary first, second, third, and fourth fusion polypeptides evoked production of bactericidal antibodies that specifically bound to each GAS serotype represented by an M protein immunogenic peptide and Spa immunogenic peptide (i.e., GAS serotypes 1; 2; 3; 4; 5; 6; 11; 12; 14; 18; 19; 22; 24; 28; 29; 44; 49; 58; 73; 75; 77; 78; 81; 82; 83; 87; 89; 92; 114; 118). In addition, antisera from immunized animals was bactericidal against more than half of GAS serotypes for which an immunogenic peptide from an M protein or Spa protein was not represented in any one of the fusion polypeptides. This improved efficacy is greater than a person skilled in the art may have predicted on the basis of previously described results with other multivalent compositions. When compared with a previously described 26-valent vaccine (see, e.g., U.S. Pat. No. 7,270,827; Hu et al., supra), the particular combination of immunogenic peptides described herein recognized significantly more non-vaccine GAS serotypes (see Example 4). Serotypes represented in the 30-valent immunogenic composition described herein that were not included in the 26-valent composition include GAS M serotypes 4, 29, 58, 44, 49, 73, 78, 81, 82, 83, 87, 118.

Serotypes in the 26-valent composition not represented by immunogenic peptides in the composition described herein include GAS M serotypes 1.2, 13, 33, 43, 59, 76, and 101.

Two different immunogenic peptides may be directly linked in tandem to form dimeric peptides (also called dipeptides), which in certain embodiments, are useful in methods for detecting antibodies are specific for an immunogenic peptide. Dimeric peptides may be recombinantly produced as described herein and in the art according to methods and techniques routinely used and practiced in the art (see, e.g., Hu et al., supra). Alternatively, dimeric peptides may be chemically synthesized according to methods described herein and in the art. Dimeric peptides may be comprised of any two different immunogenic peptides described herein. By way of example, a dimeric peptide (which includes an immunogenic dimeric peptide), is composed of two immunogenic peptides and each peptide of the dimeric peptide is different and comprises at least 25 contiguous amino acids of the amino terminal portion of a different M protein or a Spa protein, wherein each different M protein is independently selected from the M protein of GAS serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18.

Production of Immunogenic Peptides and Fusion Polypeptides

Provided herein are immunogenic peptides comprising at least 25 contiguous amino acids from the amino terminal portion of an M protein or Spa protein from different serotypes of group A *streptococcus* and fusion polypeptides comprising these immunogenic peptides. Each of the immunogenic peptides, immunogenic dimeric peptides (i.e., polypeptides comprising two different immunogenic peptides), and fusion polypeptides may be produced recombinantly or may be chemically synthesized. Alternatively, polynucleotides encoding individual immunogenic peptides, immunogenic dimeric peptides, and fusion polypeptides may be constructed by recombinant methods or chemically synthesized, and the constructed or synthesized polynucleotides may be incorporated into expression vectors for production of the peptide, dimeric peptide, or fusion polypeptide in a host cell into which the expression vector has been introduced.

Peptides and polypeptides may be chemically synthesized by manual techniques or by automated procedures. Equipment for automated synthesis of polypeptides is commercially available from suppliers such as Perkin-Elmer, Inc. and Applied BioSystems Division (Foster City, Calif.), and may be operated according to the manufacturer's instructions. By way of example, solid phase polypeptide synthesis has been performed since the early 1960's (see, e.g., Merrifield, *J. Am. Chem. Soc.* 85:2149-2154 (1963)). Numerous improvements to synthesis methods have been developed, and many methods have been automated and chemistries have been developed to protect the terminal ends and other reactive groups (see, e.g., Geysen et al., *J. Immun. Meth.* 102:259-274 (1987); Miranda et al., *Proc. Natl. Acad. Sci. USA* 96:1181-86 (1999); Frank et al., *Tetrahedron* 44:6031-6040 (1988); Hyrup et al., *Bioorg. Med. Chem.* 4:5-23 (1996); Perry-O'Keefe et al., *Proc. Natl. Acad. Sci. USA* 93:14670-675 (1996); Schnölzer, et al. *Int J. Pept. Protein Res.* 40, 180-193 (1992); Hackeng et al., *Proc. Natl. Acad. Sci. USA* 94:7845-50 (1997); Creighton, T. E. Protein: Structures and Molecular Properties, pp. 55-60, W. H. Freeman and Co., New York, N.Y. (1984)). Equipment for performing automated synthesis is available from a variety of manufacturers. Synthesized peptides, dimeric peptides, and fusion polypeptides may be obtained from any number of different custom peptide synthesizing manufacturers. If required, synthesized peptides or polypeptides may be purified using preparative reverse phase chromatography, partition chromatography, gel filtration, gel electrophoresis, or ion-exchange chromatography or other methods used in the art.

Polynucleotides may also be chemically synthesized or may be constructed by recombinant methods familiar to a person skilled in the art. Polynucleotides can also be synthesized using an automatic synthesizer. The nucleotide sequence can be designed with the appropriate codons for the particular amino acid sequence desired. In general, preferred codons may be selected for the intended host in which the nucleotide sequence will be expressed. One recombinant method of preparing a polynucleotide includes assembly from overlapping oligonucleotides prepared by standard methods to provide a complete coding sequence (see, e.g., Au et al., *Biochem. Biophys. Res. Commun.* 248:200-203 (1998); Stemmer et al., *Gene* 164:49-53 (1995); Ausubel et al. (eds.), *Current Protocols in Molecular Biology*, (Greene Publ. Assoc. Inc. & John Wiley & Sons, Inc., 1993)); Sambrook et al., et al. *Molecular Cloning: A Laboratory Manual,* 3rd Ed., (Cold Spring Harbor Laboratory 2001; and elsewhere). Methods for purifying polynucleotides after either chemical synthesis or recombinant synthesis are known to persons skilled in the art (see, e.g., Ausubel et al., supra; Sambrook et al., supra).

Chemical synthesis of oligonucleotides for primers and probes has long been practiced in the art (see, e.g., Letsinger et al., *J. Am. Chem. Soc.* 98:3655-61 (1976); Matteucci et al., *J. Am. Chem. Soc.* 103:3185-9 (1981)). Improved methods for synthesizing oligonucleotides and polynucleotides, which provide more rapid results, greater yields, and longer polynucleotides, have since been developed and automated (see, e.g., Gao et al., *Biopolymers* 73:579-96 (2004); Mueller et al., *Chem. Biol.* 16:337-47 (2009); Lee et al., *Nucleic Acids Res.* 38:2514-21 (2010)). Polynucleotides that encode the immunogenic peptides, dimeric peptides, and fusion polypeptides described herein may be synthesized commercially (see, e.g., GENSCRIPT, Piscataway, N.J.).

Polynucleotides that encode an immunogenic peptide, dimeric peptide, or fusion polypeptide described herein may be recombinantly expressed in a variety of different host cells. Host cells containing recombinant expression constructs may be genetically engineered (transduced, transformed, or transfected) with the vectors and/or expression constructs (for example, a cloning vector, a shuttle vector, or an expression construct). The vector or construct may be in the form of a plasmid, a viral particle, a phage, etc. The engineered host cells can be cultured in conventional nutrient media modified as appropriate for activating promoters, selecting transformants, or amplifying particular genes or encoding-nucleotide sequences. Selection and maintenance of culture conditions for particular host cells, such as temperature, pH and the like, will be readily apparent to the ordinarily skilled artisan. In general, the desired host cell is one that can be adapted to sustained propagation in culture to yield a stable cell line that can express sufficient amount of the peptide, dimeric peptide, or fusion polypeptide. In certain embodiments, the cell line is an immortal cell line, which refers to a cell line that can be repeatedly passaged (at least ten times while remaining viable) in culture following log-phase growth. In other embodiments the host cell used to generate a cell line is a cell that is capable of unregulated growth, such as a cancer cell, or a transformed cell, or a malignant cell.

Useful bacterial expression constructs are prepared by inserting into an expression vector a structural DNA sequence encoding the desired peptide or polypeptide together with suitable translation initiation and termination signals in an operative reading phase with a functional promoter. The construct may comprise one or more phenotypic selectable markers and an origin of replication to ensure maintenance of the vector construct and, if desirable, to provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice. Any other plasmid or vector may be used as long as the plasmid or vector is replicable and viable in the host. Thus, for example, the polynucleotides as provided herein may be included in any one of a variety of expression vector constructs as a recombinant expression construct for expressing the peptide, dimeric peptide, or fusion polypeptide. Such vectors and constructs include chromosomal, nonchromosomal, and synthetic DNA sequences, e.g., bacterial plasmids; phage DNA; baculovirus; yeast plasmids; vectors derived from combinations of plasmids and phage DNA; viral DNA, such as vaccinia, adenovirus, fowl pox virus, and pseudorabies.

The appropriate DNA sequence(s) may be inserted into the vector by a variety of procedures with which the skilled person is familiar. In certain instances, the DNA sequence is inserted into an appropriate restriction endonuclease site(s) by procedures known in the art. Notably, the fusion polypeptides described herein lack any restriction enzyme sites between any one of the immunogenic peptides that comprise the fusion polypeptide. The omission of restriction sites and the amino acid sequence encoded by the restriction site is intended to remove the possibility that a desired immunogenic epitope will be adversely altered or that an epitope will be inadvertently added that may have an undesirable immunogenicity (for example, inducing production of an antibody that recognizes a normal, human protein). Standard techniques for cloning, DNA isolation, amplification and purification, for enzymatic reactions involving DNA ligase, DNA polymerase, restriction endonucleases and the like, and various separation techniques are those known and commonly employed by those skilled in the art. Numerous standard techniques are described, for example, in Ausubel et al. (*Current Protocols in Molecular Biology* (Greene Publ. Assoc. Inc. & John Wiley & Sons, Inc., 1993)) and in Sambrook et al. (*Molecular Cloning: A Laboratory Manual,* 3rd Ed., (Cold Spring Harbor Laboratory 2001)).

The DNA sequence encoding a peptide or polypeptide in the expression vector is operatively linked to at least one appropriate expression control sequences (e.g., a promoter or a regulated promoter) to direct mRNA synthesis. Representative examples of such expression control sequences include LTR or SV40 promoter, *E. coli* lac or trp, the phage lambda $P_L$ promoter, and other promoters known to control expression of genes in prokaryotic or eukaryotic cells or their viruses. Promoter regions can be selected from any desired gene using CAT (chloramphenicol transferase) vectors or other vectors with selectable markers. Particular bacterial promoters include lacI, lacZ, T3, T5, T7, gpt, lambda $P_R$, $P_L$, and trp. Eukaryotic promoters include CMV immediate early, HSV thymidine kinase, early and late SV40, LTRs from retroviruses, and mouse metallothionein-I. Selection of the appropriate vector and promoter and preparation of certain recombinant expression constructs comprising at least one promoter or regulated promoter operatively linked to a polynucleotide described herein is well within the level of ordinary skill in the art.

Design and selection of inducible, regulated promoters and/or tightly regulated promoters are known in the art and will depend on the particular host cell and expression system. The pBAD Expression System (Invitrogen Life Technologies, Carlsbad, Calif.) is an example of a tightly regulated expression system that uses the *E. coli* arabinose operon ($P_{BAD}$ or $P_{ARA}$) (see Guzman et al., *J Bacteriology* 177:4121-30 (1995); Smith et al., *J. Biol. Chem.* 253:6931-33 (1978); Hirsh et al., *Cell* 11:545-50 (1977)), which controls the arabinose metabolic pathway. A variety of vectors employing this system are commercially available. Other examples of tightly regulated promoter-driven expression systems include PET Expression Systems (see U.S. Pat. No. 4,952,496) available from Stratagene (La Jolla, Calif.) or tet-regulated expression systems (Gossen et al., *Proc. Natl. Acad. Sci. USA* 89:5547-51 (1992); Gossen et al., *Science* 268:1766-69 (1995)). The pLP-TRE2 Acceptor Vector (BD Biosciences Clontech, Palo Alto, Calif.) is designed for use with CLONTECH's Creator™ Cloning Kits to rapidly generate a tetracycline-regulated expression construct for tightly controlled, inducible expression of a gene of interest using the site-specific Cre-lox recombination system (see, e.g., Sauer, *Methods* 14:381-92 (1998); Furth, *J. Mamm. Gland Biol. Neoplas.* 2:373 (1997)), which may also be employed for host cell immortalization (see, e.g., Cascio, *Artif. Organs* 25:529 (2001)).

Polynucleotide sequences that encode four exemplary fusion polypeptides (SEQ ID NOS:1-4) are provided in SEQ ID NOS:13, 17, 21, and 25 (encoding the fusion polypeptide comprising SEQ ID NO:1); SEQ ID NOS:14, 18, 22, and 26 (encoding the fusion polypeptide comprising SEQ ID NO:2); SEQ ID NOS: 15, 19, 23, and 27 (encoding the fusion polypeptide comprising SEQ ID NO:3); and SEQ ID NOS: 16, 20, 24, and 28 (encoding the fusion polypeptide comprising SEQ ID NO:4). Each of SEQ ID NOS:25, 26, 27, and 28 lack the expression control sequences, the codon encoding the initiating methionine residue, and the codons encoding the poly-histidine tag. Each of SEQ ID NOS:21, 22, 23, and 24 include the nucleotide sequence encoding the initiating methionine residue of the respective fusion polypeptide but lack expression control sequences and the poly-histidine tag encoding sequence. Each of SEQ ID NOS:17, 18, 19, and 20 include the expression control sequences, the codon encoding the initiating methionine residue, and the codons encoding the poly-histidine tag (see also FIGS. 2A, 2C, 2E, and 2F) Each of SEQ ID NOS:13, 14, 15, and 16 include the expression control sequences and the codon encoding the initiating methionine residue, but lack the codons encoding the poly-histidine tag.

Exemplary nucleotide sequences that encode M proteins and Spa proteins can be readily obtained as described herein from public databases (see, e.g., GenBank; GenEBML; CDC emm typing center website accessed via Internet at cdc.gov/ncidod/biotech/strep/emmtypes). The nucleotide sequence an M protein variant or Spa protein variant (or the amino terminal portion of the M protein variant or Spa protein variant) can be determined and/or identified by comparing the nucleotide sequence of a polynucleotide encoding the variant with a polynucleotide described herein or known in the art that encodes the particular M protein or Spa protein using any one of the alignment algorithms described herein and used in the art. The percent identity between two polynucleotides may thus be readily determined. Polynucleotides have 100% nucleotide sequence identity if the nucleotide residues of the two sequences are the same when aligned for maximal correspondence. In particular embodiments, the nucleotide sequence of an M protein immunogenic peptide variant-encoding polynucleotide or a Spa protein immunogenic peptide variant-encoding polynucleotide or the nucleotide sequence of the region of the polynucleotide of an M protein or Spa protein that encodes the amino terminal portion of the M protein or Spa protein from which the immunogenic peptide is derived, respectively), is at least 70%, 75%, 80%, 85%, 90%, 95%, 97%, or 98% identical to one or more of the polynucleotide sequences that encode the respective immunogenic peptide of each M protein and Spa protein, which are described herein. Polynucleotide variants also include polynucleotides that differ in nucleotide sequence identity due to the degeneracy of the genetic code and encode the amino terminal portion of an M protein or Spa protein having an amino acid sequence disclosed herein or known in the art. A polynucleotide sequence that is complementary to the encoding polynucleotide can be readily determined by a person skilled in the art. Certain polynucleotides that encode any immunogenic peptide or variant thereof may also be used as probes, primers, short interfering RNA (siRNA), or antisense oligonucleotides. Polynucleotides may be single-stranded DNA or RNA (coding or antisense) or double-stranded RNA (e.g., genomic or synthetic) or DNA (e.g., cDNA or synthetic).

Polynucleotide variants may be identified by alignment procedures described herein and in the art and also may be identified by hybridization methods. Hybridization of two polynucleotides may be performed using methods that incorporate the use of suitable moderately stringent conditions, for example, pre-washing in a solution of 5×SSC, 0.5% SDS, 1.0 mM EDTA (pH 8.0); hybridizing at 50° C.-70° C., 5×SSC for 1-16 hours; followed by washing once or twice at 22-65° C. for 20-40 minutes with one or more each of 2×, 0.5×, and 0.2×SSC containing 0.05-0.1% SDS. For additional stringency, conditions may include a wash in 0.1×SSC and 0.1% SDS at 50-60° C. for 15 minutes. As understood by persons having ordinary skill in the art, variations in stringency of hybridization conditions may be achieved by altering the time, temperature, and/or concentration of the solutions used for pre-hybridization, hybridization, and wash steps. Suitable conditions may also depend in part on the particular nucleotide sequences of the probe used (i.e., for example, the guanine plus cytosine (G/C) versus adenine plus thymidine (A/T) content). Accordingly, a person skilled in the art will appreciate that suitably stringent conditions can be readily selected without undue experimentation when a desired selectivity of the probe is identified.

If desired, immunogenic peptide variants and fusion polypeptide variants may be readily prepared by genetic engineering and recombinant molecular biology methods and techniques. Analysis of the primary and secondary amino acid sequence of the immunogenic peptide or fusion polypeptide and computer modeling of same to analyze the tertiary structure of the polypeptide may aid in identifying specific amino acid residues that can be substituted, added, or deleted without altering the structure and as a consequence, potentially the immunogenicity of the peptide or polypeptide. Modification of a polynucleotide, such as DNA, encoding an immunogenic peptide or fusion polypeptide variant may be performed by a variety of methods, including site-specific or site-directed mutagenesis of the DNA, which methods include DNA amplification using primers to introduce and amplify alterations in the DNA template, such as PCR splicing by overlap extension (SOE). Mutations may be introduced at a particular location by synthesizing oligonucleotides containing a mutant sequence, flanked by restriction sites enabling ligation to fragments of the non-variant sequence. Following ligation, the resulting reconstructed sequence encodes a variant having the desired amino acid insertion, substitution, or deletion. While restriction sites may be introduced during mutagenesis procedures, as described herein, inclusion of amino acids that are encoded by the nucleotide sequences of a restriction site in the encoded peptide or fusion polypeptide is avoided to reduce the likelihood of introducing an undesired epitope.

Site directed mutagenesis of a polynucleotide such that it encodes a variant of an immunogenic peptide or of a fusion polypeptide may be performed according to any one of numerous methods described herein and practiced in the art (Kramer et al., *Nucleic Acids Res.* 12:9441 (1984); Kunkel *Proc. Natl. Acad. Sci. USA* 82:488-92 (1985); Kunkel et al., *Methods Enzymol.* 154:367-82 (1987)). Random mutagenesis methods to identify residues that, when mutated (e.g., substituted or deleted), alter binding of the immunogenic peptide or fusion polypeptide to a ligand (e.g., a monoclonal or polyclonal antibody) can also be performed according to procedures that are routinely practiced by a person skilled in the art (e.g., alanine scanning mutagenesis; error prone polymerase chain reaction mutagenesis; and oligonucleotide-directed mutagenesis (see, e.g., Sambrook et al. *Molecular Cloning: A Laboratory Manual,* 3rd ed., Cold Spring Harbor Laboratory Press, NY (2001)). When a variant or an immunogenic peptide or fusion polypeptide is intended for use in an immunogenic composition to induce an immune response against GAS, the variant desirably retains the capability in a substantially similar manner (i.e., in a statistically, biologically, or clinically significant manner) as the non-variant immunogenic peptide or fusion polypeptide to bind to specific antibodies and to evoke production of antibodies that bind to GAS bacteria and that are bactericidal.

Characterization of Immunogenic Peptides and Fusion Polypeptides

As described in detail herein, the immunogenic peptides and fusion polypeptides comprising immunogenic peptides are intended for use as immunogens to induce an immune response, particularly a protective immune response, against a majority of GAS serotypes that cause GAS infections in humans. To determine and characterize the immunogenicity of the immunogenic peptides and fusion polypeptides, any number of immunoassays, phagocytosis and bactericidal assays, and animal studies may be performed according to methods routinely practiced by a person skilled in the art. Additional pre-clinical studies that evaluate the safety of the immunogenic composition to be administered to a subject are typically performed. Ultimately, the safety and efficacy of immunogenic compositions comprising immunogenic peptides or fusion polypeptides as described herein will be determined by clinical studies, which are monitored by regulatory agencies.

The immunogenicity of an immunogenic peptide or fusion polypeptide (or immunogenic composition comprising same) may be determined by administering an immunogenic composition described herein to a host (or subject, patient) according to immunization protocols described herein and in the art. Typically, after administering an initial dose of the immunogenic composition (also called the primary immunization) to a host, one, two or more doses of the immunogenic composition (also called boosting or booster doses) are administered.

In general, to monitor the immune response of an immunized host during pre-clinical studies in animals, sera is obtained from the animals prior to the first dose (i.e., preimmune sera) and obtained after the final boosting dose. Sera may also be obtained after any one or more of the boosting doses between the primary dose and final boosting dose. To monitor the immune response of an immunized host during clinical studies or during post-marketing studies, sera may also be obtained from humans before the first immunization and after one or more administrations of the immunogenic compositions.

An antibody that specifically binds to an immunogenic peptide (and to a fusion polypeptide, dimeric peptide, full length or mature protein, or GAS bacteria expressing the protein) may belong to any immunoglobulin class, for example IgG, IgE, IgM, IgD, or IgA. For characterizing the immunogenic peptides and fusion polypeptides described herein, use of polyclonal and/or monoclonal antibodies may be desired. The antibody may be obtained from or derived from an animal, for example, fowl (e.g., chicken) and mammals, which include but are not limited to a mouse, rat, hamster, rabbit, or other rodent, a cow, horse, sheep, goat, camel, human, or other primate. As described herein, polyclonal antisera are obtained from an animal by immunizing the animal with an immunogenic composition comprising an immunogenic peptide, plurality of immunogenic peptides or a fusion polypeptide or plurality of fusion polypeptides.

Production of immunogenic peptide-specific antibodies in an immunized host (including a human host) may include production of any class of immunoglobulin, including IgG, IgA, IgM, and/or IgE, and isotypes within the classes. The presence of specific IgG, IgM, IgE, and IgA (particularly in mucosal secretions) may be detected in a biological sample (e.g., serum, nasal wash, lung lavage, or other tissues) obtained from an immunized host. For detection of immunogenic peptide- and GAS-specific antibodies in an immunoassay, the biological sample may be permitted to interact with or contact an antigen that is purified, isolated, partially isolated, or a fragment thereof, or to interact with or contact a microorganism, which may be fixed (such as with ethanol or formaldehyde) or unfixed or non-denatured. Mucosal secretions include those collected from the respiratory tract, including the nasopharynx and lungs. Functional assays may also be performed, such as the ability of an immunogen-specific antibody to facilitate phagocytosis or opsonization of GAS, inhibit growth of GAS or kill the bacteria, or to prevent entry of GAS into a host cell. Such methods are described herein and are routinely practiced by persons skilled in the art.

Immune sera (i.e., sera obtained from a host after immunization with one or more doses of the immunogenic composition) or other biological sample may be evaluated for the presence of antibodies (immunoglobulins) that specifically bind to any one or more of the immunogenic peptides included in the immune composition (including those that are incorporated into fusion polypeptides). An assay to detect presence of a specific antibody in a biological sample, such as immunoassays described herein, may also use a mature or full-length M protein or Spa protein and/or whole GAS bacteria. The level to which antibodies in the immune sera bind to GAS serotypes represented by an immunogenic peptide in the immunogenic composition and the level to which antibodies bind to GAS serotypes not represented by an immunogenic peptide in the composition (also called non-vaccine GAS serotypes) may be determined. The level to which antibodies bind to an immunogenic peptide, fusion polypeptide, M protein, Spa protein, or GAS bacteria (typically referred in the art as titer) can be readily determined using any one or more immunoassays that are routinely practiced by the person having ordinary skill in the art. By way of non-limiting example, immunoassays include ELISA, immunoblot, radioimmunoassay, immunohistochemistry, fluorescence activated cell sorting (FACS), Ouchterlony, and the like. Immunoassays may be performed using one or more of the immunogenic peptides included in the immunizing composition, and which may be used in the assays as individual immunogenic peptides, dimeric peptides, or fusion polypeptides.

In one embodiment, a method is provided for detecting an antibody, which may be a monoclonal antibody or polyclonal antibody, and which may be of any class or isotype, and may be present in or suspected of being present in a biological sample described herein, which antibody binds to any one of the immunogenic peptides (including, for example, an immunogenic peptide comprising the amino acid sequence of any one of SEQ ID NOS: 29-59), dimeric peptides, or fusion polypeptides (including any one of the exemplary fusion polypeptides described herein, such as the fusion polypeptide comprising the amino acid sequence of any one of SEQ ID NOS:1, 2, 3, 4 and SEQ ID NOS:5-12). The method comprises contacting the biological sample with at least one of the immunogenic peptides, dimeric peptides, or fusion polypeptides described above and herein under conditions and for a time sufficient for an antibody in the sample to interact with the peptide, dimeric peptide, or fusion polypeptide (i.e., mixing, combining, or in some manner permitting the biological sample and the immunogenic peptide, fusion polypeptide, or dimeric peptide to interact). An antibody present in the biological sample that specifically binds to the peptide, dimeric peptide, or fusion polypeptide can be detected using any one of the exemplary detection methods described herein and in the art for detecting antibody-antigen binding. By way of non-limiting example, antibody bound to the peptide, dimeric peptide, or fusion polypeptide may be detected using a reagent specific for a conserved region of the antibody, such as the Fc portion of the antibody, which reagent is typically selected depending on the source of the antibody (i.e., whether the antibody is from an animal, such as a mouse, rat, goat, or sheep, etc or whether the antibody is from a human). Such reagents typically comprise a detectable label, such as for example an enzyme, fluorescent label, luminescent label, or radioactive label. Additional exemplary reagents include those that detect a specific isotype or class of antibody. Many such reagents may be obtained from commercial sources.

Conditions for a particular assay including temperature, buffers (including salts, cations, media), and other components, which maintain the integrity of the antibodies within the pre-immune and immune sera and the integrity of the antigen (which may be an immunogenic peptide, dimeric peptide, or fusion polypeptide, M protein, Spa protein, or bacteria) used in the assay, are familiar to a person skilled in the art and/or which can be readily determined. A biological sample, such as serum, is contacted (mixed, combined with, or in some manner permitted to interaction) with the antigen, under conditions and for a time sufficient to permit interaction between the antigen and antibodies present in the sample. The interaction, or level of binding, of the antigen to an antibody present in an immune serum sample (or other biological sample) may be determined and compared to a level of binding of the respective antigen to antibodies present in a pre-immune sample (or an otherwise suitable negative control). An increase in the level of binding of the antigen to the immune serum sample compared with the pre-immune serum sample indicates that the immunogenic composition evoked production of specific antibodies. As noted herein, the level of binding of an immunogen to antibodies present in a sample from an immunized host is typically referred to in the art as the titer.

Interaction or binding of an antibody to a specific antigen generally involves electrostatic interactions, hydrogen bonding, Van der Waals interactions, and hydrophobic interactions. Any one of these or any combination thereof can play a role in the binding between an antibody and its antigen. As used herein, an antibody is said to be "specific for" or to "specifically bind" an immunogenic peptide, fusion polypeptide comprising the immunogenic peptide, M protein, Spa protein, or GAS bacteria when the antibody reacts at a detectable level with the respective immunogen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. The ability of the antibody to bind to its cognate ligand (in this instance, the immunogenic peptide, fusion polypeptide, M protein, Spa protein, or bacteria) may also be expressed as a dissociation constant $K_D$, and an antibody is said to specifically bind its cognate ligand if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M.

Affinities of an antibody for an immunogenic peptide or a polypeptide comprising the immunogenic peptide, such as fusion polypeptide described herein, can be readily determined using conventional techniques, for example, those described by Scatchard et al. (*Ann. N.Y. Acad. Sci. USA* 51:660 (1949)) and by surface plasmon resonance (SPR; BIAcore™, Biosensor, Piscataway, N.J.). For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the surface plasmon resonance signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-65 (1993)).

Several in vitro assays described herein and routinely practiced in the art may be used to determine activity of specific antibodies evoked by the immunogenic and fusion polypeptides described herein. An exemplary assay is an opsonophagocytosis assay, which detects phagocytosis facilitated by the presence of opsonic antibodies present in test antisera. Briefly, the assay measures the level of phagocytosis of bacterial by neutrophils after preincubating the bacteria in the presence of immune sera. Pre-immune or other suitable negative control is also included in such an assay. Preincubated bacteria are then mixed with whole blood from a suitable host, such as a host for which opsonic protection is sought (e.g., a human), to determine the percent of neutrophils that associate with the bacterial cells, which is a measure of phagocytic activity facilitated by opsonic antibodies. The percent of neutrophils associated with the bacteria preincubated with immune sera can be compared to the percent of neutrophils associated with the bacteria that is preincubated with preimmune sera (other other suitable sera believed or known not to contain anti-GAS antibodies). A greater percent (i.e., a statistically, biologically, or clinically significant increased percent) of neutrophils associated with the bacteria pre-incubated with immune sera compared with the percent of neutrophils associated with bacteria pre-incubated with pre-immune sera indicates that the test immune sera contains opsonic antibodies.

Another exemplary in vitro assay that determines bactericidal activity of antibodies present in a sample is a bactericidal assay (see, e.g., Hu et al., supra; Examples herein). GAS bacteria are incubated with immune serum or an appropriate control serum (e.g., pre-immune serum) and then plated on medium that permits growth of GAS (e.g., sheep blood agar). Typically after an overnight incubation, the number of viable bacteria is quantified and the results are expressed as percent killing. A commonly used formula used in an indirect bactericidal assay for expressing percent killing is [(CFU (colony forming units) of bacteria sample pre-incubated with preimmune serum)—(CFU of bacteria sample pre-incubated with immune serum)÷CFU of bacteria sample pre-incubated with preimmune serum]×100.

Opsonization, phagocytosis, and bactericidal assays are art-accepted in vitro animal models for characterization of potential anti-GAS prophylactic and therapeutic treatments. Results obtained in one or more of these assays that suggest to a person skilled in the art the usefulness of a vaccine for prophylactic or therapeutic use have been supported by clinical study findings (see, e.g., U.S. Pat. No. 7,270,827; Kotloff et al., supra; McNeil et al., supra). Animal models that may be used for characterizing the immunogenicity of the immunogenic peptides, fusion polypeptides, and immunogenic compositions comprising same include those that are considered direct immunotherapy models (i.e., animals are immunized with a potential candidate immunogenic composition and then challenged with GAS) and those that are indirect or passive immunotherapy models (i.e., antiserum, or antibodies purified or isolated from antisera, obtained from animals immunized with a candidate immunogenic composition or a monoclonal antibody that is specific for a GAS antigen is administered prior to or concurrently with GAS challenge bacteria).

Animal models that mimic non-invasive GAS disease, such as pharyngitis, have been difficult to establish in rodent models. A mouse model for studying GAS impetigo has been described by Scaramuzzino et al. (*Infect. Immun.* 68:2880-87 (2000)). An non-human primate model that has been successfully developed for studying pharyngitis includes a cynomolgus macaque model of acute pharyngitis that mimics human disease (see, e.g., Ashbaugh et al., *Cellular Microbiol.* 2:283-92 (2000); Sumby et al., in *Meth. Molec. Biol.* 431:255-67 (DeLeo et al. (ed.) Humana Press, Totowa N.J. (2008))). Other animal models available in the art have been developed to evaluate therapeutics and prophylactics for invasive diseases, such as an invasive soft tissue infection (see, e.g., Ashbaugh et al., *J. Clin. Investig.* 102:550-60 (1998); Boyle et al., *J. Infect. Dis.* 177:991-97 (1998)); sepsis (see, e.g., Goldmann et al., *J. Inf. Dis.* 187:854-61 (2003); Kapur et al., *Microbiol. Pathogenesis* 16:443-50 (1994); Medina et al., *J. Infect. Dis.* 184:846-52 (2001)); and necrotizing fasciitis (Patel et al., *J. Inf. Dis.* 181:230-34 (2000)).

Polyclonal antibodies that bind specifically to an immunogenic peptide (and immune sera that comprise such polyclonal antibodies), can be prepared using methods described herein and practiced by persons skilled in the art (see, for example, Green et al., "Production of Polyclonal Antisera," in *Immunochemical Protocols* (Manson, ed.), pages 1-5 (Humana Press 1992); Harlow et al., *Antibodies: A Laboratory Manual*, Cold Spring Harbor Laboratory (1988); Williams et al., "Expression of foreign proteins in *E. coli* using plasmid vectors and purification of specific polyclonal antibodies," in *DNA Cloning* 2: *Expression Systems, 2nd Edition*, Glover et al. (eds.), page 15 (Oxford University Press 1995)). See also, for example, U.S. Pat. Nos. 7,270,827; 6,716,433; 7,402,316; 7,063,850. Although polyclonal antibodies are typically raised in animals such as rats, mice, rabbits, goats, cattle, or sheep, an antibody may also be obtained from a subhuman primate. General techniques for immunizing baboons may be found, for example, in International Patent Application Publication No. WO 91/11465 (1991) and in Losman et al., *Int. J. Cancer* 46:310, 1990.

Non-human animals that may be immunized with any one of the immunogenic peptides, dimeric peptides, fusion polypeptides, or immunogenic compositions comprising same include by way of non-limiting example, mice, rats, rabbits, hamsters, ferrets, dogs, cats, camels, sheep, cattle, pigs, horses, goats, chickens, and non-human primates (e.g., cynomolgus macaque, chimpanzee, rhesus monkeys, orangutan, and baboon). Any one of the immunogenic compositions described herein may be administered to immunize an animal by a parenteral (e.g., intravenous), intraperitoneal, intramuscular, intradermal, intraocular, or subcutaneous route. The immunogenic composition may further comprise a suitable adjuvant to enhance the immune response to the immunogen. See, e.g., Harlow et al., *Antibodies: A Laboratory Manual*, Cold Spring Harbor Laboratory (1988). Adjuvants typically used for immunization of non-human animals include but are not limited to Freund's complete adjuvant, Freund's incomplete adjuvant, montanide ISA, Ribi Adjuvant System (RAS) (GlaxoSmithKline, Hamilton, Mont.), and nitrocellulose-adsorbed antigen. In general, after the first injection, animals receive one or more booster immunizations according to a preferred schedule that may vary according to, inter alia, the immunogen, the adjuvant (if any) and/or the particular animal species. The immune response may be monitored by periodically bleeding the animal, separating the sera from the collected blood, and analyzing the sera in an immunoassay, such as an ELISA or Ouchterlony diffusion assay, or the like, to determine the specific antibody titer. When an adequate antibody titer is established, the animals may be bled periodically to accumulate the polyclonal antisera.

Polyclonal antibodies that bind specifically to the immunogen may then be purified from immune antisera, for example, by affinity chromatography using protein A or protein G immobilized on a suitable solid support (see, e.g., Coligan, supra, p. 2.7.1-2.7.12; 2.9.1-2.9.3; Baines et al., Purification of Immunoglobulin G (IgG), in *Methods in Molecular Biology,* 10:9-104 (The Humana Press, Inc. (1992)). Alternatively, affinity chromatography may be performed wherein an antibody specific for an Ig constant region of the particular immunized animal species is immobilized on a suitable solid support. Affinity chromatography may also incorporate use of one or more immunogenic peptides, dimeric peptides, or fusion proteins, which may be useful for separating polyclonal antibodies by their binding activity to a particular immunogenic peptide.

Monoclonal antibodies that specifically bind to an immunogenic peptide and immortal eukaryotic cell lines (e.g., hybridomas) that produce monoclonal antibodies having the desired binding specificity, may also be prepared, for example, using the technique of Kohler and Milstein (*Nature,* 256:495-97 (1976), *Eur. J. Immunol.* 6:511-19 (1975)) and improvements thereto (see, e.g., Coligan et al. (eds.), *Current Protocols in Immunology,* 1:2.5.1-2.6.7 (John Wiley & Sons 1991); U.S. Pat. Nos. 4,902,614, 4,543,439, and 4,411,993; *Monoclonal Antibodies, Hybridomas: A New Dimension in Biological Analyses*, Plenum Press, Kennett et al. (eds.) (1980); and *Antibodies: A Laboratory Manual*, Harlow and Lane (eds.), Cold Spring Harbor Laboratory Press (1988); see also, e.g., Brand et al., *Planta Med.* 70:986-92 (2004); Pasqualini et al., *Proc. Natl. Acad. Sci. USA* 101:257-59 (2004)). Monoclonal antibodies may be used as reagents to determine and monitor immunogenicity of immunogenic peptides, fusion polypeptides, and immunogenic compositions comprising a plurality of immunogenic peptides or fusion polypeptides.

Monoclonal antibodies may be isolated from the supernatants of eukaryotic cell cultures such as hybridoma cultures. An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Contaminants may be removed from the subsequently harvested ascites fluid (usually within 1-3 weeks) by conventional techniques, such as chromatography (e.g., size-exclusion, ion-exchange), gel filtration, precipitation, extraction, or the like (see, e.g., Coligan, supra, p. 2.7.1-2.7.12; 2.9.1-2.9.3; Baines et al., Purification of Immunoglobulin G (IgG), in *Methods in Molecular Biology,* 10:9-104 (The Humana Press, Inc. (1992)). Monoclonal antibodies may be purified by affinity chromatography using an appropriate ligand selected based on particular properties of the monoclonal antibody (e.g., heavy or light chain isotype, binding specificity, etc.). Examples of a suitable ligand, immobilized on a solid support, include Protein A, Protein G, an anti-constant region (light chain or heavy chain) antibody, an anti-idiotype antibody, or the peptide or polypeptide used for immunizing the animal that is the source of the B cells.

If desired, human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes) (see, e.g., U.S. Pat. No. 4,464,456; Glasky et al., *Hybridoma* 8:377-89 (1989)), in vitro immunization of human B cells, fusion of spleen cells from immunized transgenic mice carrying inserted human immunoglobulin genes, isolation from human immunoglobulin V region phage libraries, or other procedures as known in the art and based on the disclosure herein. For example, methods for obtaining human antibodies from transgenic mice are described, for example, by Green et al., *Nature Genet.* 7:13 (1994); Lonberg et al., *Nature* 368:856 (1994); Taylor et al., *Int. Immun.* 6:579 (1994); U.S. Pat. No. 5,877,397; Bruggemann et al., *Curr. Opin. Biotechnol.* 8:455-58 (1997); Jakobovits et al., *Ann. N.Y. Acad. Sci.* 764:525-35 (1995). In certain embodiments, a B cell that is producing the desired antibody is selected, and the light chain and heavy chain variable regions are cloned from the B cell according to molecular biology techniques known in the art (WO 92/02551; U.S. Pat. No. 5,627,052; Babcook et al., *Proc. Natl. Acad. Sci. USA* 93:7843-48 (1996)) and described herein. Chimeric antibodies, including humanized antibodies, may also be generated. A chimeric antibody has at least one constant region domain derived from a first mammalian species and at least one variable region domain derived from a second, distinct mammalian species (see, e.g., Morrison et al., *Proc. Natl. Acad. Sci. USA,* 81:6851-55 (1984); Shin et al., *Methods Enzymol.* 178:459-76 (1989); Walls et al., *Nucleic Acids Res.* 21:2921-29 (1993); U.S. Pat. No. 5,482,856). A non-human/human chimeric antibody may be further genetically engineered to create a "humanized" antibody (see, e.g., Jones et al., *Nature* 321:522-25 (1986); Riechmann et al., *Nature* 332:323-27 (1988)). Designing a humanized antibody may include determining CDR loop conformations and structural determinants of the non-human variable regions, for example, by computer modeling, and then comparing the CDR loops and determinants to known human CDR loop structures and determinants (see, e.g., Padlan et al., *FASEB* 9:133-39 (1995); Chothia et al., *Nature,* 342:377-83 (1989); Bajorath et al., *Ther. Immunol.* 2:95-103 (1995); Davies et al., *Ann. Rev. Biochem.* 59:439-73, (1990); EP-0578515-A3).

For particular uses, antigen-binding fragments of antibodies may be desired. Antibody fragments, $F(ab')_2$, Fab, Fab', Fv, and Fd, can be obtained, for example, by proteolytic hydrolysis of the antibody, for example, pepsin or papain digestion of whole antibodies according to conventional methods. An antibody fragment may also be any synthetic or genetically engineered protein that acts like an antibody in that it binds to a specific antigen to form a complex according to numerous methods described in the art (see, for example, Larrick et al., *Methods: A Companion to Methods in Enzymology* 2:106, (1991); Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995); and Ward et al., "Genetic Manipulation and Expression of Antibodies," in *Monoclonal Antibodies: Principles and Applications*, Birch et al., (eds.), page 137 (Wiley-Liss, Inc. 1995))

Antibodies may also be identified and isolated from human immunoglobulin phage libraries, from rabbit immunoglobulin phage libraries, from mouse immunoglobulin phage libraries, and/or from chicken immunoglobulin phage libraries (see, e.g., Winter et al., *Annu. Rev. Immunol.* 12:433-55 (1994); Burton et al., *Adv. Immunol.* 57:191-280 (1994); U.S. Pat. No. 5,223,409; Huse et al., *Science* 246:1275-81 (1989); Schlebusch et al., *Hybridoma* 16:47-52 (1997) and references cited therein; Rader et al., *J. Biol. Chem.* 275:13668-76 (2000); Popkov et al., *J. Mol. Biol.* 325:325-35 (2003); Andris-Widhopf et al., *J. Immunol. Methods* 242:159-31 (2000)). Antibodies isolated from non-human species or non-human immunoglobulin libraries may be genetically engineered according to methods described herein and known in the art to "humanize" the antibody or fragment thereof. Immunoglobulin variable region gene combinatorial libraries may be created in phage vectors that can be screened to select Ig fragments (Fab, Fv, scFv, or multimers thereof) that bind specifically to an immunogenic peptide as described herein (see, e.g., U.S. Pat. No. 5,223,409; Huse et al., *Science* 246: 1275-81 (1989); Sastry et al., *Proc. Natl. Acad. Sci. USA* 86:5728-32 (1989); Alting-Mees et al., *Strategies in Molecular Biology* 3:1-9 (1990); Kang et al., *Proc. Natl. Acad. Sci. USA* 88:4363-66 (1991); Hoogenboom et al., *J. Molec. Biol.* 227:381-388 (1992); Schlebusch et al., *Hybridoma* 16:47-52 (1997) and references cited therein; U.S. Pat. No. 6,703,015).

Preparation of Immunogenic Compositions

The immunogenic compositions described herein may be used for immunizing a subject (a human or non-human animal) to induce an immune response against GAS. The immunogenic compositions may be formulated such that the compositions are pharmaceutically or physiologically acceptable or suitable compositions, preparations, or formulations for administration to a human or non-human animal. Immunogenic compositions may be combined with a pharmaceutically acceptable (i.e., physiologically suitable or acceptable) excipient(s), which are described in greater detail herein. Any physiological or pharmaceutically suitable excipient or carrier (i.e., a non-toxic material that does not interfere with the activity of the active ingredient) known to those of ordinary skill in the art for use in pharmaceutical compositions may be employed in the compositions described herein. Exemplary excipients include diluents and carriers that maintain stability and integrity of the component(s) of the composition. Exemplary excipients include diluents and carriers that maintain stability and integrity of proteins. Excipients for therapeutic use are well known, and are described, for example, in *Remington: The Science and Practice of Pharmacy* (Gennaro, 21$^{st}$ Ed. Mack Pub. Co., Easton, Pa. (2005)), which are described in greater detail herein. The choice of an excipient depends on several factors, including the stability of the immunogenic peptides or fusion polypeptides; the route of administration; and the dosing schedule. For example, saline and phosphate buffered saline at physiological pH may be used. Preservatives, stabilizers, dyes and even flavoring agents (if administered orally) may be provided in the composition.

The immunogenic compositions described herein may also comprise a suitable adjuvant. An adjuvant is intended to enhance (or improve, augment) the immune response to the immunogenic peptides and fusion polypeptides comprising the peptides (i.e., increase the level of the specific immune response to the immunogenic peptide and in a statistically, biologically, or clinically significant manner compared with the level of the specific immune response in the absence of administering the adjuvant).

For administration in humans, a pharmaceutically acceptable adjuvant is one that has been approved or is approvable for human administration by pertinent regulatory bodies. For example, as discussed herein and known in the art, Complete Freund's adjuvant is not suitable for human administration. Desired adjuvants augment the response to the immunogenic peptide or fusion polypeptide without causing conformational changes in the immunogen that might adversely affect the qualitative immune response. Suitable adjuvants include aluminum salts, such as alum (potassium aluminum sulfate), or other aluminum containing adjuvants such as aluminum hydroxide, aluminum phosphate, or aluminum sulfate. Other pharmaceutically suitable adjuvants include nontoxic lipid A-related adjuvants such as, by way of non-limiting example, nontoxic monophosphoryl lipid A (see, e.g., Persing et al., *Trends Microbiol.* 10:s32-s37 (2002)), for example, 3 De-O-acylated monophosphoryl lipid A (MPL) (see, e.g., United Kingdom Patent Application No. GB 2220211). Other useful adjuvants include QS21 and QuilA that comprise a triterpene glycoside or saponin isolated from the bark of the *Quillaja saponaria* Molina tree found in South America (see, e.g., Kensil et al., in *Vaccine Design: The Subunit and Adjuvant Approach* (eds. Powell and Newman, Plenum Press, NY, 1995); U.S. Pat. No. 5,057,540). Other suitable adjuvants include oil in water emulsions, optionally in combination with immune stimulants, such as monophosphoryl lipid A (see, e.g., Stoute et al., *N. Engl. J. Med.* 336, 86-91 (1997)). Other suitable adjuvants include polymeric or monomeric amino acids such as polyglutamic acid or polylysine, liposomes, and CpG (see, e.g., Klinman, *Int. Rev. Immunol.* 25(3-4):135-54 (2006); U.S. Pat. No. 7,402,572; European Patent No. 772 619).

The immunogenic compositions described herein may be formulated by combining the plurality of immunogenic peptides or the plurality of fusion polypeptides with at least one pharmaceutically acceptable excipient. As described herein the immunogenic compositions may further comprise a pharmaceutically suitable adjuvant. Typically, all immunogenic peptides or all fusion polypeptides intended to be administered to a host are combined in a single immunogenic composition, which may include at least one pharmaceutically acceptable excipient and which may further include a pharmaceutically suitable adjuvant. Alternatively, for example, multiple immunogenic compositions may be formulated separately for separate administration, which could be by any route described herein or in the art and which could be sequential or concurrent.

The immunogenic compositions described herein may be formulated as sterile aqueous or non-aqueous solutions, suspensions or emulsions, which as described herein may additionally comprise a physiologically acceptable excipient (which may also be called carrier) and/or a diluent. The immunogenic compositions may be in the form of a solid, liquid, or gas (aerosol). Alternatively, immunogenic compositions described herein may be formulated as a lyophilate (i.e., a lyophilized composition), or may be encapsulated within liposomes using technology known in the art. Immunogenic compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins (such as albumin), polypeptides or amino acids such as glycine, antioxidants, chelating agents such as EDTA or glutathione, stabilizers, dyes, flavoring agents, and suspending agents and/or preservatives.

In general, as discussed herein, the type of excipient is selected on the basis of the mode of administration. The compositions and preparations described herein may be formulated for any appropriate manner of administration, including, for example, topical, buccal, lingual, oral, intranasal, intrathecal, rectal, vaginal, intraocular, subconjunctival, transdermal, sublingual or parenteral administration, including subcutaneous, intravenous, intramuscular, intrasternal, intracavernous, intrameatal or intraurethral injection or infusion.

For parenteral administration, such as subcutaneous injection or intramuscular injection, the carrier or excipient preferably comprises water, saline, alcohol, a fat, a wax or a buffer, and the immunogenic composition is sterile. For oral administration, any of the above excipients or a solid carrier, such as mannitol, lactose, starch, magnesium stearate, sodium saccharin, talcum, cellulose, glucose, sucrose, and magnesium carbonate, may be employed. Biodegradable microspheres (e.g., polylactic galactide) as well as nanoparticles may also be used as carriers for the compositions described herein. Suitable biodegradable microspheres described, for example, in U.S. Pat. Nos. 4,897,268 and 5,075,109. In particular embodiments in which the composition or preparation is combined with a microsphere, the microsphere is larger than approximately 25 microns. An immunogenic composition described herein may be lyophilized or otherwise formulated as a lyophilized product using one or more appropriate excipient solutions (e.g., sucrose, physiological saline) as diluents upon administration. Nanoparticles may be used to deliver the lyphophilized product and appropriate excipient(s).

The immunogenic compositions disclosed herein may be intended for topical administration, such as directly to mucosal tissue, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration (e.g., oral or vaginal). The immunogenic compositions described herein may be administered topically by using any one of several delivery vehicles described herein and used in the art, including but not limited to a sponge, gel cap, suppository, gauze (or other suitable fabric for application to the tissue to be treated), nanoparticles, and a lozenge. With respect to certain delivery vehicles, such as a sponge, fabric, or gauze, the composition or preparation is attached to, absorbed by, adsorbed to, or in some manner applied to the vehicle that permits release of the composition or preparation upon contact with the tissue to be treated.

An immunogenic composition disclosed herein may be intended for rectal, oral, or vaginal administration, in the form, e.g., of a suppository or lozenge, which will melt in the rectum, oral, or vaginal space, respectively, and release the drug or components of the composition. A composition or preparation described herein that is administered orally may also be in the form of a liquid. The composition or preparation for rectal administration may contain an oleaginous base as a suitable nonirritating excipient. Such bases include, without limitation, lanolin, cocoa butter and polyethylene glycol.

The immunogenic compositions described herein are preferably endotoxin free, particularly when delivered parenterally. An endotoxin free composition is substantially free of endotoxins and/or related pyrogenic substances (i.e., an endotoxin is not detectable by methods accepted by regulatory agencies to demonstrate with sufficient sensitivity whether an endotoxin is present). Endotoxins include toxins that are present in viable microorganisms and include toxins that are released only when the microorganisms lack cell integrity or die. Pyrogenic substances include fever-inducing, thermostable substances (lipopolysaccharides and glycoproteins) located in the outer membrane of bacteria and other microorganisms. These substances can cause fever, hypotension, and shock when administered to humans. Manufacturing compositions that are endotoxin-free can require special equipment, expert artisans, and can be significantly more expensive than making formulations that are not endotoxin-free.

In another embodiment, a method of manufacture of the immunogenic compositions described herein is provided. Methods of manufacture comprise combining or mixing together the desired plurality of immunogenic peptides or desired fusion polypeptides to provide the immunogenic compositions described herein. The methods of manufacture may further comprise combining or mixing one or more physiologically suitable (or pharmaceutically suitable) excipients as described herein. The methods may further comprise combining or mixing the immunogenic composition comprising the desired immunogenic peptides or desired fusion polypeptides with a pharmaceutically suitable adjuvant; at least one pharmaceutically suitable excipient may also be combined or mixed with the immunogenic composition comprising an adjuvant. In still further embodiments, a method of manufacture comprises chemical synthesis or recombinant production of the desired immunogenic peptides or desired fusion polypeptides. Chemical synthesis and recombinant production of the immunogenic peptides and fusion polypeptides are described in detail herein. During manufacture of each immunogenic peptide and fusion protein, appropriate manufactures processes (such as Good Manufacturing Practices (GMP)) as required by a regulatory agency are employed. In addition, persons skilled in the art is familiar with techniques and steps to be taken to maintain stability and integrity of the peptides or fusion polypeptides during manufacture of an immunogenic composition.

Methods of Using Immunogenic Peptides, Fusion Polypeptides, and Immunogenic Compositions The immunogenic compositions described herein that comprise a plurality of GAS immunogenic peptide, for example, least 31 different immunogenic peptides derived from GAS M proteins or GAS Spa proteins, and immunogenic compositions described herein that comprise at least four fusion polypeptides that comprise the plurality of immunogenic peptides (e.g., the at least 31 different immunogenic peptides each independently comprising at least 25 contiguous amino acids from the amino terminal portions of one of the M proteins from GAS M serotypes 1; 2; 3; 4; 5; 6; 11; 12; 14; 18; 19; 22; 24; 28; 29; 44; 49; 58; 73; 75; 77; 78; 81; 82; 83; 87; 89; 92; 114; 118, or Spa protein from GAS serotype 18) may be used for inducing an immune response against GAS. Accordingly, in certain embodiments, methods are provided herein that comprise immunizing a host (or subject), which may be a human host, in a manner appropriate to evoke an immune response (including a humoral response) against GAS bacteria. These compositions described herein are therefore useful for prophylactic and/or therapeutic treatment of a host in need thereof who has inadequate immunity to GAS and is susceptible to infection.

Methods described herein for inducing an immune response against GAS and for preventing (i.e., reducing the likelihood of occurrence) and/or treating a GAS infection comprise administering an immunogenic composition described herein to the host once, twice, three times, four times, or more times at appropriate time intervals to evoke and maintain the desired anti-GAS immune response. As long known in the art, protection of a host against GAS infection generally correlates with the production of opsonizing antibodies against GAS serotype-specific M protein (see, e.g., Lancefield, *J. Immunol.* 89:307, 1962). In addition, the presence of secretory or mucosal anti-GAS antibodies in the host may prevent (reduce or decrease likelihood of occurrence) initial colonization by *streptococci*. Because the immunogenic compositions described herein that comprise a plurality of immunogenic peptides or comprise fusion polypeptides comprising the plurality of immunogenic peptides may be used for prevention, amelioration, or treatment of GAS infection, the immunogenic compositions may also be referred to as vaccines by a person skilled in the art.

The dose of each immunogenic composition, the number of doses administered to the host, and the time intervals between two doses of the composition may be determined by a person skilled in the medical art. The appropriate amount of each immunogenic peptide or the amount of each fusion polypeptide in the immunogenic composition administered to the host may depend upon the host's or patient's (e.g., human's) condition, that is, stage of the disease, general health status, as well as age and weight, and other factors familiar to a person skilled in the medical art. Hosts or subjects who may be immunized with the immunogenic compositions described herein include human and non-human hosts and subjects. Human hosts/subjects include infants, children, or an adult. Immunogenic compositions suitable for administration to an adult may further be prepared dependent on whether the adult is a young adult, middle-aged, or a senior adult.

Immunogenic compositions may be administered in a manner appropriate to the disease to be treated (or prevented) as determined by persons skilled in the medical art. An appropriate dose and a suitable duration and frequency of administration will be determined by factors such as the condition of the patient, age of the patient, the type and severity of the patient's disease to be treated or prevented, the particular form of the active ingredient, and the method of administration. In general, an appropriate dose and treatment regimen provides the immunogenic composition in an amount sufficient to provide therapeutic and/or prophylactic benefit (e.g., an improved clinical outcome, overall survival, or a lessening of symptom severity). For prophylactic use, a dose should be sufficient to prevent or delay the onset of, and/or to diminish the severity of an infection in a statistically, biologically, or clinically significant manner.

Optimal doses may generally be determined using experimental in vitro, in vivo animal models, and/or human clinical trials. The optimal dose may depend upon the body mass, weight, or blood volume of the host. In general, the amount of an immunogenic peptide or fusion polypeptide as described herein present in a dose, ranges from about 10 μg to about 10 mg, from about 100 μg to 1 mg, from about 150 μg to 500 μg, or from about 200 μg to about 400 μg. The use of the minimum dosage that is sufficient to provide effective therapy and/or prophylaxis is usually preferred. Patients may generally be monitored for therapeutic or prophylactic effectiveness using assays suitable for the condition being treated or prevented, which assays will be familiar to those having ordinary skill in the art. When administered in a liquid form, suitable dose sizes will vary with the size of the patient, but will typically range from about 1 ml to about 500 ml (comprising an appropriate dose) for a 10-60 kg subject.

Booster immunizations may be administered multiple times (e.g., two times or three times or four times or more), at desired time intervals ranging from about 2 weeks to about 26 weeks, such as 2, 4, 8, 12, 16, or 26 week intervals. The time intervals between different doses (e.g., between the primary dose and second dose, or between the second dose and a third dose) may not be the same, and the time interval between each two doses may be determined independently.

The immunogenic compositions described herein may be administered a route including oral, enteral, parenteral, transdermal/transmucosal, and inhalation. The term enteral, as used herein, is a route of administration in which the agent is absorbed through the gastrointestinal tract or oral mucosa, including oral, rectal, and sublingual. The term parenteral, as used herein, describes administration routes that bypass the gastrointestinal tract, and are typically administered by injection or infusion, including intraarterial, intradermal, subdermal, intramuscular, intranasal, intraocular, intraperitoneal, intravenous, subcutaneous, submucosal, intravaginal, intrasternal, intracavernous, intrathecal, intrameatal, and intraurethral injection. The term transdermal/transmucosal, as used herein, is a route of administration in which the agent is administered through or by way of the skin, including topical. The term inhalation encompasses techniques of administration in which an agent is introduced into the pulmonary tree, including intrapulmonary or transpulmonary and includes intranasal administration. In more particular embodiments, the immunogenic compositions described herein may be administered orally, intramuscularly, or intranasally. All doses of the immunogenic compositions may not be administered by the same route. In certain embodiments, different doses of the immunogenic compositions may be delivered by different routes, such as by two or more of oral, intramuscular, and intransal routes.

The immunogenic compositions described herein may be used to reduce the likelihood of occurrence of a GAS infection or to treat a GAS infection that causes any one of the following: pharyngitis, scarlet fever, necrotizing fasciitis, cellulitis, meningitis, pneumonia, streptococcal toxic shock syndrome, bacteremia, septicemia, septic arthritis, pyoderma, skin infections (invasive and non-invasive), impetigo, erysipelas, soft-tissue infection, nephritis, and GAS pyrogenic reaction. Methods described herein for inducing an immune response against GAS and reducing the likelihood of occurrence or treating a GAS infection may also effectively reduce the likelihood of occurrence or severity of nonsuppurative sequelae such as acute rheumatic fever, rheumatic heart disease, reactive arthritis, and glomerulonephritis.

Immunized subjects may generally be monitored for therapeutic or prophylactic effectiveness using assays suitable for the infection or condition being treated or prevented, which assays will be familiar to those having ordinary skill in the art and which are described herein. The immune response evoked by administering the immunogenic compositions described herein according to the methods described above comprises an adaptive immune response that includes a humoral response and may also include a cellular response (which comprises a CD4 immune response and a CD8 immune response) specific for each immunogen peptide represented in the immunogenic composition. The humoral immune response (i.e., antibody response) can be monitored throughout an immunization protocol using any one of the immunoassays (e.g., ELISA, immunoblotting), in vitro functional assays (e.g., opsonic, phagocytic and killing assays, indirect bactericidal assays) and the like. Such methods are useful for monitoring and determining the level of binding (i.e., titer) of specific antibodies present in a biological sample (e.g., sera) from an immunized host. Based on the results from one or more of these assays, the dose or timing of the next dose or the necessity for an additional dose can be determined.

A cell-mediated immune response involves various types of T cells (i.e., T lymphocytes). In a cell mediated response, T cells act to eliminate an antigen by a number of mechanisms. For example, helper T cells that are capable of recognizing specific antigens may respond by releasing soluble mediators such as cytokines to recruit additional cells of the immune system to participate in an immune response. Also, cytotoxic T cells are capable of specifically recognizing an antigen and may respond by binding to and destroying or damaging an antigen-bearing cell such as a GAS bacterial cell.

Assays routinely practiced in the art to examine cellular immune response include determining the presence and level of soluble mediators such as cytokines, lymphokines, chemokines, hormones, growth factors, as well as other mediators. Immunoassays also include determining cellular activation state changes of immune cells by analyzing altered functional or structural properties of the immune cells, for example, cell proliferation, altered motility, induction of specialized activities such as specific gene expression or cytolytic behavior; cell maturation, and alteration in relationship between a Th1 response and a Th2 response. Procedures for performing these and similar assays are may be found, for example, in Lefkovits (*Immunology Methods Manual: The Comprehensive Sourcebook of Techniques,* 1998). See also *Current Protocols in Immunology*; Weir, *Handbook of Experimental Immunology*, Blackwell Scientific, Boston, Mass. (1986); Mishell and Shigii (eds.) *Selected Methods in Cellular Immunology*, Freeman Publishing, San Francisco, Calif. (1979); Green and Reed, *Science* 281:1309 (1998) and references cited therein).

As described briefly herein, a biological sample may be obtained from the subject for determining the presence and level of an immune response to immunogenic peptide(s), to a fusion polypeptide comprising the immunogenic peptides, and/or to a full-length or mature, or GAS bacteria in the subject who has received the immunogenic compositions described herein. A "biological sample" as used herein may be a blood sample (from which serum or plasma may be prepared), biopsy specimen, body fluids (e.g., lung lavage, ascites, mucosal washings, synovial fluid), bone marrow, lymph nodes, tissue explant, organ culture, or any other tissue or cell preparation from the subject or a biological source. Biological samples may also be obtained from the subject prior to receiving any immunogenic composition, which biological sample is useful as a control for establishing baseline (i.e., pre-immunization) data.

Determining the effectiveness of immunization with the immunogenic compositions described herein may also include clinical evaluation. By way of example, the presence of a GAS infection may be determined by performing routine assays (bacteria cell culture; immunofluorescence assays) available to the clinician to determine quickly if GAS are present in a body fluid or at a site on the body, such as the throat, mucosal tissue, or skin. Symptomatology, such as fever, inflammation, pain, and various other and numerous symptoms of GAS infections can be monitored by persons skilled in the clinical art.

Immunogenic peptides, dimeric peptides, and fusion polypeptides described herein may be used as reagents for detecting the presence and level of specific antibody in a sample. A biological sample, such as by way of non-limiting example, a biological sample described herein from an immunized host, or a cell supernatant or cell lysate from cell lines that are known to or suspected of producing a specific monoclonal antibody is obtained. The biological sample is contacted with (i.e., mixed with, combined with, or in some manner permitted to interact with) an immunogenic peptide (or dimeric peptide, fusion polypeptide, mature or full-length protein, or GAS bacteria which each may comprise the immunogenic peptide) for a time sufficient and under conditions suitable to permit an antibody in the biological sample and the immunogenic peptide (alone or as part of a larger molecule) to interact. The level of interaction between the biological sample and the immunogenic peptide is detected and compared with the level of interaction of the immunogenic peptide with a control biological sample that serves as a baseline or negative control. The level of interaction (i.e., binding of an antibody and immunogenic peptide) can be determined by any one of the numerous immunoassay methods described herein and the art and with which a person skilled in the art is familiar.

Immunogenic peptides, dimeric peptides, and fusion polypeptides described herein may also be used for methods for producing polyclonal antibodies or monoclonal antibodies that bind specifically to an immunogenic peptide. Exemplary methods are described in detail herein.

EXAMPLES

Example 1

M Protein from GAS Serotype 4

This example describes characterization of a GAS antigen expressed by and present on the cell surface of GAS serotype 4.

The potential protective efficacy of the 30-valent vaccine described below and herein was enhanced by the discovery of opsonic epitopes within the N-terminus of the protein Arp4, which is a component of protein 2. Arp4 was previously shown to bind IgA but was not required for virulence or resistance to phagocytosis (see, e.g., Husmann et al., *Infect. Immun.* 63:345-348 (1995)). The most recent epidemiologic studies found that Type 4 streptococcal infections account for up to 9% of all GAS infections. To detect opsonic epitopes within the N-terminus of Arp4 (M4), rabbit antisera were raised against (1) a synthetic peptide representing the N-terminal 30 amino acids of the protein, (2) a recombinant fusion protein containing 50 amino-terminal residues of Arp4 as well as 5 other M peptides, or (3) the intact recombinant Arp4 protein. All three antisera provided significant bactericidal activity when tested using in vitro bactericidal assays (see Example 3 for experimental protocol): anti-sM4(1-30) antisera resulted in 52% killing; antisera obtained from rabbits immunized with recombinant 50 aa Arp4 peptide as a component of a hexavalent fusion protein had 82% killing; and antisera from animals immunized with intact recombinant Arp4 provided 85% killing. The results of the functional killing assays indicated that the N-terminal peptide of Arp4 (M4) was a suitable candidate for inclusion in the 30-valent vaccine.

Example 2

Design and Construction of Multivalent GAS Peptide Compositions

This example describes selection of GAS serotypes from which M proteins immunogenic fragments would be selected and describes construction of fusion polypeptides comprising these immunogenic fragments.

M peptides were selected from serotypes of GAS based on the epidemiology of 1) pharyngitis in pediatric subjects in North America (see, e.g.; Shulman et al., *Clin. Infect. Dis.* 2009, supra); (2) invasive GAS infections (see, e.g., Active Bacterial Core Surveillance of the Emerging Infections Program Network, supported by the Centers for Disease Control and Prevention) (see, e.g., O'Loughlin et al., supra); and (3) invasive infections in Europe (for example, as reported by the StrepEuro consortium, see Luca-Harari et al., supra). Also included in the 30-valent vaccine composition were M peptides from serotypes of GAS that are currently or have been historically considered "rheumatogenic" (see, e.g., Shulman et al., *Clin. Infect. Dis.* 42:441-47 (2006)) and the amino-terminal peptide fragment of Spal 8 (also called Spa protein from GAS serotype 18, a protective antigen that is expressed by at least several serotypes of group A *streptococci* (see, e.g., Dale et al., *J. Clin. Invest.* 103:1261-68 (1999); U.S. Pat. No. 7,063,850; International Patent Application Publication No. WO 00/37648).

The amino acid sequences of the M proteins selected for inclusion in the immunogenic composition were obtained from the (Center for Disease Control (CDC) emm typing center website that may be found by accessing the Internet at cdc.gov/ncidod/biotech/strep/emmtypes. When sub-types were present, in most instances, the sequence of the M protein from the predominant subtype was selected. The amino-terminal regions of the mature M proteins and Spa were searched by BlastP in the GenBank database to identify regions of homology with human proteins. Amino-terminal regions that had five or more contiguous amino acid that were identical with human proteins were not incorporated into the vaccine design.

Construction and expression recombinant multivalent fusion proteins. The specific 5' sequences of each emm gene were used to design four hybrid DNA molecules. Each gene was chemically synthesized (GENSCRIPT®, Piscataway, N.J.) to contain 7 or 8 emm gene fragments linked in tandem, an upstream T7 promoter, and a 3' poly-histidine motif followed by a stop codon. Unlike the 26-valent vaccine (see Hu et al., supra; U.S. Pat. No. 7,270,827), no linking codons were inserted between the emm sequences. Optimization of codons for *E. coli* was accomplished during synthesis rather than by subsequent site mutation. The DNA strands were annealed and ligated into pUC57; the integrity of the synthetic gene sequences was verified by sequencing using the ABI dye termination method. Expression of each multivalent fusion protein was detected by SDS-PAGE analysis using whole cell lysates before and after IPTG induction. A polypeptide tag of six histidine residues (i.e., His-tag) has been added at the carboxy (also called herein and in the art, COOH) terminus for ease of purification by nickel affinity chromatography according to methods routinely practiced in the art.

FIG. 1 provides a schematic of the encoded M protein immunogenic peptides for each of four fusion proteins. The serotypes from which M proteins were included in the vaccine composition included GAS serotypes that accounted for 98% of all cases of pharyngitis in the U.S. and Canada, 90% of invasive disease in the U.S., and 78% of invasive disease in Europe. In FIG. 1, the numbers below the depiction of each immunogenic peptide refer to the location of the amino acids in the amino terminal portion of the M protein or Spa protein. By way of illustration and explanation, in Protein 1, the M1 immunogenic peptide contains amino acids at positions 1-50 from the amino terminus of the M protein from GAS serotype 1; the M3.1 immunogenic peptide contains amino acids at positions 22-71 from the amino terminal portion of the M protein from GAS serotype 3.1; M6.4 contains a tandem repeat of amino acids at positions 1-25 from the amino terminal portion of GAS serotype 6.4, etc. At the carboxy terminal end of Protein 1, the M1 immunogenic peptide (amino acids 1-50) is repeated. The total number of amino acids in each fusion protein is provided at the right hand end of the schematic for each protein; the initiating methionine residue at the amino terminus is included in the total amino acid number.

The amino acid sequences of the immunogenic peptides are presented in Table 1. The initiating amino acid (typically a methionine) of the full-length M protein is not included in the immunogenic fragment peptide sequence for each peptide of the fusion proteins (see Table 1). The nucleotide sequence of polynucleotides encoding the four fusion proteins and the amino acid sequences of the encoded polypeptides are presented in FIGS. 2A-2H. The nucleotide sequences provided in FIG. 2 include expression control sequences upstream of the coding region and nucleotides at the carboxy terminus that encode the His-tag (see also SEQ ID NOS: 17-20, polynucleotides encoding Fusion Proteins 1-4, respectively). Nucleotide sequences encoding fusion proteins 1-4 that include the expression control sequences but exclude the His-tag encoding nucleotides are provided in SEQ ID NOS: 13-16, respectively. Nucleotide sequences encoding fusion proteins 1-4 that exclude the expression control sequences, exclude the His-tag encoding nucleotides, and include nucleotides encoding the amino terminus methionine (ATG) are provided in SEQ ID NOS: 17-20, respectively. Nucleotide sequences encoding fusion proteins 1-4 that exclude the expression control sequences, exclude the His-tag encoding nucleotides, and exclude nucleotides encoding the amino terminus methionine are provided in SEQ ID NOS: 21-24, respectively.

Purification of recombinant multivalent vaccine component fusion proteins. Each fusion protein was purified separately according to procedures previously reported (see, e.g., Hu et al., supra). Purity was monitored using SDS-PAGE, and fractions containing pure recombinant protein were pooled and stored at −20° C. until use.

Construction and expression of individual recombinant dimeric m peptides. Individual recombinant dimeric peptides comprising vaccine component peptides were expressed and purified to use as serologic reagents, as previously described (see, e.g., Hu et al., supra). In addition, seven new M peptides were chemically synthesized for these studies (GENSCRIPT®, Piscataway, N.J.).

TABLE 1

AMINO ACID SEQUENCES OF M PROTEIN IMMUNOGENIC PEPTIDES

| M protein ($NH_2$ terminal resiudes) | Amino Acid Sequence | Fusion Protein Location | Sequence Identifier |
|---|---|---|---|
| M1 (1-50) | NGDGNPREVI EDLAANNPAI QNIRLRHENK DLKARLENAM EVAGRDFKRA | 1-50 and 401-450 of Protein 1 (SEQ ID NO: 1) | SEQ ID NO: 29 |
| M3.1 (22-71) | LLDQVTQLYT KHNSNYQQYN AQAGRLDLRQ KAEYLKGLND WAERLLQELN | 51-100 of Protein 1 (SEQ ID NO: 1) | SEQ ID NO: 30 |
| M6.4 $(1-25)_2$ | RVFPRGTVEN PDKARELLNK YDVENRVFPR GTVENPDKAR ELLNKYDVEN | 101-150 of Protein 1 (SEQ ID NO: 1) | SEQ ID NO: 31 |
| M2 $(2-26)_2$ | SKNPVPVKKE AKLSEAELHD KIKNLSKNPV PVKKEAKLSE AELHDKIKNL | 151-200 of Protein 1 (SEQ ID NO: 1) | SEQ ID NO: 32 |
| M18 (1-50) | APLTRATADN KDELIKRAND YEIQNHQLTV ENKKLKTDKE QLTKENDDLK | 201-250 of Protein 1 (SEQ ID NO: 1) | SEQ ID NO: 33 |
| M28 (1-50) | AESPKSTETS ANGADKLADA YNTLLTEHEK LRDEYYTLID AKEEEPRYKA | 251-300 of Protein 1 (SEQ ID NO: 1) | SEQ ID NO: 34 |
| M12 (1-50) | DHSDLVAEKQ RLEDLGQKFE RLKQRSELYL QQYYDNKSNG YKGDWYVQQL | 301-350 of Protein 1 (SEQ ID NO: 1) | SEQ ID NO: 35 |
| SPA (1-50) | DSVSGLEVAD PSDSKKLIEL GLAKYLNDKL PFKTKEDSEI LSELRDVLKN | 351-400 of Protein 1 (SEQ ID NO: 1) | SEQ ID NO: 36 |
| M4 (1-50) | AEIKKPQADS AWNWPKEYNA LLKENEELKV EREKYLSYAD DKEKDPQYRA | 1-50 and 401-450 of Protein 2 (SEQ ID NO: 2) | SEQ ID NO: 37 |
| M5.0 $(1-25)_2$ | AVTRGTINDP QRAKEALDKY ELENHAVTRG TINDPQRAKE ALDKYELENH | 51-100 of Protein 2 (SEQ ID NO: 2) | SEQ ID NO: 38 |
| M11 (1-50) | TEVKAAGQSA PKGTNVSADL YNSLWDENKT LREKQEEYIT KIQNEETKNK | 101-150 of Protein 2 (SEQ ID NO: 2) | SEQ ID NO: 39 |
| M75 (1-50) | EEERTFTELP YEARYKAWKS ENDELRENYR RTLDKFNTEQ GKTTRLEEQN | 151-200 of Protein 2 (SEQ ID NO: 2) | SEQ ID NO: 40 |
| M19 (1-25)2 | RVRYTRHTPE DKLKKIIDDL DAKEHRVRYT RHTPEDKLKK IIDDLDAKEH | 201-250 of Protein 2 (SEQ ID NO: 2) | SEQ ID NO: 41 |
| M29.2 (1-50) | RVYITRRMTK EDVEKIANDL DTENHGLKQQ NEQLSTEKQG LEEQNKQLST | 251-300 of Protein 2 (SEQ ID NO: 2) | SEQ ID NO: 42 |
| M14.3 (1-50) | DRVSRSMSRD DLLNRAQDLE AKNHGLEHQN TKLSTENKTL QEQAEARQKE | 301-350 of Protein 2 (SEQ ID NO: 2) | SEQ ID NO: 43 |
| M24 (1-50) | VATRSQTDTL EKVQERADKF EIENNTLKLK NSDLSFNNKA LKDHNDELTE | 351-400 of Protein 2 (SEQ ID NO: 2) | SEQ ID NO: 44 |
| M77 (1-50) | EGVSVGSDAS LHNRITDLEE EREKLLNKLD KVEEEHKKDH EQLEKKSEDV | 1-50 and 401-450 of Protein 3 (SEQ ID NO: 3) | SEQ ID NO: 45 |
| M22 (1-50) | ESSNNAESSN ISQESKLINT LTDENEKLRE ELQQYYALSD AKEEEPRYKA | 51-100 of Protein 3 (SEQ ID NO: 3) | SEQ ID NO: 46 |
| M73 (1-50) | DNQSPAPVKK EAKKLNEAEL YNKIQELEEG KAELFDKLEK VEEENKKVKE | 101-150 of Protein 3 (SEQ ID NO: 3) | SEQ ID NO: 47 |

TABLE 1-continued

| AMINO ACID SEQUENCES OF M PROTEIN IMMUNOGENIC PEPTIDES | | | |
|---|---|---|---|
| M protein ($NH_2$ terminal resiudes) | Amino Acid Sequence | Fusion Protein Location | Sequence Identifier |
| M89 (1-50) | DSDNINRSVS VKDNEKELHN KIADLEEERG EHLDKIDELK EELKAKEKSS | 151-200 of Protein 3 (SEQ ID NO: 3) | SEQ ID NO: 48 |
| M58 (1-50) | DSSREVTNEL TASMWKAQAD SAKAKAKELE KQVEEYKKNY ETLEKGYDDL | 201-250 of Protein 3 (SEQ ID NO: 3) | SEQ ID NO: 49 |
| M44 (1-50) | AESRSVSQGS VSLELYDKLS DENDILREKQ DEYLTKIDGL DKENKEYASQ | 251-300 of Protein 3 (SEQ ID NO: 3) | SEQ ID NO: 50 |
| M78 (1-50) | ESQNSRSITN EQLIDKLVEE NNDLKEERAK YLDLLDNREK DPQYRALMGE | 301-350 of Protein 3 (SEQ ID NO: 3) | SEQ ID NO: 51 |
| M118 (1-50) | AEKKVEVADS NASSVAKLYN QIADLTDKNG EYLERIEELE ERQKNLEKLE | 351-400 of Protein 3 (SEQ ID NO: 3) | SEQ ID NO: 52 |
| M83.1 (1-50) | DNPRYTDAHN AVTQGRTVPL QNLLHEMDKN GKLRSENEEL KADLQKKEQE | 1-50 and 351-400 of Protein 4 (SEQ ID NO: 4) | SEQ ID NO: 53 |
| M82 (1-50) | DSSSRDITEA GVSKFWKSKF DAEQNRANEL EKKLSGYEKD YKTLEQEYEN | 51-100 of Protein 4 (SEQ ID NO: 4) | SEQ ID NO: 54 |
| M81 (1-50) | AGSEENVPKQ QYNALWEENE DLRGRERKYI AKLEKEEIQN GELNEKNRKL | 101-150 of Protein 4 (SEQ ID NO: 4) | SEQ ID NO: 55 |
| M87 (1-50) | ESPREVTNEL AASVWKKKVE EAKEKASKLE KQLEEAQKDY SEIEGKLEQF | 151-200 of Protein 4 (SEQ ID NO: 4) | SEQ ID NO: 56 |
| M49.1 (1-50) | VEKKVEAAEN NVSSVARREK ELYDQIADLT DKNGEYLERI GELEERQKNL | 201-250 of Protein 4 (SEQ NO: NO:) | SEQ ID NO: 57 |
| M92 (1-50) | DDRSVSTNSG SVSTPYNNLL NEYDDLLAKH GELLSEYDAL KEKQDKNQEE | 251-300 of Protein 4 (SEQ ID NO: 4) | SEQ ID NO: 58 |
| M114 (1-50) | NSKNPAPAPA SAVPVKKEAT KLSEAELYNK IQELEEGKAE LFDKLEKVEE | 301-350 of Protein 4 (SEQ ID NO: 4) | SEQ ID NO: 59 |

Example 3

Immunogenicity of Multivalent GAS Peptide Compositions

This example describes studies performed to characterize the immunological properties of the multivalent immunogenic compositions.

Vaccine formulation and immunization of rabbits. The four vaccine fusion polypeptides were mixed in equimolar amounts and adsorbed to alum (REHYDRAGEL®, low viscosity, Reheis, Inc., Berkeley Heights, N.J.). Vaccines were formulated so that each 0.5 ml dose contained 200 μg, 400 μg, 800 or 1000 μg of protein and approximately equal amounts of alum by weight. Groups of three New Zealand white rabbits were immunized with the four vaccine doses via the intramuscular route at 0, 4, and 8 weeks according to described protocols (see, e.g., Dale, *Vaccine* 17:193-200 (1999)). Serum was obtained prior to the first injection and two weeks after the final injection.

Detection of type-specific antibodies. ELISAs were performed using preimmune and immune rabbit sera by methods previously described (see, e.g., Dale, *Vaccine* 17:193-200 (1999)). The purified recombinant dimeric M peptides or synthetic peptides comprising the vaccine peptides were used as solid-phase antigens.

Assays for tissue cross-reactive antibodies. Immune sera were tested for the presence of tissue cross-reactive antibodies by indirect immunofluorescence assays using frozen sections of human heart, brain, and kidney by methods previously described (see, e.g., McNeil et al., supra).

Figure 3:
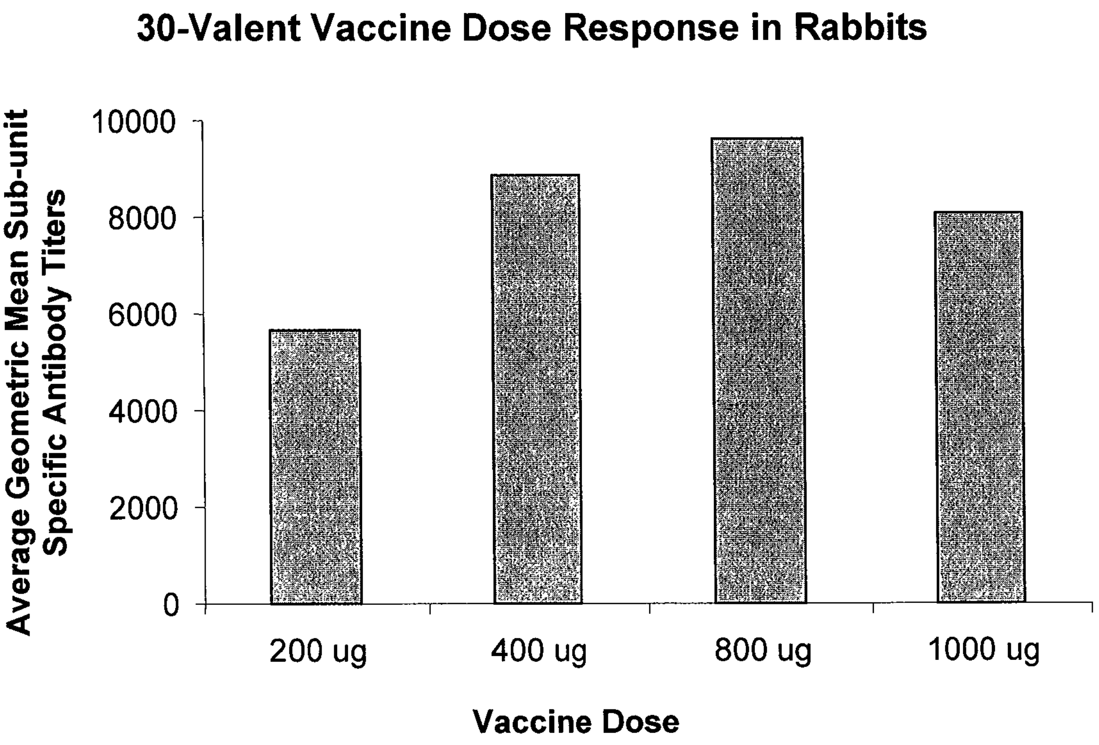
FIG. 3 depicts dose response in rabbits of the level of the antibody titer in animals immunized with the 30-valent immunogenic composition described herein.
Figure 4:
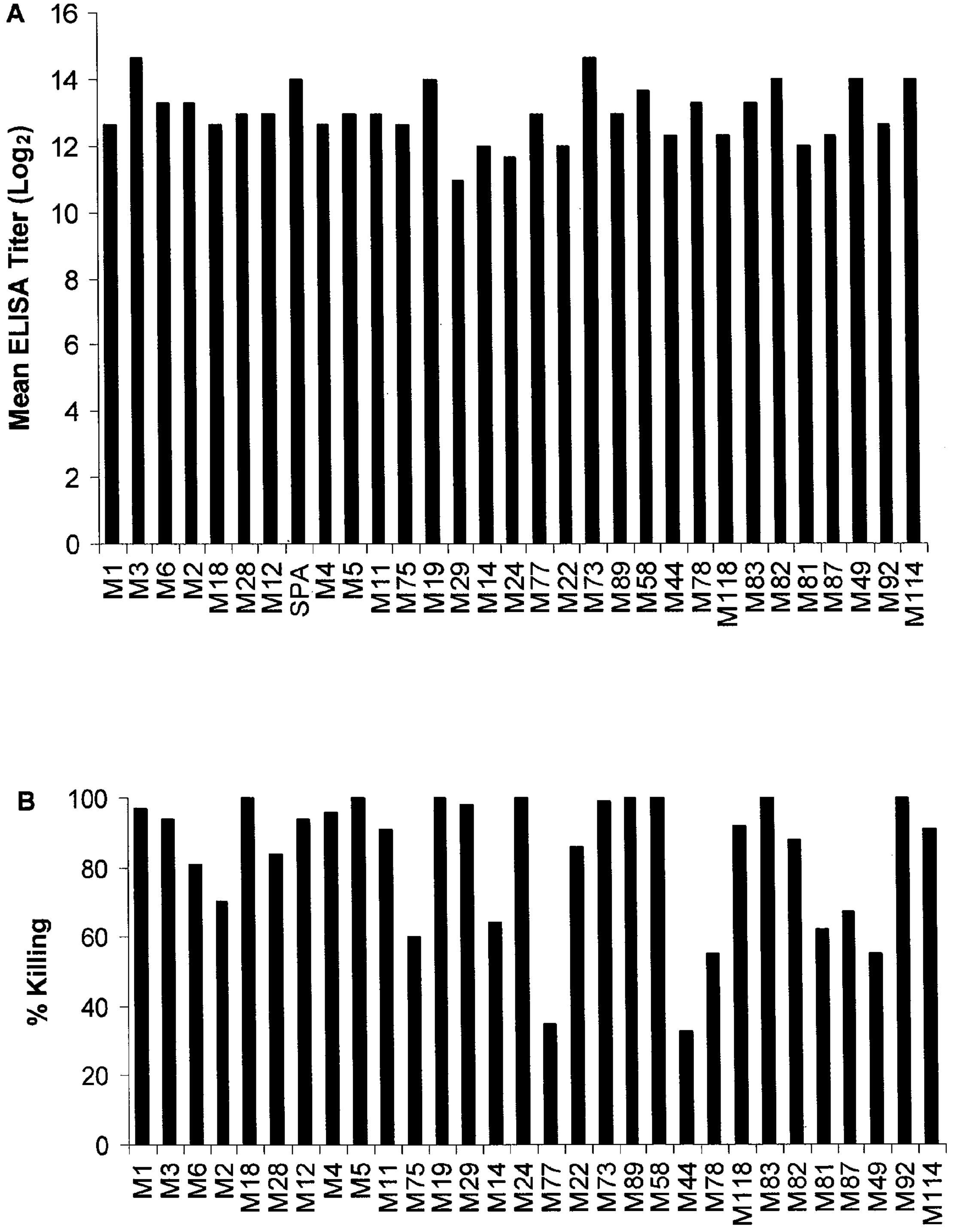
FIG. 4A-B illustrates the geometric mean antibody levels ($Log_2$) evoked in three rabbits after immunization with three 800 μg doses of the 30-valent GAS immunogenic composition. Solid-phase bound antigens were recombinant dimeric peptides or synthetic peptides (M44, M78, M118, M83, M81, M87, M49) that were used and that had the same amino acid sequence as the respective peptide used in the 30-valent GAS immunogenic composition.

The four recombinant vaccine proteins that comprised the 30-valent vaccine were purified and formulated on alum in four different concentrations. Dose response studies were conducted using sets of three rabbits that received three injections of 200 μg, 400 μg, 800 μg or 1,000 μg at times 0, 4 weeks and 8 weeks. Sera obtained 2 weeks after the final injection were assayed by ELISA using the vaccine subunit peptides as test antigens. Recombinant dimeric peptides or synthetic peptides were used as the source for the antigens bound to the plate. Synthetic peptides used in the assay were M44, M78, M118, M83, M81, M87, and M49 peptides. A dose-response was determined by calculating the average geometric mean antibody titer for the three antisera against the vaccine subunit peptides: 200 μg dose group=5651 average antibody titer, 400 μg=8868, 800 μg=9619, and 1,000 μg=8071. A graph depicting these data is provided in FIG. 3. None of the immune sera contained antibodies that cross-reacted with human brain, kidney or heart, as determined by indirect immunofluorescence assays. Based on the dose-response curve, all subsequent experiments were performed using antisera from rabbits that received the 800 μg dose of vaccine, which was highly immunogenic and evoked significant levels of antibodies against each subunit peptide contained in the vaccine as shown in FIG. 4A.

Indirect bactericidal tests. Bactericidal assays were performed as previously described (see, e.g., Hu et al., supra). Briefly, 0.05 ml of Todd-Hewitt broth containing bacteria were added to 0.1 ml of test serum and 0.35 ml of blood and the mixture was rotated for three hours at 37° C. Then 0.1 ml aliquots of this mixture were added to melted sheep's blood agar, pour plates were prepared, and viable organisms (CFU) were counted after overnight incubation at 37° C. For each serotype tested, three different inocula were used to assure that the growth in blood containing preimmune serum was optimal and quantifiable. The results were expressed as percent killing, which was calculated using the following formula: [(CFU after three hours growth with preimmune serum)−(CFU after three hours growth with immune serum) ÷CFU after three hours growth with preimmune serum]×100. Only those assays that resulted in growth of the test strain to at least seven generations in the presence of preimmune serum were used to express percent killing in the presence of immune serum.

The 800 μg dose of vaccine elicited significant levels of bactericidal antibodies against the vaccine serotypes of GAS, as determined by in vitro opsonophagocytic killing assays in whole human blood. Results are presented in FIG. 4B. Bactericidal killing of >50% was observed with 28/30 vaccine serotypes of GAS using serum from one of the immunized rabbits. With respect to the two vaccine serotypes with less than 50% killing, bactericidal killing was between 35-40% (see FIG. 4B, GAS M serotypes 77 and 44). The average killing observed against all vaccine serotypes was 83%.

Example 4

Bactericidal Activity of Immune Sera Against Non-Vaccine Serotypes

This example describes that the immune sera from animals immunized with the 30-valent vaccine composition exhibited bactericidal activity against GAS serotypes not represented in the vaccine. These data are contrasted with data obtained using immune sera obtained from animals immunized with a previously described 26-valent vaccine.

The GAS M serotypes represented in the 30-valent vaccine that were not contained in the 26-valent vaccine are M4, M29, M73, M58, M44, M78, M118, M82, M83, M81, M87, and M49. Serotypes represented in the 26-valent vaccine that are not components of the 30-valent vaccine are M1.2, M43, M13, M59, M33, M101, and M76. See Hu et al., supra; U.S. Pat. No. 7,270,827. Certain serotypes, such as M1 serotype, were subtyped prior to the currently used emm-typing system (see Facklam et al., *Emerg. Infect. Dis.* 5:247-53 (1999)). The serotype designated M1.2 has significant amino acid variation from serotype M1.0 and under the newer typing criteria would likely not be considered an M1 serotype (see, e.g., Dale et al., *Clin. Diagn. Lab. Immunol.* 12:833-36 (2005)).

Bactericidal Activity of Antisera Against Non-vaccine Serotypes

Figure 5A:
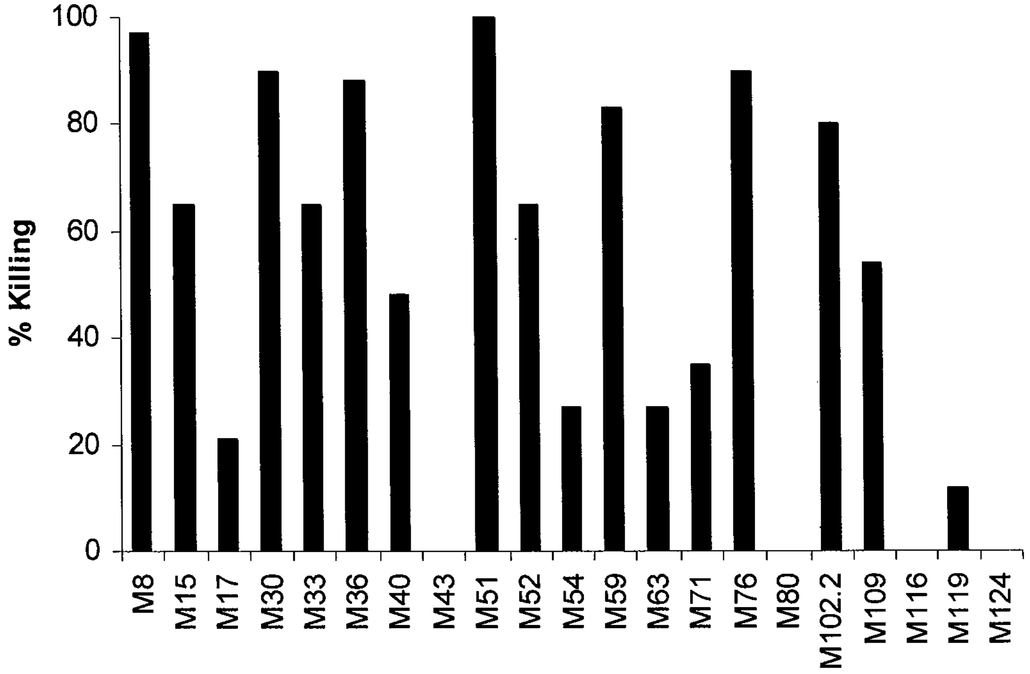
FIG. 5A-B illustrates the level of bactericidal antibodies evoked by a 30-valent immunogenic composition against serotypes of GAS not represented by a GAS peptide in the 30-valent immunogenic composition.

Bactericidal assays were performed as described in Example 3. The immune sera against the 30-valent vaccine (see Example 3) were also used in indirect bactericidal assays against a panel of GAS serotypes that were not represented in the vaccine. In a first experiment as shown in FIG. 5A, bactericidal activity of >50% was observed against 11/21 serotypes randomly selected from an internal laboratory collection. The average observed for the 11 serotypes that displayed >50% killing was 80% killing and for all 21 serotypes tested was 50%. The immune sera lacked bactericidal activity against only 4 of the 21 non-vaccine serotypes tested.

Figure 5B:
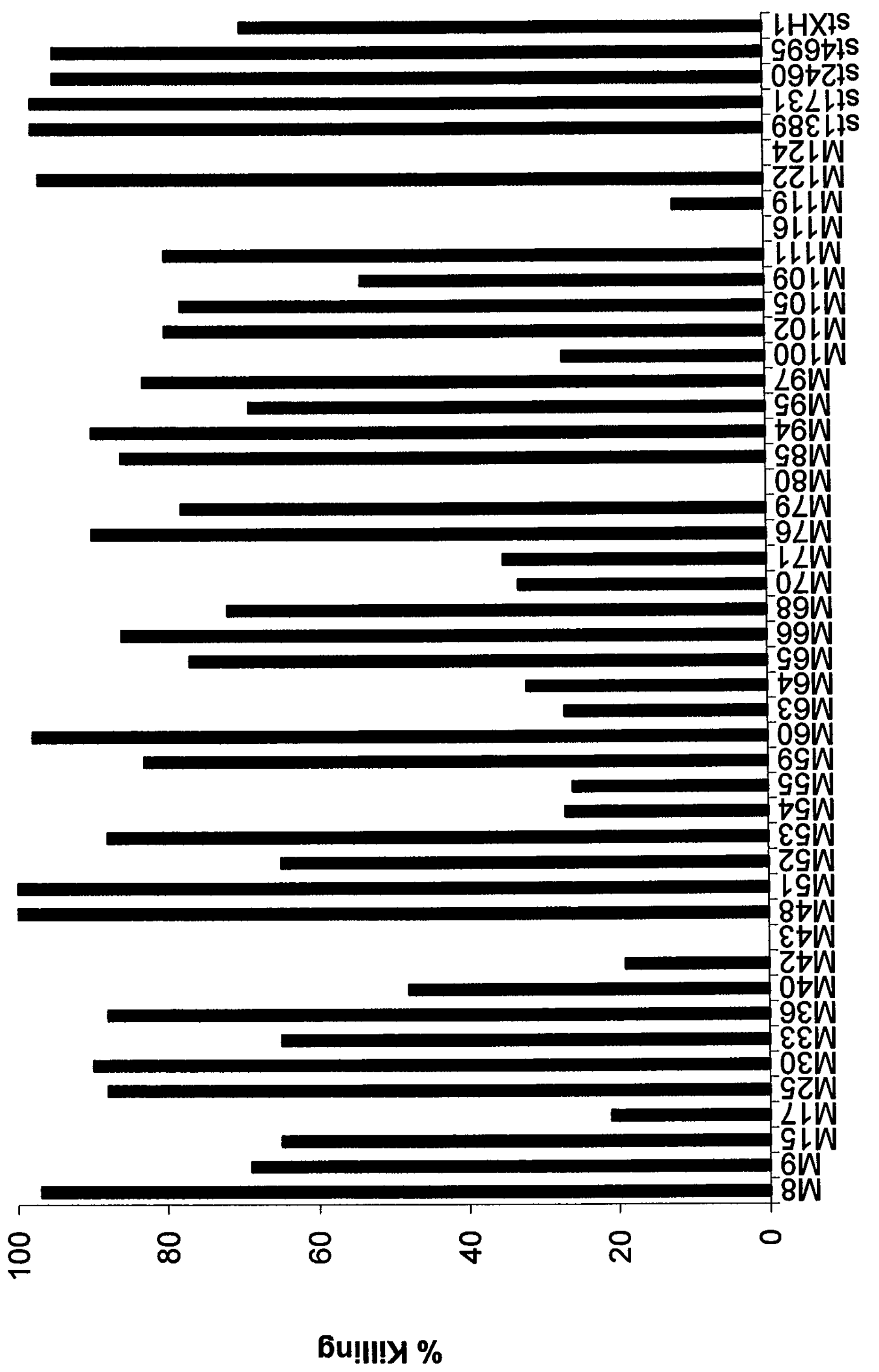

In a second experiment, a greater number of GAS serotypes not represented in the vaccine were included in a bactericidal activity assay. As shown in FIG. 5B, bactericidal activity of >50% was observed against 33/47 serotypes selected from the laboratory collection. The average observed for the 33 serotypes that displayed >50% killing was 80% killing and for all 47 serotypes tested was 63%. The immune sera lacked bactericidal activity against only 4 of the 47 non-vaccine serotypes tested.

Figure 6:
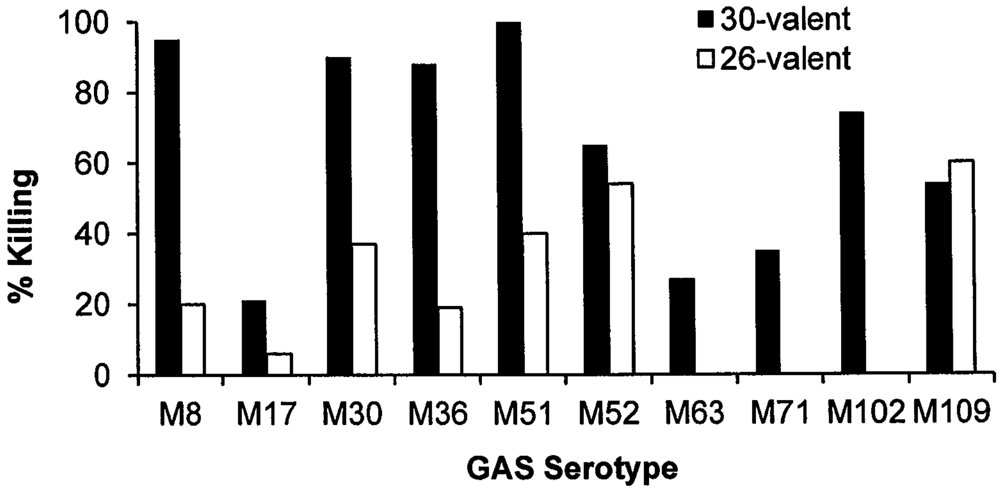
FIG. 6 presents a comparison of cross-opsonic bactericidal antibodies evoked by the 30-valent immunogenic composition vs. a 26-valent vaccine (see, e.g., Hu et al., supra; U.S. Pat. No. 7,270,827). The level of bactericidal killing promoted by the 30-valent immunogenic composition against 10 serotypes that were not represented in any of the fusion polypeptide constructs was significantly greater than bactericidal killing observed with the 26-valent antiserum (average 64.9% vs. 23.6%, p=0.0008, Student's t-test, paired, two-tailed).

Comparison of bactericidal antibody activity evoked by the 30-valent vs. the 26-valent vaccine against non-vaccine serotypes. To determine if the cross-opsonic antibodies evoked by the 30-valent vaccine could potentially afford broader protection against infections then the previously reported 26-valent vaccine (see Hu et al., supra; U.S. Pat. No. 7,270,827), bactericidal assays were performed with both antisera in the same experiment. Twenty-one GAS serotypes not included in either the 30-valent or 26-valent vaccines were randomly chosen for inclusion in this experiment. The results are presented in FIG. 6. The level of bactericidal killing promoted by the 30-valent vaccine against 10 serotypes that were not represented in either vaccine construct was significantly greater than that observed with the 26-valent antiserum (average 64.9% vs. 23.6%, p=0.0008, Student's t-test, paired, two-tailed).

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference, in their entirety. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

I claim the following:

1. An immunogenic composition comprising at least 31 immunogenic peptides, wherein each immunogenic peptide is different and comprises at least 25 contiguous amino acids from the amino terminal portion of a different M protein or Spa protein, wherein each different M protein is independently selected from the M protein of group A *streptococcus* (GAS) serotype 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118, and the Spa protein is from GAS serotype 18, wherein the immunogenic composition comprises a first fusion polypeptide, a second fusion polypeptide, a third fusion polypeptide, and a fourth fusion polypeptide that each comprises at least six of the different immunogenic peptides linked in tandem, wherein the first fusion polypeptide comprises eight of the different immunogenic peptides linked in tandem, wherein each of the eight immunogenic peptides comprises at least 25 contiguous amino acids from the amino terminal portion of a different M protein or the Spa protein, wherein each different M protein is independently selected from the M protein of GAS serotype 1, 2, 3, 6, 12, 18, and 28, and the Spa protein is from GAS serotype 18;

wherein the second fusion polypeptide comprises eight of the different immunogenic peptides linked in tandem, and wherein each of the eight immunogenic peptides comprises at least 25 contiguous amino acids from the amino terminal portion of a different M protein independently selected from the M protein of GAS serotype 4, 5, 11, 14, 19, 24, 29, and 75;

wherein the third fusion polypeptide comprises eight of the different immunogenic peptides linked in tandem, and wherein each of the eight immunogenic peptides comprises at least 25 contiguous amino acids from the amino terminal portion of a different M protein independently selected from the M protein of GAS serotype 22, 44, 58, 73, 77, 78, 89, and 118;

wherein the fourth fusion polypeptide comprises seven of the different immunogenic peptides linked in tandem, and wherein each of the seven immunogenic peptides comprises at least 25 contiguous amino acids from the amino terminal portion of a different M protein independently selected from the M protein of GAS serotype 49, 81, 82, 83, 87, 92, and 114, and wherein the immunogenic composition induces an immune response against GAS.

2. The immunogenic composition of claim 1, wherein the immunogenic peptide located at the carboxy terminal end of the first fusion polypeptide is a duplicate of the immunogenic peptide located at the amino terminal end of the first fusion polypeptide.

3. The immunogenic composition of claim 2, wherein the immunogenic peptide that is duplicated comprises at least 25 contiguous amino acids from the amino terminal portion of the M protein of GAS serotype 1.

4. The immunogenic composition of claim 1, wherein the immunogenic peptide located at the carboxy terminal end of the second fusion polypeptide is a duplicate of the immunogenic peptide located at the amino terminal end of the second fusion polypeptide.

5. The immunogenic composition of claim 4, wherein the immunogenic peptide that is duplicated comprises at least 25 contiguous amino acids from the amino terminal portion of the M protein of GAS serotype 4.

6. The immunogenic composition of claim 1, wherein the immunogenic peptide located at the carboxy terminal end of the third fusion polypeptide is a duplicate of the immunogenic peptide located at the amino terminal end of the third fusion polypeptide.

7. The immunogenic composition of claim 6, wherein the immunogenic peptide that is duplicated comprises at least 25 contiguous amino acids from the amino terminal portion of the M protein of GAS serotype 77.

8. The immunogenic composition of claim 1, wherein the immunogenic peptide located at the carboxy terminal end of the fourth fusion polypeptide is a duplicate of the immunogenic peptide located at the amino terminal end of the fourth fusion polypeptide.

9. The immunogenic composition of claim 8, wherein the immunogenic peptide that is duplicated comprises at least 25 contiguous amino acids from the amino terminal portion of the M protein of GAS serotype 83.

10. The immunogenic composition of claim 1, wherein one or more of the immunogenic peptides comprises the at least 25 contiguous amino acids from the amino terminal portion of the different M protein or the Spa protein in duplicate.

11. The immunogenic composition of claim 1, further comprising a pharmaceutically acceptable excipient.

12. The immunogenic composition of claim 11, further comprising a pharmaceutically acceptable adjuvant.

13. The immunogenic composition of claim 1, wherein the immune response against group A *streptococcus* comprises an immune response against at least each of GAS 1, 2, 3, 4, 5, 6, 11, 12, 14, 18, 19, 22, 24, 28, 29, 44, 49, 58, 73, 75, 77, 78, 81, 82, 83, 87, 89, 92, 114, and 118 serotypes.

14. The immunogenic composition of claim 1, wherein one or more of the immunogenic peptides comprises at least 40 contiguous amino acids from the amino terminal portion of the different M protein or the Spa protein.

15. The immunogenic composition of claim 1, wherein one or more of the immunogenic peptides comprises at least 45 contiguous amino acids from the amino terminal portion of the different M protein or the Spa protein.

16. The immunogenic composition of claim 1, wherein one or more of the immunogenic peptides comprises at least 50 contiguous amino acids from the amino terminal portion of the different M protein or the Spa protein.

17. A method for inducing an immune response against group A *streptococcus* in a subject, comprising administering to the subject the immunogenic composition of claim 1.

* * * * *

SEQUENCE LISTING

<160> NUMBER OF SEQ ID NOS: 61

<210> SEQ ID NO 1
<211> LENGTH: 450
<212> TYPE: PRT
<213> ORGANISM: Artificial Sequence
<220> FEATURE:
<223> OTHER INFORMATION: Fusion protein of group A streptococcus M
      proteins.

<400> SEQUENCE: 1

Asn Gly Asp Gly Asn Pro Arg Glu Val Ile Glu Asp Leu Ala Ala Asn
1               5                   10                  15

Asn Pro Ala Ile Gln Asn Ile Arg Leu Arg His Glu Asn Lys Asp Leu
            20                  25                  30

Lys Ala Arg Leu Glu Asn Ala Met Glu Val Ala Gly Arg Asp Phe Lys
        35                  40                  45

Arg Ala Leu Leu Asp Gln Val Thr Gln Leu Tyr Thr Lys His Asn Ser
    50                  55                  60

Asn Tyr Gln Gln Tyr Asn Ala Gln Ala Gly Arg Leu Asp Leu Arg Gln
65                  70                  75                  80

Lys Ala Glu Tyr Leu Lys Gly Leu Asn Asp Trp Ala Glu Arg Leu Leu
                85                  90                  95

Gln Glu Leu Asn Arg Val Phe Pro Arg Gly Thr Val Glu Asn Pro Asp
            100                 105                 110

Lys Ala Arg Glu Leu Leu Asn Lys Tyr Asp Val Glu Asn Arg Val Phe
        115                 120                 125

Pro Arg Gly Thr Val Glu Asn Pro Asp Lys Ala Arg Glu Leu Leu Asn
    130                 135                 140

Lys Tyr Asp Val Glu Asn Ser Lys Asn Pro Val Pro Val Lys Lys Glu
145                 150                 155                 160

Ala Lys Leu Ser Glu Ala Glu Leu His Asp Lys Ile Lys Asn Leu Ser
                165                 170                 175

Lys Asn Pro Val Pro Val Lys Lys Glu Ala Lys Leu Ser Glu Ala Glu
            180                 185                 190

Leu His Asp Lys Ile Lys Asn Leu Ala Pro Leu Thr Arg Ala Thr Ala
        195                 200                 205

Asp Asn Lys Asp Glu Leu Ile Lys Arg Ala Asn Asp Tyr Glu Ile Gln
    210                 215                 220

Asn His Gln Leu Thr Val Glu Asn Lys Lys Leu Lys Thr Asp Lys Glu
225                 230                 235                 240

Gln Leu Thr Lys Glu Asn Asp Asp Leu Lys Ala Glu Ser Pro Lys Ser
                245                 250                 255

Thr Glu Thr Ser Ala Asn Gly Ala Asp Lys Leu Ala Asp Ala Tyr Asn
            260                 265                 270

Thr Leu Leu Thr Glu His Glu Lys Leu Arg Asp Glu Tyr Tyr Thr Leu
        275                 280                 285

Ile Asp Ala Lys Glu Glu Glu Pro Arg Tyr Lys Ala Asp His Ser Asp
    290                 295                 300

Leu Val Ala Glu Lys Gln Arg Leu Glu Asp Leu Gly Gln Lys Phe Glu
305                 310                 315                 320

Arg Leu Lys Gln Arg Ser Glu Leu Tyr Leu Gln Gln Tyr Tyr Asp Asn
                325                 330                 335

Lys Ser Asn Gly Tyr Lys Gly Asp Trp Tyr Val Gln Gln Leu Asp Ser
            340                 345                 350

-continued

```
Val Ser Gly Leu Glu Val Ala Asp Pro Ser Asp Ser Lys Lys Leu Ile
        355                 360                 365

Glu Leu Gly Leu Ala Lys Tyr Leu Asn Asp Lys Leu Pro Phe Lys Thr
    370                 375                 380

Lys Glu Asp Ser Glu Ile Leu Ser Glu Leu Arg Asp Val Leu Lys Asn
385                 390                 395                 400

Asn Gly Asp Gly Asn Pro Arg Glu Val Ile Glu Asp Leu Ala Ala Asn
                405                 410                 415

Asn Pro Ala Ile Gln Asn Ile Arg Leu Arg His Glu Asn Lys Asp Leu
            420                 425                 430

Lys Ala Arg Leu Glu Asn Ala Met Glu Val Ala Gly Arg Asp Phe Lys
        435                 440                 445

Arg Ala
    450


<210> SEQ ID NO 2
<211> LENGTH: 450
<212> TYPE: PRT
<213> ORGANISM: Artificial Sequence
<220> FEATURE:
<223> OTHER INFORMATION: Fusion protein of group A streptococcus M
      proteins.

<400> SEQUENCE: 2

Ala Glu Ile Lys Lys Pro Gln Ala Asp Ser Ala Trp Asn Trp Pro Lys
1               5                   10                  15

Glu Tyr Asn Ala Leu Leu Lys Glu Asn Glu Glu Leu Lys Val Glu Arg
            20                  25                  30

Glu Lys Tyr Leu Ser Tyr Ala Asp Asp Lys Glu Lys Asp Pro Gln Tyr
        35                  40                  45

Arg Ala Ala Val Thr Arg Gly Thr Ile Asn Asp Pro Gln Arg Ala Lys
    50                  55                  60

Glu Ala Leu Asp Lys Tyr Glu Leu Glu Asn His Ala Val Thr Arg Gly
65                  70                  75                  80

Thr Ile Asn Asp Pro Gln Arg Ala Lys Glu Ala Leu Asp Lys Tyr Glu
                85                  90                  95

Leu Glu Asn His Thr Glu Val Lys Ala Ala Gly Gln Ser Ala Pro Lys
            100                 105                 110

Gly Thr Asn Val Ser Ala Asp Leu Tyr Asn Ser Leu Trp Asp Glu Asn
        115                 120                 125

Lys Thr Leu Arg Glu Lys Gln Glu Glu Tyr Ile Thr Lys Ile Gln Asn
    130                 135                 140

Glu Glu Thr Lys Asn Lys Glu Glu Glu Arg Thr Phe Thr Glu Leu Pro
145                 150                 155                 160

Tyr Glu Ala Arg Tyr Lys Ala Trp Lys Ser Glu Asn Asp Glu Leu Arg
                165                 170                 175

Glu Asn Tyr Arg Arg Thr Leu Asp Lys Phe Asn Thr Glu Gln Gly Lys
            180                 185                 190

Thr Thr Arg Leu Glu Glu Gln Asn Arg Val Arg Tyr Thr Arg His Thr
        195                 200                 205

Pro Glu Asp Lys Leu Lys Lys Ile Ile Asp Asp Leu Asp Ala Lys Glu
    210                 215                 220

His Arg Val Arg Tyr Thr Arg His Thr Pro Glu Asp Lys Leu Lys Lys
225                 230                 235                 240

Ile Ile Asp Asp Leu Asp Ala Lys Glu His Arg Val Tyr Ile Thr Arg
                245                 250                 255
```

Arg Met Thr Lys Glu Asp Val Glu Lys Ile Ala Asn Asp Leu Asp Thr
260 265 270

Glu Asn His Gly Leu Lys Gln Gln Asn Glu Gln Leu Ser Thr Glu Lys
275 280 285

Gln Gly Leu Glu Glu Gln Asn Lys Gln Leu Ser Thr Asp Arg Val Ser
290 295 300

Arg Ser Met Ser Arg Asp Asp Leu Leu Asn Arg Ala Gln Asp Leu Glu
305 310 315 320

Ala Lys Asn His Gly Leu Glu His Gln Asn Thr Lys Leu Ser Thr Glu
325 330 335

Asn Lys Thr Leu Gln Glu Gln Ala Glu Ala Arg Gln Lys Glu Val Ala
340 345 350

Thr Arg Ser Gln Thr Asp Thr Leu Glu Lys Val Gln Glu Arg Ala Asp
355 360 365

Lys Phe Glu Ile Glu Asn Asn Thr Leu Lys Leu Lys Asn Ser Asp Leu
370 375 380

Ser Phe Asn Asn Lys Ala Leu Lys Asp His Asn Asp Glu Leu Thr Glu
385 390 395 400

Ala Glu Ile Lys Lys Pro Gln Ala Asp Ser Ala Trp Asn Trp Pro Lys
405 410 415

Glu Tyr Asn Ala Leu Leu Lys Glu Asn Glu Glu Leu Lys Val Glu Arg
420 425 430

Glu Lys Tyr Leu Ser Tyr Ala Asp Asp Lys Glu Lys Asp Pro Gln Tyr
435 440 445

Arg Ala
450

<210> SEQ ID NO 3
<211> LENGTH: 450
<212> TYPE: PRT
<213> ORGANISM: Artificial Sequence
<220> FEATURE:
<223> OTHER INFORMATION: Fusion protein of group A streptococcus M proteins.

<400> SEQUENCE: 3

Glu Gly Val Ser Val Gly Ser Asp Ala Ser Leu His Asn Arg Ile Thr
1 5 10 15

Asp Leu Glu Glu Glu Arg Glu Lys Leu Leu Asn Lys Leu Asp Lys Val
20 25 30

Glu Glu Glu His Lys Lys Asp His Glu Gln Leu Glu Lys Lys Ser Glu
35 40 45

Asp Val Glu Ser Ser Asn Asn Ala Glu Ser Ser Asn Ile Ser Gln Glu
50 55 60

Ser Lys Leu Ile Asn Thr Leu Thr Asp Glu Asn Glu Lys Leu Arg Glu
65 70 75 80

Glu Leu Gln Gln Tyr Tyr Ala Leu Ser Asp Ala Lys Glu Glu Glu Pro
85 90 95

Arg Tyr Lys Ala Asp Asn Gln Ser Pro Ala Pro Val Lys Lys Glu Ala
100 105 110

Lys Lys Leu Asn Glu Ala Glu Leu Tyr Asn Lys Ile Gln Glu Leu Glu
115 120 125

Glu Gly Lys Ala Glu Leu Phe Asp Lys Leu Glu Lys Val Glu Glu Glu
130 135 140

Asn Lys Lys Val Lys Glu Asp Ser Asp Asn Ile Asn Arg Ser Val Ser
145 150 155 160

```
Val Lys Asp Asn Glu Lys Glu Leu His Asn Lys Ile Ala Asp Leu Glu
                165                 170                 175

Glu Glu Arg Gly Glu His Leu Asp Lys Ile Asp Glu Leu Lys Glu Glu
            180                 185                 190

Leu Lys Ala Lys Glu Lys Ser Ser Asp Ser Ser Arg Glu Val Thr Asn
        195                 200                 205

Glu Leu Thr Ala Ser Met Trp Lys Ala Gln Ala Asp Ser Ala Lys Ala
    210                 215                 220

Lys Ala Lys Glu Leu Glu Lys Gln Val Glu Glu Tyr Lys Lys Asn Tyr
225                 230                 235                 240

Glu Thr Leu Glu Lys Gly Tyr Asp Asp Leu Ala Glu Ser Arg Ser Val
                245                 250                 255

Ser Gln Gly Ser Val Ser Leu Glu Leu Tyr Asp Lys Leu Ser Asp Glu
            260                 265                 270

Asn Asp Ile Leu Arg Glu Lys Gln Asp Glu Tyr Leu Thr Lys Ile Asp
        275                 280                 285

Gly Leu Asp Lys Glu Asn Lys Glu Tyr Ala Ser Gln Glu Ser Gln Asn
    290                 295                 300

Ser Arg Ser Ile Thr Asn Glu Gln Leu Ile Asp Lys Leu Val Glu Glu
305                 310                 315                 320

Asn Asn Asp Leu Lys Glu Glu Arg Ala Lys Tyr Leu Asp Leu Leu Asp
                325                 330                 335

Asn Arg Glu Lys Asp Pro Gln Tyr Arg Ala Leu Met Gly Glu Ala Glu
            340                 345                 350

Lys Lys Val Glu Val Ala Asp Ser Asn Ala Ser Ser Val Ala Lys Leu
        355                 360                 365

Tyr Asn Gln Ile Ala Asp Leu Thr Asp Lys Asn Gly Glu Tyr Leu Glu
    370                 375                 380

Arg Ile Glu Glu Leu Glu Glu Arg Gln Lys Asn Leu Glu Lys Leu Glu
385                 390                 395                 400

Glu Gly Val Ser Val Gly Ser Asp Ala Ser Leu His Asn Arg Ile Thr
                405                 410                 415

Asp Leu Glu Glu Glu Arg Glu Lys Leu Leu Asn Lys Leu Asp Lys Val
            420                 425                 430

Glu Glu Glu His Lys Lys Asp His Glu Gln Leu Glu Lys Lys Ser Glu
        435                 440                 445

Asp Val
    450
```

<210> SEQ ID NO 4
<211> LENGTH: 400
<212> TYPE: PRT
<213> ORGANISM: Artificial Sequence
<220> FEATURE:
<223> OTHER INFORMATION: Fusion protein of group A streptococcus M proteins.

<400> SEQUENCE: 4

```
Asp Asn Pro Arg Tyr Thr Asp Ala His Asn Ala Val Thr Gln Gly Arg
1               5                   10                  15

Thr Val Pro Leu Gln Asn Leu Leu His Glu Met Asp Lys Asn Gly Lys
            20                  25                  30

Leu Arg Ser Glu Asn Glu Glu Leu Lys Ala Asp Leu Gln Lys Lys Glu
        35                  40                  45

Gln Glu Asp Ser Ser Ser Arg Asp Ile Thr Glu Ala Gly Val Ser Lys
    50                  55                  60
```

```
Phe Trp Lys Ser Lys Phe Asp Ala Glu Gln Asn Arg Ala Asn Glu Leu
65                  70                  75                  80

Glu Lys Lys Leu Ser Gly Tyr Glu Lys Asp Tyr Lys Thr Leu Glu Gln
                85                  90                  95

Glu Tyr Glu Asn Ala Gly Ser Glu Glu Asn Val Pro Lys Gln Gln Tyr
            100                 105                 110

Asn Ala Leu Trp Glu Glu Asn Glu Asp Leu Arg Gly Arg Glu Arg Lys
        115                 120                 125

Tyr Ile Ala Lys Leu Glu Lys Glu Glu Ile Gln Asn Gly Glu Leu Asn
    130                 135                 140

Glu Lys Asn Arg Lys Leu Glu Ser Pro Arg Glu Val Thr Asn Glu Leu
145                 150                 155                 160

Ala Ala Ser Val Trp Lys Lys Lys Val Glu Glu Ala Lys Glu Lys Ala
                165                 170                 175

Ser Lys Leu Glu Lys Gln Leu Glu Glu Ala Gln Lys Asp Tyr Ser Glu
            180                 185                 190

Ile Glu Gly Lys Leu Glu Gln Phe Val Glu Lys Lys Val Glu Ala Ala
        195                 200                 205

Glu Asn Asn Val Ser Ser Val Ala Arg Arg Glu Lys Glu Leu Tyr Asp
    210                 215                 220

Gln Ile Ala Asp Leu Thr Asp Lys Asn Gly Glu Tyr Leu Glu Arg Ile
225                 230                 235                 240

Gly Glu Leu Glu Glu Arg Gln Lys Asn Leu Asp Asp Arg Ser Val Ser
                245                 250                 255

Thr Asn Ser Gly Ser Val Ser Thr Pro Tyr Asn Asn Leu Leu Asn Glu
            260                 265                 270

Tyr Asp Asp Leu Leu Ala Lys His Gly Glu Leu Leu Ser Glu Tyr Asp
        275                 280                 285

Ala Leu Lys Glu Lys Gln Asp Lys Asn Gln Glu Glu Asn Ser Lys Asn
    290                 295                 300

Pro Ala Pro Ala Pro Ala Ser Ala Val Pro Val Lys Lys Glu Ala Thr
305                 310                 315                 320

Lys Leu Ser Glu Ala Glu Leu Tyr Asn Lys Ile Gln Glu Leu Glu Glu
                325                 330                 335

Gly Lys Ala Glu Leu Phe Asp Lys Leu Glu Lys Val Glu Glu Asp Asn
            340                 345                 350

Pro Arg Tyr Thr Asp Ala His Asn Ala Val Thr Gln Gly Arg Thr Val
        355                 360                 365

Pro Leu Gln Asn Leu Leu His Glu Met Asp Lys Asn Gly Lys Leu Arg
    370                 375                 380

Ser Glu Asn Glu Glu Leu Lys Ala Asp Leu Gln Lys Lys Glu Gln Glu
385                 390                 395                 400
```

<210> SEQ ID NO 5
<211> LENGTH: 451
<212> TYPE: PRT
<213> ORGANISM: Artificial Sequence
<220> FEATURE:
<223> OTHER INFORMATION: Fusion protein of group A streptococcus M proteins.

<400> SEQUENCE: 5

```
Met Asn Gly Asp Gly Asn Pro Arg Glu Val Ile Glu Asp Leu Ala Ala
1               5                   10                  15

Asn Asn Pro Ala Ile Gln Asn Ile Arg Leu Arg His Glu Asn Lys Asp
            20                  25                  30
```

-continued

```
Leu Lys Ala Arg Leu Glu Asn Ala Met Glu Val Ala Gly Arg Asp Phe
        35                  40                  45

Lys Arg Ala Leu Leu Asp Gln Val Thr Gln Leu Tyr Thr Lys His Asn
    50                  55                  60

Ser Asn Tyr Gln Gln Tyr Asn Ala Gln Ala Gly Arg Leu Asp Leu Arg
65                  70                  75                  80

Gln Lys Ala Glu Tyr Leu Lys Gly Leu Asn Asp Trp Ala Glu Arg Leu
                85                  90                  95

Leu Gln Glu Leu Asn Arg Val Phe Pro Arg Gly Thr Val Glu Asn Pro
            100                 105                 110

Asp Lys Ala Arg Glu Leu Leu Asn Lys Tyr Asp Val Glu Asn Arg Val
        115                 120                 125

Phe Pro Arg Gly Thr Val Glu Asn Pro Asp Lys Ala Arg Glu Leu Leu
    130                 135                 140

Asn Lys Tyr Asp Val Glu Asn Ser Lys Asn Pro Val Pro Val Lys Lys
145                 150                 155                 160

Glu Ala Lys Leu Ser Glu Ala Glu Leu His Asp Lys Ile Lys Asn Leu
                165                 170                 175

Ser Lys Asn Pro Val Pro Val Lys Lys Glu Ala Lys Leu Ser Glu Ala
            180                 185                 190

Glu Leu His Asp Lys Ile Lys Asn Leu Ala Pro Leu Thr Arg Ala Thr
        195                 200                 205

Ala Asp Asn Lys Asp Glu Leu Ile Lys Arg Ala Asn Asp Tyr Glu Ile
    210                 215                 220

Gln Asn His Gln Leu Thr Val Glu Asn Lys Lys Leu Lys Thr Asp Lys
225                 230                 235                 240

Glu Gln Leu Thr Lys Glu Asn Asp Asp Leu Lys Ala Glu Ser Pro Lys
                245                 250                 255

Ser Thr Glu Thr Ser Ala Asn Gly Ala Asp Lys Leu Ala Asp Ala Tyr
            260                 265                 270

Asn Thr Leu Leu Thr Glu His Glu Lys Leu Arg Asp Glu Tyr Tyr Thr
        275                 280                 285

Leu Ile Asp Ala Lys Glu Glu Glu Pro Arg Tyr Lys Ala Asp His Ser
    290                 295                 300

Asp Leu Val Ala Glu Lys Gln Arg Leu Glu Asp Leu Gly Gln Lys Phe
305                 310                 315                 320

Glu Arg Leu Lys Gln Arg Ser Glu Leu Tyr Leu Gln Gln Tyr Tyr Asp
                325                 330                 335

Asn Lys Ser Asn Gly Tyr Lys Gly Asp Trp Tyr Val Gln Gln Leu Asp
            340                 345                 350

Ser Val Ser Gly Leu Glu Val Ala Asp Pro Ser Asp Ser Lys Lys Leu
        355                 360                 365

Ile Glu Leu Gly Leu Ala Lys Tyr Leu Asn Asp Lys Leu Pro Phe Lys
    370                 375                 380

Thr Lys Glu Asp Ser Glu Ile Leu Ser Glu Leu Arg Asp Val Leu Lys
385                 390                 395                 400

Asn Asn Gly Asp Gly Asn Pro Arg Glu Val Ile Glu Asp Leu Ala Ala
                405                 410                 415

Asn Asn Pro Ala Ile Gln Asn Ile Arg Leu Arg His Glu Asn Lys Asp
            420                 425                 430

Leu Lys Ala Arg Leu Glu Asn Ala Met Glu Val Ala Gly Arg Asp Phe
        435                 440                 445

Lys Arg Ala
```

450

<210> SEQ ID NO 6
<211> LENGTH: 451
<212> TYPE: PRT
<213> ORGANISM: Artificial Sequence
<220> FEATURE:
<223> OTHER INFORMATION: Fusion protein of group A streptococcus M
proteins.

<400> SEQUENCE: 6

```
Met Ala Glu Ile Lys Lys Pro Gln Ala Asp Ser Ala Trp Asn Trp Pro
1               5                   10                  15

Lys Glu Tyr Asn Ala Leu Leu Lys Glu Asn Glu Glu Leu Lys Val Glu
            20                  25                  30

Arg Glu Lys Tyr Leu Ser Tyr Ala Asp Asp Lys Glu Lys Asp Pro Gln
        35                  40                  45

Tyr Arg Ala Ala Val Thr Arg Gly Thr Ile Asn Asp Pro Gln Arg Ala
    50                  55                  60

Lys Glu Ala Leu Asp Lys Tyr Glu Leu Glu Asn His Ala Val Thr Arg
65                  70                  75                  80

Gly Thr Ile Asn Asp Pro Gln Arg Ala Lys Glu Ala Leu Asp Lys Tyr
                85                  90                  95

Glu Leu Glu Asn His Thr Glu Val Lys Ala Ala Gly Gln Ser Ala Pro
            100                 105                 110

Lys Gly Thr Asn Val Ser Ala Asp Leu Tyr Asn Ser Leu Trp Asp Glu
        115                 120                 125

Asn Lys Thr Leu Arg Glu Lys Gln Glu Glu Tyr Ile Thr Lys Ile Gln
    130                 135                 140

Asn Glu Glu Thr Lys Asn Lys Glu Glu Glu Arg Thr Phe Thr Glu Leu
145                 150                 155                 160

Pro Tyr Glu Ala Arg Tyr Lys Ala Trp Lys Ser Glu Asn Asp Glu Leu
                165                 170                 175

Arg Glu Asn Tyr Arg Arg Thr Leu Asp Lys Phe Asn Thr Glu Gln Gly
            180                 185                 190

Lys Thr Thr Arg Leu Glu Glu Gln Asn Arg Val Arg Tyr Thr Arg His
        195                 200                 205

Thr Pro Glu Asp Lys Leu Lys Lys Ile Ile Asp Asp Leu Asp Ala Lys
    210                 215                 220

Glu His Arg Val Arg Tyr Thr Arg His Thr Pro Glu Asp Lys Leu Lys
225                 230                 235                 240

Lys Ile Ile Asp Asp Leu Asp Ala Lys Glu His Arg Val Tyr Ile Thr
                245                 250                 255

Arg Arg Met Thr Lys Glu Asp Val Glu Lys Ile Ala Asn Asp Leu Asp
            260                 265                 270

Thr Glu Asn His Gly Leu Lys Gln Gln Asn Glu Gln Leu Ser Thr Glu
        275                 280                 285

Lys Gln Gly Leu Glu Glu Gln Asn Lys Gln Leu Ser Thr Asp Arg Val
    290                 295                 300

Ser Arg Ser Met Ser Arg Asp Asp Leu Leu Asn Arg Ala Gln Asp Leu
305                 310                 315                 320

Glu Ala Lys Asn His Gly Leu Glu His Gln Asn Thr Lys Leu Ser Thr
                325                 330                 335

Glu Asn Lys Thr Leu Gln Glu Gln Ala Glu Ala Arg Gln Lys Glu Val
            340                 345                 350

Ala Thr Arg Ser Gln Thr Asp Thr Leu Glu Lys Val Gln Glu Arg Ala
```

```
        355                 360                 365

Asp Lys Phe Glu Ile Glu Asn Asn Thr Leu Lys Leu Lys Asn Ser Asp
    370                 375                 380

Leu Ser Phe Asn Asn Lys Ala Leu Lys Asp His Asn Asp Glu Leu Thr
385                 390                 395                 400

Glu Ala Glu Ile Lys Lys Pro Gln Ala Asp Ser Ala Trp Asn Trp Pro
                405                 410                 415

Lys Glu Tyr Asn Ala Leu Leu Lys Glu Asn Glu Glu Leu Lys Val Glu
            420                 425                 430

Arg Glu Lys Tyr Leu Ser Tyr Ala Asp Asp Lys Glu Lys Asp Pro Gln
        435                 440                 445

Tyr Arg Ala
    450


<210> SEQ ID NO 7
<211> LENGTH: 451
<212> TYPE: PRT
<213> ORGANISM: Artificial Sequence
<220> FEATURE:
<223> OTHER INFORMATION: Fusion protein of group A streptococcus M
      proteins.

<400> SEQUENCE: 7

Met Glu Gly Val Ser Val Gly Ser Asp Ala Ser Leu His Asn Arg Ile
1               5                   10                  15

Thr Asp Leu Glu Glu Glu Arg Glu Lys Leu Leu Asn Lys Leu Asp Lys
            20                  25                  30

Val Glu Glu Glu His Lys Lys Asp His Glu Gln Leu Glu Lys Lys Ser
        35                  40                  45

Glu Asp Val Glu Ser Ser Asn Asn Ala Glu Ser Ser Asn Ile Ser Gln
    50                  55                  60

Glu Ser Lys Leu Ile Asn Thr Leu Thr Asp Glu Asn Glu Lys Leu Arg
65                  70                  75                  80

Glu Glu Leu Gln Gln Tyr Tyr Ala Leu Ser Asp Ala Lys Glu Glu Glu
                85                  90                  95

Pro Arg Tyr Lys Ala Asp Asn Gln Ser Pro Ala Pro Val Lys Lys Glu
            100                 105                 110

Ala Lys Lys Leu Asn Glu Ala Glu Leu Tyr Asn Lys Ile Gln Glu Leu
        115                 120                 125

Glu Glu Gly Lys Ala Glu Leu Phe Asp Lys Leu Glu Lys Val Glu Glu
    130                 135                 140

Glu Asn Lys Lys Val Lys Glu Asp Ser Asp Asn Ile Asn Arg Ser Val
145                 150                 155                 160

Ser Val Lys Asp Asn Glu Lys Glu Leu His Asn Lys Ile Ala Asp Leu
                165                 170                 175

Glu Glu Glu Arg Gly Glu His Leu Asp Lys Ile Asp Glu Leu Lys Glu
            180                 185                 190

Glu Leu Lys Ala Lys Glu Lys Ser Ser Asp Ser Ser Arg Glu Val Thr
        195                 200                 205

Asn Glu Leu Thr Ala Ser Met Trp Lys Ala Gln Ala Asp Ser Ala Lys
    210                 215                 220

Ala Lys Ala Lys Glu Leu Glu Lys Gln Val Glu Glu Tyr Lys Lys Asn
225                 230                 235                 240

Tyr Glu Thr Leu Glu Lys Gly Tyr Asp Asp Leu Ala Glu Ser Arg Ser
                245                 250                 255

Val Ser Gln Gly Ser Val Ser Leu Glu Leu Tyr Asp Lys Leu Ser Asp
```

-continued

```
            260                 265                 270

Glu Asn Asp Ile Leu Arg Glu Lys Gln Asp Glu Tyr Leu Thr Lys Ile
        275                 280                 285

Asp Gly Leu Asp Lys Glu Asn Lys Glu Tyr Ala Ser Gln Glu Ser Gln
    290                 295                 300

Asn Ser Arg Ser Ile Thr Asn Glu Gln Leu Ile Asp Lys Leu Val Glu
305                 310                 315                 320

Glu Asn Asn Asp Leu Lys Glu Glu Arg Ala Lys Tyr Leu Asp Leu Leu
                325                 330                 335

Asp Asn Arg Glu Lys Asp Pro Gln Tyr Arg Ala Leu Met Gly Glu Ala
            340                 345                 350

Glu Lys Lys Val Glu Val Ala Asp Ser Asn Ala Ser Ser Val Ala Lys
        355                 360                 365

Leu Tyr Asn Gln Ile Ala Asp Leu Thr Asp Lys Asn Gly Glu Tyr Leu
    370                 375                 380

Glu Arg Ile Glu Glu Leu Glu Glu Arg Gln Lys Asn Leu Glu Lys Leu
385                 390                 395                 400

Glu Glu Gly Val Ser Val Gly Ser Asp Ala Ser Leu His Asn Arg Ile
                405                 410                 415

Thr Asp Leu Glu Glu Glu Arg Glu Lys Leu Leu Asn Lys Leu Asp Lys
            420                 425                 430

Val Glu Glu Glu His Lys Lys Asp His Glu Gln Leu Glu Lys Lys Ser
        435                 440                 445

Glu Asp Val
    450


<210> SEQ ID NO 8
<211> LENGTH: 401
<212> TYPE: PRT
<213> ORGANISM: Artificial Sequence
<220> FEATURE:
<223> OTHER INFORMATION: Fusion protein of group A streptococcus M
      proteins.

<400> SEQUENCE: 8

Met Asp Asn Pro Arg Tyr Thr Asp Ala His Asn Ala Val Thr Gln Gly
1               5                   10                  15

Arg Thr Val Pro Leu Gln Asn Leu Leu His Glu Met Asp Lys Asn Gly
            20                  25                  30

Lys Leu Arg Ser Glu Asn Glu Glu Leu Lys Ala Asp Leu Gln Lys Lys
        35                  40                  45

Glu Gln Glu Asp Ser Ser Ser Arg Asp Ile Thr Glu Ala Gly Val Ser
    50                  55                  60

Lys Phe Trp Lys Ser Lys Phe Asp Ala Glu Gln Asn Arg Ala Asn Glu
65                  70                  75                  80

Leu Glu Lys Lys Leu Ser Gly Tyr Glu Lys Asp Tyr Lys Thr Leu Glu
                85                  90                  95

Gln Glu Tyr Glu Asn Ala Gly Ser Glu Glu Asn Val Pro Lys Gln Gln
            100                 105                 110

Tyr Asn Ala Leu Trp Glu Glu Asn Glu Asp Leu Arg Gly Arg Glu Arg
        115                 120                 125

Lys Tyr Ile Ala Lys Leu Glu Lys Glu Glu Ile Gln Asn Gly Glu Leu
    130                 135                 140

Asn Glu Lys Asn Arg Lys Leu Glu Ser Pro Arg Glu Val Thr Asn Glu
145                 150                 155                 160

Leu Ala Ala Ser Val Trp Lys Lys Lys Val Glu Glu Ala Lys Glu Lys
```

165 170 175

Ala Ser Lys Leu Glu Lys Gln Leu Glu Glu Ala Gln Lys Asp Tyr Ser
180 185 190

Glu Ile Glu Gly Lys Leu Glu Gln Phe Val Glu Lys Lys Val Glu Ala
195 200 205

Ala Glu Asn Asn Val Ser Ser Val Ala Arg Arg Glu Lys Glu Leu Tyr
210 215 220

Asp Gln Ile Ala Asp Leu Thr Asp Lys Asn Gly Glu Tyr Leu Glu Arg
225 230 235 240

Ile Gly Glu Leu Glu Glu Arg Gln Lys Asn Leu Asp Asp Arg Ser Val
245 250 255

Ser Thr Asn Ser Gly Ser Val Ser Thr Pro Tyr Asn Asn Leu Leu Asn
260 265 270

Glu Tyr Asp Asp Leu Leu Ala Lys His Gly Glu Leu Leu Ser Glu Tyr
275 280 285

Asp Ala Leu Lys Glu Lys Gln Asp Lys Asn Gln Glu Glu Asn Ser Lys
290 295 300

Asn Pro Ala Pro Ala Pro Ala Ser Ala Val Pro Val Lys Lys Glu Ala
305 310 315 320

Thr Lys Leu Ser Glu Ala Glu Leu Tyr Asn Lys Ile Gln Glu Leu Glu
325 330 335

Glu Gly Lys Ala Glu Leu Phe Asp Lys Leu Glu Lys Val Glu Glu Asp
340 345 350

Asn Pro Arg Tyr Thr Asp Ala His Asn Ala Val Thr Gln Gly Arg Thr
355 360 365

Val Pro Leu Gln Asn Leu Leu His Glu Met Asp Lys Asn Gly Lys Leu
370 375 380

Arg Ser Glu Asn Glu Glu Leu Lys Ala Asp Leu Gln Lys Lys Glu Gln
385 390 395 400

Glu

<210> SEQ ID NO 9
<211> LENGTH: 457
<212> TYPE: PRT
<213> ORGANISM: Artificial Sequence
<220> FEATURE:
<223> OTHER INFORMATION: Fusion protein of group A streptococcus M proteins.

<400> SEQUENCE: 9

Met Asn Gly Asp Gly Asn Pro Arg Glu Val Ile Glu Asp Leu Ala Ala
1 5 10 15

Asn Asn Pro Ala Ile Gln Asn Ile Arg Leu Arg His Glu Asn Lys Asp
20 25 30

Leu Lys Ala Arg Leu Glu Asn Ala Met Glu Val Ala Gly Arg Asp Phe
35 40 45

Lys Arg Ala Leu Leu Asp Gln Val Thr Gln Leu Tyr Thr Lys His Asn
50 55 60

Ser Asn Tyr Gln Gln Tyr Asn Ala Gln Ala Gly Arg Leu Asp Leu Arg
65 70 75 80

Gln Lys Ala Glu Tyr Leu Lys Gly Leu Asn Asp Trp Ala Glu Arg Leu
85 90 95

Leu Gln Glu Leu Asn Arg Val Phe Pro Arg Gly Thr Val Glu Asn Pro
100 105 110

Asp Lys Ala Arg Glu Leu Leu Asn Lys Tyr Asp Val Glu Asn Arg Val
115 120 125

Phe Pro Arg Gly Thr Val Glu Asn Pro Asp Lys Ala Arg Glu Leu Leu
    130                 135                 140

Asn Lys Tyr Asp Val Glu Asn Ser Lys Asn Pro Val Pro Val Lys Lys
145                 150                 155                 160

Glu Ala Lys Leu Ser Glu Ala Glu Leu His Asp Lys Ile Lys Asn Leu
                165                 170                 175

Ser Lys Asn Pro Val Pro Val Lys Lys Glu Ala Lys Leu Ser Glu Ala
            180                 185                 190

Glu Leu His Asp Lys Ile Lys Asn Leu Ala Pro Leu Thr Arg Ala Thr
        195                 200                 205

Ala Asp Asn Lys Asp Glu Leu Ile Lys Arg Ala Asn Asp Tyr Glu Ile
    210                 215                 220

Gln Asn His Gln Leu Thr Val Glu Asn Lys Lys Leu Lys Thr Asp Lys
225                 230                 235                 240

Glu Gln Leu Thr Lys Glu Asn Asp Asp Leu Lys Ala Glu Ser Pro Lys
                245                 250                 255

Ser Thr Glu Thr Ser Ala Asn Gly Ala Asp Lys Leu Ala Asp Ala Tyr
            260                 265                 270

Asn Thr Leu Leu Thr Glu His Glu Lys Leu Arg Asp Glu Tyr Tyr Thr
        275                 280                 285

Leu Ile Asp Ala Lys Glu Glu Glu Pro Arg Tyr Lys Ala Asp His Ser
    290                 295                 300

Asp Leu Val Ala Glu Lys Gln Arg Leu Glu Asp Leu Gly Gln Lys Phe
305                 310                 315                 320

Glu Arg Leu Lys Gln Arg Ser Glu Leu Tyr Leu Gln Gln Tyr Tyr Asp
                325                 330                 335

Asn Lys Ser Asn Gly Tyr Lys Gly Asp Trp Tyr Val Gln Gln Leu Asp
            340                 345                 350

Ser Val Ser Gly Leu Glu Val Ala Asp Pro Ser Asp Ser Lys Lys Leu
        355                 360                 365

Ile Glu Leu Gly Leu Ala Lys Tyr Leu Asn Asp Lys Leu Pro Phe Lys
    370                 375                 380

Thr Lys Glu Asp Ser Glu Ile Leu Ser Glu Leu Arg Asp Val Leu Lys
385                 390                 395                 400

Asn Asn Gly Asp Gly Asn Pro Arg Glu Val Ile Glu Asp Leu Ala Ala
                405                 410                 415

Asn Asn Pro Ala Ile Gln Asn Ile Arg Leu Arg His Glu Asn Lys Asp
            420                 425                 430

Leu Lys Ala Arg Leu Glu Asn Ala Met Glu Val Ala Gly Arg Asp Phe
        435                 440                 445

Lys Arg Ala His His His His His His
    450                 455

<210> SEQ ID NO 10
<211> LENGTH: 457
<212> TYPE: PRT
<213> ORGANISM: Artificial Sequence
<220> FEATURE:
<223> OTHER INFORMATION: Fusion protein of group A streptococcus M
      proteins.

<400> SEQUENCE: 10

Met Ala Glu Ile Lys Lys Pro Gln Ala Asp Ser Ala Trp Asn Trp Pro
1               5                   10                  15

Lys Glu Tyr Asn Ala Leu Leu Lys Glu Asn Glu Glu Leu Lys Val Glu
            20                  25                  30

-continued

```
Arg Glu Lys Tyr Leu Ser Tyr Ala Asp Asp Lys Glu Lys Asp Pro Gln
        35                  40                  45

Tyr Arg Ala Ala Val Thr Arg Gly Thr Ile Asn Asp Pro Gln Arg Ala
    50                  55                  60

Lys Glu Ala Leu Asp Lys Tyr Glu Leu Glu Asn His Ala Val Thr Arg
65                  70                  75                  80

Gly Thr Ile Asn Asp Pro Gln Arg Ala Lys Glu Ala Leu Asp Lys Tyr
                85                  90                  95

Glu Leu Glu Asn His Thr Glu Val Lys Ala Ala Gly Gln Ser Ala Pro
            100                 105                 110

Lys Gly Thr Asn Val Ser Ala Asp Leu Tyr Asn Ser Leu Trp Asp Glu
        115                 120                 125

Asn Lys Thr Leu Arg Glu Lys Gln Glu Glu Tyr Ile Thr Lys Ile Gln
    130                 135                 140

Asn Glu Glu Thr Lys Asn Lys Glu Glu Glu Arg Thr Phe Thr Glu Leu
145                 150                 155                 160

Pro Tyr Glu Ala Arg Tyr Lys Ala Trp Lys Ser Glu Asn Asp Glu Leu
                165                 170                 175

Arg Glu Asn Tyr Arg Arg Thr Leu Asp Lys Phe Asn Thr Glu Gln Gly
            180                 185                 190

Lys Thr Thr Arg Leu Glu Glu Gln Asn Arg Val Arg Tyr Thr Arg His
        195                 200                 205

Thr Pro Glu Asp Lys Leu Lys Lys Ile Ile Asp Asp Leu Asp Ala Lys
    210                 215                 220

Glu His Arg Val Arg Tyr Thr Arg His Thr Pro Glu Asp Lys Leu Lys
225                 230                 235                 240

Lys Ile Ile Asp Asp Leu Asp Ala Lys Glu His Arg Val Tyr Ile Thr
                245                 250                 255

Arg Arg Met Thr Lys Glu Asp Val Glu Lys Ile Ala Asn Asp Leu Asp
            260                 265                 270

Thr Glu Asn His Gly Leu Lys Gln Gln Asn Glu Gln Leu Ser Thr Glu
        275                 280                 285

Lys Gln Gly Leu Glu Glu Gln Asn Lys Gln Leu Ser Thr Asp Arg Val
    290                 295                 300

Ser Arg Ser Met Ser Arg Asp Asp Leu Leu Asn Arg Ala Gln Asp Leu
305                 310                 315                 320

Glu Ala Lys Asn His Gly Leu Glu His Gln Asn Thr Lys Leu Ser Thr
                325                 330                 335

Glu Asn Lys Thr Leu Gln Glu Gln Ala Glu Ala Arg Gln Lys Glu Val
            340                 345                 350

Ala Thr Arg Ser Gln Thr Asp Thr Leu Glu Lys Val Gln Glu Arg Ala
        355                 360                 365

Asp Lys Phe Glu Ile Glu Asn Asn Thr Leu Lys Leu Lys Asn Ser Asp
    370                 375                 380

Leu Ser Phe Asn Asn Lys Ala Leu Lys Asp His Asn Asp Glu Leu Thr
385                 390                 395                 400

Glu Ala Glu Ile Lys Lys Pro Gln Ala Asp Ser Ala Trp Asn Trp Pro
                405                 410                 415

Lys Glu Tyr Asn Ala Leu Leu Lys Glu Asn Glu Glu Leu Lys Val Glu
            420                 425                 430

Arg Glu Lys Tyr Leu Ser Tyr Ala Asp Asp Lys Glu Lys Asp Pro Gln
        435                 440                 445

Tyr Arg Ala His His His His His His
```

450 455

<210> SEQ ID NO 11
<211> LENGTH: 457
<212> TYPE: PRT
<213> ORGANISM: Artificial Sequence
<220> FEATURE:
<223> OTHER INFORMATION: Fusion protein of group A streptococcus M proteins.

<400> SEQUENCE: 11

```
Met Glu Gly Val Ser Val Gly Ser Asp Ala Ser Leu His Asn Arg Ile
1               5                   10                  15

Thr Asp Leu Glu Glu Glu Arg Glu Lys Leu Leu Asn Lys Leu Asp Lys
            20                  25                  30

Val Glu Glu Glu His Lys Lys Asp His Glu Gln Leu Glu Lys Lys Ser
        35                  40                  45

Glu Asp Val Glu Ser Ser Asn Asn Ala Glu Ser Ser Asn Ile Ser Gln
    50                  55                  60

Glu Ser Lys Leu Ile Asn Thr Leu Thr Asp Glu Asn Glu Lys Leu Arg
65                  70                  75                  80

Glu Glu Leu Gln Gln Tyr Tyr Ala Leu Ser Asp Ala Lys Glu Glu Glu
                85                  90                  95

Pro Arg Tyr Lys Ala Asp Asn Gln Ser Pro Ala Pro Val Lys Lys Glu
            100                 105                 110

Ala Lys Lys Leu Asn Glu Ala Glu Leu Tyr Asn Lys Ile Gln Glu Leu
        115                 120                 125

Glu Glu Gly Lys Ala Glu Leu Phe Asp Lys Leu Glu Lys Val Glu Glu
    130                 135                 140

Glu Asn Lys Lys Val Lys Glu Asp Ser Asp Asn Ile Asn Arg Ser Val
145                 150                 155                 160

Ser Val Lys Asp Asn Glu Lys Glu Leu His Asn Lys Ile Ala Asp Leu
                165                 170                 175

Glu Glu Glu Arg Gly Glu His Leu Asp Lys Ile Asp Glu Leu Lys Glu
            180                 185                 190

Glu Leu Lys Ala Lys Glu Lys Ser Ser Asp Ser Ser Arg Glu Val Thr
        195                 200                 205

Asn Glu Leu Thr Ala Ser Met Trp Lys Ala Gln Ala Asp Ser Ala Lys
    210                 215                 220

Ala Lys Ala Lys Glu Leu Glu Lys Gln Val Glu Glu Tyr Lys Lys Asn
225                 230                 235                 240

Tyr Glu Thr Leu Glu Lys Gly Tyr Asp Asp Leu Ala Glu Ser Arg Ser
                245                 250                 255

Val Ser Gln Gly Ser Val Ser Leu Glu Leu Tyr Asp Lys Leu Ser Asp
            260                 265                 270

Glu Asn Asp Ile Leu Arg Glu Lys Gln Asp Glu Tyr Leu Thr Lys Ile
        275                 280                 285

Asp Gly Leu Asp Lys Glu Asn Lys Glu Tyr Ala Ser Gln Glu Ser Gln
    290                 295                 300

Asn Ser Arg Ser Ile Thr Asn Glu Gln Leu Ile Asp Lys Leu Val Glu
305                 310                 315                 320

Glu Asn Asn Asp Leu Lys Glu Glu Arg Ala Lys Tyr Leu Asp Leu Leu
                325                 330                 335

Asp Asn Arg Glu Lys Asp Pro Gln Tyr Arg Ala Leu Met Gly Glu Ala
            340                 345                 350

Glu Lys Lys Val Glu Val Ala Asp Ser Asn Ala Ser Ser Val Ala Lys
```

```
        355                 360                 365

Leu Tyr Asn Gln Ile Ala Asp Leu Thr Asp Lys Asn Gly Glu Tyr Leu
    370                 375                 380

Glu Arg Ile Glu Glu Leu Glu Glu Arg Gln Lys Asn Leu Glu Lys Leu
385                 390                 395                 400

Glu Glu Gly Val Ser Val Gly Ser Asp Ala Ser Leu His Asn Arg Ile
                405                 410                 415

Thr Asp Leu Glu Glu Glu Arg Glu Lys Leu Leu Asn Lys Leu Asp Lys
            420                 425                 430

Val Glu Glu Glu His Lys Lys Asp His Glu Gln Leu Glu Lys Lys Ser
        435                 440                 445

Glu Asp Val His His His His His His
    450                 455


<210> SEQ ID NO 12
<211> LENGTH: 407
<212> TYPE: PRT
<213> ORGANISM: Artificial Sequence
<220> FEATURE:
<223> OTHER INFORMATION: Fusion protein of group A streptococcus M
      proteins.

<400> SEQUENCE: 12

Met Asp Asn Pro Arg Tyr Thr Asp Ala His Asn Ala Val Thr Gln Gly
1               5                   10                  15

Arg Thr Val Pro Leu Gln Asn Leu Leu His Glu Met Asp Lys Asn Gly
            20                  25                  30

Lys Leu Arg Ser Glu Asn Glu Glu Leu Lys Ala Asp Leu Gln Lys Lys
        35                  40                  45

Glu Gln Glu Asp Ser Ser Ser Arg Asp Ile Thr Glu Ala Gly Val Ser
    50                  55                  60

Lys Phe Trp Lys Ser Lys Phe Asp Ala Glu Gln Asn Arg Ala Asn Glu
65                  70                  75                  80

Leu Glu Lys Lys Leu Ser Gly Tyr Glu Lys Asp Tyr Lys Thr Leu Glu
                85                  90                  95

Gln Glu Tyr Glu Asn Ala Gly Ser Glu Glu Asn Val Pro Lys Gln Gln
            100                 105                 110

Tyr Asn Ala Leu Trp Glu Glu Asn Glu Asp Leu Arg Gly Arg Glu Arg
        115                 120                 125

Lys Tyr Ile Ala Lys Leu Glu Lys Glu Glu Ile Gln Asn Gly Glu Leu
    130                 135                 140

Asn Glu Lys Asn Arg Lys Leu Glu Ser Pro Arg Glu Val Thr Asn Glu
145                 150                 155                 160

Leu Ala Ala Ser Val Trp Lys Lys Lys Val Glu Glu Ala Lys Glu Lys
                165                 170                 175

Ala Ser Lys Leu Glu Lys Gln Leu Glu Glu Ala Gln Lys Asp Tyr Ser
            180                 185                 190

Glu Ile Glu Gly Lys Leu Glu Gln Phe Val Glu Lys Lys Val Glu Ala
        195                 200                 205

Ala Glu Asn Asn Val Ser Ser Val Ala Arg Arg Glu Lys Glu Leu Tyr
    210                 215                 220

Asp Gln Ile Ala Asp Leu Thr Asp Lys Asn Gly Glu Tyr Leu Glu Arg
225                 230                 235                 240

Ile Gly Glu Leu Glu Glu Arg Gln Lys Asn Leu Asp Asp Arg Ser Val
                245                 250                 255

Ser Thr Asn Ser Gly Ser Val Ser Thr Pro Tyr Asn Asn Leu Leu Asn
```

```
            260                 265                 270

Glu Tyr Asp Asp Leu Leu Ala Lys His Gly Glu Leu Leu Ser Glu Tyr
        275                 280                 285

Asp Ala Leu Lys Glu Lys Gln Asp Lys Asn Gln Glu Glu Asn Ser Lys
    290                 295                 300

Asn Pro Ala Pro Ala Pro Ala Ser Ala Val Pro Val Lys Lys Glu Ala
305                 310                 315                 320

Thr Lys Leu Ser Glu Ala Glu Leu Tyr Asn Lys Ile Gln Glu Leu Glu
                325                 330                 335

Glu Gly Lys Ala Glu Leu Phe Asp Lys Leu Glu Lys Val Glu Glu Asp
            340                 345                 350

Asn Pro Arg Tyr Thr Asp Ala His Asn Ala Val Thr Gln Gly Arg Thr
        355                 360                 365

Val Pro Leu Gln Asn Leu Leu His Glu Met Asp Lys Asn Gly Lys Leu
    370                 375                 380

Arg Ser Glu Asn Glu Glu Leu Lys Ala Asp Leu Gln Lys Lys Glu Gln
385                 390                 395                 400

Glu His His His His His His
                405

<210> SEQ ID NO 13
<211> LENGTH: 1463
<212> TYPE: DNA
<213> ORGANISM: Artificial Sequence
<220> FEATURE:
<223> OTHER INFORMATION: Polynucleotide encoding a fusion protein of
      group A streptococcus M proteins.

<400> SEQUENCE: 13
agatctcgat cccgcgaaat taatacgact cactataggg gaattgtgag cggataacaa      60
ttcccctcta gaaataattt tgtttaactt taagaaggag atatcatatg aacggtgacg     120
gtaacccgcg tgaagttatc gaagacctgg ctgctaacaa cccggctatc cagaacatcc     180
gtctgcgtca cgaaaacaaa gacctgaaag ctcgtctgga aaacgctatg gaagttgctg     240
gtcgtgactt caaacgtgct ctgctggacc aggttaccca gctgtacacc aaacacaact     300
ccaactacca gcagtacaac gctcaggctg gtcgtctgga cctgcgtcag aaagctgaat     360
acctgaaagg tctgaacgac tgggctgaac gtctgctgca ggaactgaac cgtgttttcc     420
cgcgtggtac cgttgaaaac ccggacaaag ctcgtgaact gctgaacaaa tacgacgttg     480
aaaaccgtgt tttcccgcgt ggtaccgttg aaaacccgga caaagctcgt gaactgctga     540
acaaatacga cgttgaaaac tccaaaaacc cggttccggt taaaaaagaa gctaaactgt     600
ccgaagctga actgcacgac aaaatcaaaa acctgtccaa aaacccggtt ccggttaaaa     660
aagaagctaa actgtccgaa gctgaactgc acgacaaaat caaaaacctg gctccgctga     720
cccgtgctac cgctgacaac aaagacgaac tgatcaaacg tgctaacgac tacgaaatcc     780
agaaccacca gctgaccgtt gaaaacaaaa aactgaaaac cgacaaagaa cagctgacca     840
aagaaaacga cgacctgaaa gctgaatccc cgaaatccac cgaaacctcc gctaacggtg     900
ctgacaaact ggctgacgct tacaacaccc tgctgaccga acacgaaaaa ctgcgtgacg     960
aatactacac cctgatcgac gctaaagaag aagaaccgcg ttacaaagct gaccactccg    1020
acctggttgc tgaaaaacag cgtctggaag acctgggtca gaaattcgaa cgtctgaaac    1080
agcgttccga actgtacctg cagcagtact acgacaacaa atccaacggt tacaaaggtg    1140
actggtacgt tcagcagctg gactccgttt ccggtctgga agttgctgac ccgtccgact    1200
```

```
ccaaaaaact gatcgaactg ggtctggcta aatacctgaa cgacaaactg ccgttcaaaa   1260

ccaaagaaga ctccgaaatc ctgtccgaac tgcgtgacgt tctgaaaaac aacggtgacg   1320

gtaacccgcg tgaagttatc gaagacctgg ctgctaacaa cccggctatc cagaacatcc   1380

gtctgcgtca cgaaaacaaa gacctgaaag ctcgtctgga aaacgctatg gaagttgctg   1440

gtcgtgactt caaacgtgct tag                                           1463
```

<210> SEQ ID NO 14
<211> LENGTH: 1463
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 14

```
agatctcgat cccgcgaaat taatacgact cactataggg gaattgtgag cggataacaa     60

ttcccctcta gaaataattt tgtttaactt taagaaggag atataccatg gctgaaatca    120

aaaaaccgca ggctgactcc gcttggaact ggccgaaaga atacaacgct ctgctgaaag    180

aaaacgaaga actgaaagtt gaacgtgaaa aatacctgtc ctacgctgac gacaaagaaa    240

aagacccgca gtaccgtgct gctgttaccc gtggtaccat caacgacccg cagcgtgcta    300

aagaagctct ggacaaatac gaactggaaa accacgctgt tacccgtggt accatcaacg    360

acccgcagcg tgctaaagaa gctctggaca aatacgaact ggaaaaccac accgaagtta    420

aagctgctgg tcagtccgct ccgaaaggta ccaacgtttc cgctgacctg tacaactccc    480

tgtgggacga aaacaaaacc ctgcgtgaaa aacaggaaga atacatcacc aaaatccaga    540

acgaagaaac caaaaacaaa gaagaagaac gtaccttcac cgaactgccg tacgaagctc    600

gttacaaagc ttggaaatcc gaaaacgacg aactgcgtga aaactaccgt cgtaccctgg    660

acaaattcaa caccgaacag ggtaaaacca cccgtctgga agaacagaac cgtgttcgtt    720

acacccgtca caccccggaa gacaaactga aaaaaatcat cgacgacctg gacgctaaag    780

aacaccgtgt tcgttacacc cgtcacaccc cggaagacaa actgaaaaaa atcatcgacg    840

acctggacgc taaagaacac cgtgtttaca tcacccgtcg tatgaccaaa gaagacgttg    900

aaaaaatcgc taacgacctg gacaccgaaa accacggtct gaaacagcag aacgaacagc    960

tgtccaccga aaaacagggt ctggaagaac agaacaaaca gctgtccacc gaccgtgttt   1020

cccgttccat gtcccgtgac gacctgctga accgtgctca ggacctggaa gctaaaaacc   1080

acggtctgga acaccagaac accaaactgt ccaccgaaaa caaaaccctg caggaacagg   1140

ctgaagctcg tcagaaagaa gttgctaccc gttcccagac cgacaccctg gaaaaagttc   1200

aggaacgtgc tgacaaattc gaaatcgaaa acaacaccct gaaactgaaa aactccgacc   1260

tgtccttcaa caacaaagct ctgaaagacc acaacgacga actgaccgaa gctgaaatca   1320

aaaaaccgca ggctgactcc gcttggaact ggccgaaaga atacaacgct ctgctgaaag   1380

aaaacgaaga actgaaagtt gaacgtgaaa aatacctgtc ctacgctgac gacaaagaaa   1440

aagacccgca gtaccgtgct tag                                           1463
```

<210> SEQ ID NO 15
<211> LENGTH: 1463
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 15

```
agatctcgat cccgcgaaat taatacgact cactataggg gaattgtgag cggataacaa     60
ttcccctcta gaaataattt tgtttaactt taagaaggag atataccatg gaaggtgttt    120
ccgttggttc cgacgcttcc ctgcacaacc gtatcaccga cctggaagaa gaacgtgaaa    180
aactgctgaa caaactggac aaagttgaag aagaacacaa aaaagaccac gaacagctgg    240
aaaaaaaatc cgaagacgtt gaatcctcca acaacgctga atcctccaac atctcccagg    300
aatccaaact gatcaacacc ctgaccgacg aaaacgaaaa actgcgtgaa gaactgcagc    360
agtactacgc tctgtccgac gctaaagaag aagaaccgcg ttacaaagct gacaaccagt    420
ccccggctcc ggttaaaaaa gaagctaaaa aactgaacga agctgaactg tacaacaaaa    480
tccaggaact ggaagaaggt aaagctgaac tgttcgacaa actggaaaaa gttgaagaag    540
aaaacaaaaa agttaaagaa gactccgaca acatcaaccg ttccgtttcc gttaaagaca    600
acgaaaaaga actgcacaac aaaatcgctg acctggaaga agaacgtggt gaacacctgg    660
acaaaatcga cgaactgaaa gaagaactga aagctaaaga aaaatcctcc gactcctccc    720
gtgaagttac caacgaactg accgcttcca tgtggaaagc tcaggctgac tccgctaaag    780
ctaaagctaa agaactggaa aaacaggttg aagaatacaa aaaaaactac gaaaccctgg    840
aaaaaggtta cgacgacctg gctgaatccc gttccgtttc ccagggttcc gtttccctgg    900
aactgtacga caaactgtcc gacgaaaacg acatcctgcg tgaaaaacag gacgaatacc    960
tgaccaaaat cgacggtctg gacaaagaaa acaaagaata cgcttcccag gaatcccaga   1020
actcccgttc catcaccaac gaacagctga tcgacaaact ggttgaagaa aacaacgacc   1080
tgaaagaaga acgtgctaaa tacctggacc tgctggacaa ccgtgaaaaa gacccgcagt   1140
accgtgctct gatgggtgaa gctgaaaaaa aagttgaagt tgctgactcc aacgcttcct   1200
ccgttgctaa actgtacaac cagatcgctg acctgaccga caaaaacggt gaatacctgg   1260
aacgtatcga agaactggaa gaacgtcaga aaaacctgga aaaactggaa gaaggtgttt   1320
ccgttggttc cgacgcttcc ctgcacaacc gtatcaccga cctggaagaa gaacgtgaaa   1380
aactgctgaa caaactggac aaagttgaag aagaacacaa aaaagaccac gaacagctgg   1440
aaaaaaaatc cgaagacgtt tag                                           1463
```

<210> SEQ ID NO 16
<211> LENGTH: 1313
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 16

```
agatctcgat cccgcgaaat taatacgact cactataggg gaattgtgag cggataacaa     60
ttcccctcta gaaataattt tgtttaactt taagaaggag atataccatg gacaacccgc    120
gttacaccga cgctcacaac gctgttaccc agggtcgtac cgttccgctg cagaacctgc    180
tgcacgaaat ggacaaaaac ggtaaactgc gttccgaaaa cgaagaactg aaagctgacc    240
tgcagaaaaa agaacaggaa gactcctcct cccgtgacat caccgaagct ggtgtttcca    300
aattctggaa atccaaattc gacgctgaac agaaccgtgc taacgaactg gaaaaaaaac    360
tgtccggtta cgaaaaagac tacaaaaccc tggaacagga atacgaaaac gctggttccg    420
aagaaaacgt tccgaaacag cagtacaacg ctctgtggga agaaaacgaa gacctgcgtg    480
gtcgtgaacg taaatacatc gctaaactgg aaaaagaaga aatccagaac ggtgaactga    540
```

-continued acgaaaaaaa ccgtaaactg gaatccccgc gtgaagttac caacgaactg gctgcttccg 600
tttggaaaaa aaaagttgaa gaagctaaag aaaaagcttc caaactggaa aaacagctgg 660
aagaagctca gaaagactac tccgaaatcg aaggtaaact ggaacagttc gttgaaaaaa 720
aagttgaagc tgctgaaaac aacgtttcct ccgttgctcg tcgtgaaaaa gaactgtacg 780
accagatcgc tgacctgacc gacaaaaacg gtgaatacct ggaacgtatc ggtgaactgg 840
aagaacgtca gaaaaacctg gacgaccgtt ccgtttccac caactccggt tccgtttcca 900
ccccgtacaa caacctgctg aacgaatacg acgacctgct ggctaaacac ggtgaactgc 960
tgtccgaata cgacgctctg aaagaaaaac aggacaaaaa ccaggaagaa aactccaaaa 1020
acccggctcc ggctccggct tccgctgttc cggttaaaaa agaagctacc aaactgtccg 1080
aagctgaact gtacaacaaa atccaggaac tggaagaagg taaagctgaa ctgttcgaca 1140
aactggaaaa agttgaagaa gacaacccgc gttacaccga cgctcacaac gctgttaccc 1200
agggtcgtac cgttccgctg cagaacctgc tgcacgaaat ggacaaaaac ggtaaactgc 1260
gttccgaaaa cgaagaactg aaagctgacc tgcagaaaaa agaacaggaa tag 1313

<210> SEQ ID NO 17
<211> LENGTH: 1481
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 17
agatctcgat cccgcgaaat taatacgact cactataggg gaattgtgag cggataacaa 60
ttcccctcta gaaataattt tgtttaactt taagaaggag atatcatatg aacggtgacg 120
gtaacccgcg tgaagttatc gaagacctgg ctgctaacaa cccggctatc cagaacatcc 180
gtctgcgtca cgaaaacaaa gacctgaaag ctcgtctgga aaacgctatg gaagttgctg 240
gtcgtgactt caaacgtgct ctgctggacc aggttaccca gctgtacacc aaacacaact 300
ccaactacca gcagtacaac gctcaggctg gtcgtctgga cctgcgtcag aaagctgaat 360
acctgaaagg tctgaacgac tgggctgaac gtctgctgca ggaactgaac cgtgttttcc 420
cgcgtggtac cgttgaaaac ccggacaaag ctcgtgaact gctgaacaaa tacgacgttg 480
aaaaccgtgt tttcccgcgt ggtaccgttg aaaacccgga caaagctcgt gaactgctga 540
acaaatacga cgttgaaaac tccaaaaacc cggttccggt taaaaaagaa gctaaactgt 600
ccgaagctga actgcacgac aaaatcaaaa acctgtccaa aaacccggtt ccggttaaaa 660
aagaagctaa actgtccgaa gctgaactgc acgacaaaat caaaaacctg gctccgctga 720
cccgtgctac cgctgacaac aaagacgaac tgatcaaacg tgctaacgac tacgaaatcc 780
agaaccacca gctgaccgtt gaaaacaaaa aactgaaaac cgacaaagaa cagctgacca 840
aagaaaacga cgacctgaaa gctgaatccc cgaaatccac cgaaacctcc gctaacggtg 900
ctgacaaact ggctgacgct tacaacaccc tgctgaccga acacgaaaaa ctgcgtgacg 960
aatactacac cctgatcgac gctaaagaag aagaaccgcg ttacaaagct gaccactccg 1020
acctggttgc tgaaaaacag cgtctggaag acctgggtca gaaattcgaa cgtctgaaac 1080
agcgttccga actgtacctg cagcagtact acgacaacaa atccaacggt tacaaaggtg 1140
actggtacgt tcagcagctg gactccgttt ccggtctgga agttgctgac ccgtccgact 1200
ccaaaaaact gatcgaactg ggtctggcta aatacctgaa cgacaaactg ccgttcaaaa 1260

-continued

```
ccaaagaaga ctccgaaatc ctgtccgaac tgcgtgacgt tctgaaaaac aacggtgacg   1320

gtaacccgcg tgaagttatc gaagacctgg ctgctaacaa cccggctatc cagaacatcc   1380

gtctgcgtca cgaaaacaaa gacctgaaag ctcgtctgga aaacgctatg gaagttgctg   1440

gtcgtgactt caaacgtgct caccaccacc accaccacta g                       1481
```

<210> SEQ ID NO 18
<211> LENGTH: 1481
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 18

```
agatctcgat cccgcgaaat taatacgact cactataggg gaattgtgag cggataacaa     60

ttcccctcta gaaataattt tgtttaactt taagaaggag atataccatg gctgaaatca    120

aaaaaccgca ggctgactcc gcttggaact ggccgaaaga atacaacgct ctgctgaaag    180

aaaacgaaga actgaaagtt gaacgtgaaa aatacctgtc ctacgctgac gacaaagaaa    240

aagacccgca gtaccgtgct gctgttaccc gtggtaccat caacgacccg cagcgtgcta    300

aagaagctct ggacaaatac gaactggaaa accacgctgt tacccgtggt accatcaacg    360

acccgcagcg tgctaaagaa gctctggaca aatacgaact ggaaaaccac accgaagtta    420

aagctgctgg tcagtccgct ccgaaaggta ccaacgtttc cgctgacctg tacaactccc    480

tgtgggacga aaacaaaacc ctgcgtgaaa aacaggaaga atacatcacc aaaatccaga    540

acgaagaaac caaaaacaaa gaagaagaac gtaccttcac cgaactgccg tacgaagctc    600

gttacaaagc ttggaaatcc gaaaacgacg aactgcgtga aaactaccgt cgtaccctgg    660

acaaattcaa caccgaacag ggtaaaacca cccgtctgga agaacagaac cgtgttcgtt    720

acacccgtca caccccggaa gacaaactga aaaaaatcat cgacgacctg gacgctaaag    780

aacaccgtgt tcgttacacc cgtcacaccc cggaagacaa actgaaaaaa atcatcgacg    840

acctggacgc taaagaacac cgtgtttaca tcacccgtcg tatgaccaaa gaagacgttg    900

aaaaaatcgc taacgacctg gacaccgaaa accacggtct gaaacagcag aacgaacagc    960

tgtccaccga aaaacagggt ctggaagaac agaacaaaca gctgtccacc gaccgtgttt   1020

cccgttccat gtcccgtgac gacctgctga accgtgctca ggacctggaa gctaaaaacc   1080

acggtctgga acaccagaac accaaactgt ccaccgaaaa caaaaccctg caggaacagg   1140

ctgaagctcg tcagaaagaa gttgctaccc gttcccagac cgacaccctg gaaaaagttc   1200

aggaacgtgc tgacaaattc gaaatcgaaa acaacaccct gaaactgaaa aactccgacc   1260

tgtccttcaa caacaaagct ctgaaagacc acaacgacga actgaccgaa gctgaaatca   1320

aaaaaccgca ggctgactcc gcttggaact ggccgaaaga atacaacgct ctgctgaaag   1380

aaaacgaaga actgaaagtt gaacgtgaaa aatacctgtc ctacgctgac gacaaagaaa   1440

aagacccgca gtaccgtgct caccaccacc accaccacta g                       1481
```

<210> SEQ ID NO 19
<211> LENGTH: 1481
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 19

-continued agatctcgat cccgcgaaat taatacgact cactataggg gaattgtgag cggataacaa 60
ttcccctcta gaaataattt tgtttaactt taagaaggag atataccatg gaaggtgttt 120
ccgttggttc cgacgcttcc ctgcacaacc gtatcaccga cctggaagaa gaacgtgaaa 180
aactgctgaa caaactggac aaagttgaag aagaacacaa aaaagaccac gaacagctgg 240
aaaaaaaatc cgaagacgtt gaatcctcca acaacgctga atcctccaac atctcccagg 300
aatccaaact gatcaacacc ctgaccgacg aaaacgaaaa actgcgtgaa gaactgcagc 360
agtactacgc tctgtccgac gctaaagaag aagaaccgcg ttacaaagct gacaaccagt 420
ccccggctcc ggttaaaaaa gaagctaaaa aactgaacga agctgaactg tacaacaaaa 480
tccaggaact ggaagaaggt aaagctgaac tgttcgacaa actggaaaaa gttgaagaag 540
aaaacaaaaa agttaaagaa gactccgaca acatcaaccg ttccgtttcc gttaaagaca 600
acgaaaaaga actgcacaac aaaatcgctg acctggaaga agaacgtggt gaacacctgg 660
acaaaatcga cgaactgaaa gaagaactga aagctaaaga aaaatcctcc gactcctccc 720
gtgaagttac caacgaactg accgcttcca tgtggaaagc tcaggctgac tccgctaaag 780
ctaaagctaa agaactggaa aaacaggttg aagaatacaa aaaaaactac gaaaccctgg 840
aaaaaggtta cgacgacctg gctgaatccc gttccgtttc ccagggttcc gtttccctgg 900
aactgtacga caaactgtcc gacgaaaacg acatcctgcg tgaaaaacag gacgaatacc 960
tgaccaaaat cgacggtctg gacaaagaaa acaaagaata cgcttcccag gaatcccaga 1020
actcccgttc catcaccaac gaacagctga tcgacaaact ggttgaagaa aacaacgacc 1080
tgaaagaaga acgtgctaaa tacctggacc tgctggacaa ccgtgaaaaa gacccgcagt 1140
accgtgctct gatgggtgaa gctgaaaaaa aagttgaagt tgctgactcc aacgcttcct 1200
ccgttgctaa actgtacaac cagatcgctg acctgaccga caaaaacggt gaatacctgg 1260
aacgtatcga agaactggaa gaacgtcaga aaaacctgga aaaactggaa gaaggtgttt 1320
ccgttggttc cgacgcttcc ctgcacaacc gtatcaccga cctggaagaa gaacgtgaaa 1380
aactgctgaa caaactggac aaagttgaag aagaacacaa aaaagaccac gaacagctgg 1440
aaaaaaaatc cgaagacgtt caccaccacc accaccacta g 1481

<210> SEQ ID NO 20
<211> LENGTH: 1331
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 20
agatctcgat cccgcgaaat taatacgact cactataggg gaattgtgag cggataacaa 60
ttcccctcta gaaataattt tgtttaactt taagaaggag atataccatg gacaacccgc 120
gttacaccga cgctcacaac gctgttaccc agggtcgtac cgttccgctg cagaacctgc 180
tgcacgaaat ggacaaaaac ggtaaactgc gttccgaaaa cgaagaactg aaagctgacc 240
tgcagaaaaa agaacaggaa gactcctcct cccgtgacat caccgaagct ggtgtttcca 300
aattctggaa atccaaattc gacgctgaac agaaccgtgc taacgaactg gaaaaaaaac 360
tgtccggtta cgaaaaagac tacaaaaccc tggaacagga atacgaaaac gctggttccg 420
aagaaaacgt tccgaaacag cagtacaacg ctctgtggga agaaaacgaa gacctgcgtg 480
gtcgtgaacg taaatacatc gctaaactgg aaaaagaaga aatccagaac ggtgaactga 540
acgaaaaaaa ccgtaaactg gaatccccgc gtgaagttac caacgaactg gctgcttccg 600

```
tttggaaaaa aaaagttgaa gaagctaaag aaaaagcttc caaactggaa aaacagctgg    660

aagaagctca gaaagactac tccgaaatcg aaggtaaact ggaacagttc gttgaaaaaa    720

aagttgaagc tgctgaaaac aacgtttcct ccgttgctcg tcgtgaaaaa gaactgtacg    780

accagatcgc tgacctgacc gacaaaaacg gtgaatacct ggaacgtatc ggtgaactgg    840

aagaacgtca gaaaaacctg gacgaccgtt ccgtttccac caactccggt tccgtttcca    900

ccccgtacaa caacctgctg aacgaatacg acgacctgct ggctaaacac ggtgaactgc    960

tgtccgaata cgacgctctg aaagaaaaac aggacaaaaa ccaggaagaa aactccaaaa   1020

acccggctcc ggctccggct tccgctgttc cggttaaaaa agaagctacc aaactgtccg   1080

aagctgaact gtacaacaaa atccaggaac tggaagaagg taaagctgaa ctgttcgaca   1140

aactggaaaa agttgaagaa gacaacccgc gttacaccga cgctcacaac gctgttaccc   1200

agggtcgtac cgttccgctg cagaacctgc tgcacgaaat ggacaaaaac ggtaaactgc   1260

gttccgaaaa cgaagaactg aaagctgacc tgcagaaaaa agaacaggaa caccaccacc   1320

accaccacta g                                                        1331
```

<210> SEQ ID NO 21
<211> LENGTH: 1356
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 21

```
atgaacggtg acggtaaccc gcgtgaagtt atcgaagacc tggctgctaa caacccggct     60

atccagaaca tccgtctgcg tcacgaaaac aaagacctga aagctcgtct ggaaaacgct    120

atggaagttg ctggtcgtga cttcaaacgt gctctgctgg accaggttac ccagctgtac    180

accaaacaca actccaacta ccagcagtac aacgctcagg ctggtcgtct ggacctgcgt    240

cagaaagctg aatacctgaa aggtctgaac gactgggctg aacgtctgct gcaggaactg    300

aaccgtgttt tcccgcgtgg taccgttgaa aacccggaca aagctcgtga actgctgaac    360

aaatacgacg ttgaaaaccg tgttttcccg cgtggtaccg ttgaaaaccc ggacaaagct    420

cgtgaactgc tgaacaaata cgacgttgaa aactccaaaa acccggttcc ggttaaaaaa    480

gaagctaaac tgtccgaagc tgaactgcac gacaaaatca aaaacctgtc caaaaacccg    540

gttccggtta aaaaagaagc taaactgtcc gaagctgaac tgcacgacaa aatcaaaaac    600

ctggctccgc tgacccgtgc taccgctgac aacaaagacg aactgatcaa acgtgctaac    660

gactacgaaa tccagaacca ccagctgacc gttgaaaaca aaaaactgaa aaccgacaaa    720

gaacagctga ccaaagaaaa cgacgacctg aaagctgaat ccccgaaatc caccgaaacc    780

tccgctaacg gtgctgacaa actggctgac gcttacaaca ccctgctgac cgaacacgaa    840

aaactgcgtg acgaatacta caccctgatc gacgctaaag aagaagaacc gcgttacaaa    900

gctgaccact ccgacctggt tgctgaaaaa cagcgtctgg aagacctggg tcagaaattc    960

gaacgtctga aacagcgttc cgaactgtac ctgcagcagt actacgacaa caaatccaac   1020

ggttacaaag gtgactggta cgttcagcag ctggactccg tttccggtct ggaagttgct   1080

gacccgtccg actccaaaaa actgatcgaa ctgggtctgg ctaaatacct gaacgacaaa   1140

ctgccgttca aaaccaaaga agactccgaa atcctgtccg aactgcgtga cgttctgaaa   1200

aacaacggtg acggtaaccc gcgtgaagtt atcgaagacc tggctgctaa caacccggct   1260
```

atccagaaca tccgtctgcg tcacgaaaac aaagacctga aagctcgtct ggaaaacgct 1320
atggaagttg ctggtcgtga cttcaaacgt gcttag 1356

<210> SEQ ID NO 22
<211> LENGTH: 1356
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 22
atggctgaaa tcaaaaaacc gcaggctgac tccgcttgga actggccgaa agaatacaac 60
gctctgctga aagaaaacga agaactgaaa gttgaacgtg aaaaatacct gtcctacgct 120
gacgacaaag aaaaagaccc gcagtaccgt gctgctgtta cccgtggtac catcaacgac 180
ccgcagcgtg ctaaagaagc tctggacaaa tacgaactgg aaaaccacgc tgttacccgt 240
ggtaccatca acgacccgca gcgtgctaaa gaagctctgg acaaatacga actggaaaac 300
cacaccgaag ttaaagctgc tggtcagtcc gctccgaaag gtaccaacgt ttccgctgac 360
ctgtacaact ccctgtggga cgaaaacaaa accctgcgtg aaaaacagga agaatacatc 420
accaaaatcc agaacgaaga aaccaaaaac aaagaagaag aacgtacctt caccgaactg 480
ccgtacgaag ctcgttacaa agcttggaaa tccgaaaacg acgaactgcg tgaaaactac 540
cgtcgtaccc tggacaaatt caacaccgaa cagggtaaaa ccacccgtct ggaagaacag 600
aaccgtgttc gttacacccg tcacaccccg gaagacaaac tgaaaaaaat catcgacgac 660
ctggacgcta aagaacaccg tgttcgttac acccgtcaca ccccggaaga caaactgaaa 720
aaaatcatcg acgacctgga cgctaaagaa caccgtgttt acatcacccg tcgtatgacc 780
aaagaagacg ttgaaaaaat cgctaacgac ctggacaccg aaaaccacgg tctgaaacag 840
cagaacgaac agctgtccac cgaaaaacag ggtctggaag aacagaacaa acagctgtcc 900
accgaccgtg tttcccgttc catgtcccgt gacgacctgc tgaaccgtgc tcaggacctg 960
gaagctaaaa accacggtct ggaacaccag aacaccaaac tgtccaccga aaacaaaacc 1020
ctgcaggaac aggctgaagc tcgtcagaaa gaagttgcta cccgttccca gaccgacacc 1080
ctggaaaaag ttcaggaacg tgctgacaaa ttcgaaatcg aaaacaacac cctgaaactg 1140
aaaaactccg acctgtcctt caacaacaaa gctctgaaag accacaacga cgaactgacc 1200
gaagctgaaa tcaaaaaacc gcaggctgac tccgcttgga actggccgaa agaatacaac 1260
gctctgctga aagaaaacga agaactgaaa gttgaacgtg aaaaatacct gtcctacgct 1320
gacgacaaag aaaaagaccc gcagtaccgt gcttag 1356

<210> SEQ ID NO 23
<211> LENGTH: 1356
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 23
atggaaggtg tttccgttgg ttccgacgct tccctgcaca accgtatcac cgacctggaa 60
gaagaacgtg aaaaactgct gaacaaactg gacaaagttg aagaagaaca caaaaaagac 120
cacgaacagc tggaaaaaaa atccgaagac gttgaatcct ccaacaacgc tgaatcctcc 180
aacatctccc aggaatccaa actgatcaac accctgaccg acgaaaacga aaaactgcgt 240

-continued

```
gaagaactgc agcagtacta cgctctgtcc gacgctaaag aagaagaacc gcgttacaaa    300

gctgacaacc agtccccggc tccggttaaa aaagaagcta aaaaactgaa cgaagctgaa    360

ctgtacaaca aaatccagga actggaagaa ggtaaagctg aactgttcga caaactggaa    420

aaagttgaag aagaaaacaa aaaagttaaa gaagactccg acaacatcaa ccgttccgtt    480

tccgttaaag acaacgaaaa agaactgcac aacaaaatcg ctgacctgga agaagaacgt    540

ggtgaacacc tggacaaaat cgacgaactg aaagaagaac tgaaagctaa agaaaaatcc    600

tccgactcct cccgtgaagt taccaacgaa ctgaccgctt ccatgtggaa agctcaggct    660

gactccgcta aagctaaagc taaagaactg gaaaaacagg ttgaagaata caaaaaaaac    720

tacgaaaccc tggaaaaagg ttacgacgac ctggctgaat cccgttccgt ttcccagggt    780

tccgtttccc tggaactgta cgacaaactg tccgacgaaa acgacatcct gcgtgaaaaa    840

caggacgaat acctgaccaa aatcgacggt ctggacaaag aaaacaaaga atacgcttcc    900

caggaatccc agaactcccg ttccatcacc aacgaacagc tgatcgacaa actggttgaa    960

gaaaacaacg acctgaaaga agaacgtgct aaatacctgg acctgctgga caaccgtgaa   1020

aaagacccgc agtaccgtgc tctgatgggt gaagctgaaa aaaaagttga agttgctgac   1080

tccaacgctt cctccgttgc taaactgtac aaccagatcg ctgacctgac cgacaaaaac   1140

ggtgaatacc tggaacgtat cgaagaactg gaagaacgtc agaaaaacct ggaaaaactg   1200

gaagaaggtg tttccgttgg ttccgacgct tccctgcaca accgtatcac cgacctggaa   1260

gaagaacgtg aaaaactgct gaacaaactg gacaaagttg aagaagaaca caaaaaagac   1320

cacgaacagc tggaaaaaaa atccgaagac gtttag                             1356
```

<210> SEQ ID NO 24
<211> LENGTH: 1206
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 24

```
atggacaacc cgcgttacac cgacgctcac aacgctgtta cccagggtcg taccgttccg     60

ctgcagaacc tgctgcacga aatggacaaa aacggtaaac tgcgttccga aaacgaagaa    120

ctgaaagctg acctgcagaa aaaagaacag gaagactcct cctcccgtga catcaccgaa    180

gctggtgttt ccaaattctg gaaatccaaa ttcgacgctg aacagaaccg tgctaacgaa    240

ctggaaaaaa aactgtccgg ttacgaaaaa gactacaaaa ccctggaaca ggaatacgaa    300

aacgctggtt ccgaagaaaa cgttccgaaa cagcagtaca acgctctgtg ggaagaaaac    360

gaagacctgc gtggtcgtga acgtaaatac atcgctaaac tggaaaaaga agaaatccag    420

aacggtgaac tgaacgaaaa aaaccgtaaa ctggaatccc cgcgtgaagt taccaacgaa    480

ctggctgctt ccgtttggaa aaaaaaagtt gaagaagcta aagaaaaagc ttccaaactg    540

gaaaaacagc tggaagaagc tcagaaagac tactccgaaa tcgaaggtaa actggaacag    600

ttcgttgaaa aaaaagttga agctgctgaa aacaacgttt cctccgttgc tcgtcgtgaa    660

aaagaactgt acgaccagat cgctgacctg accgacaaaa acggtgaata cctggaacgt    720

atcggtgaac tggaagaacg tcagaaaaac ctggacgacc gttccgtttc caccaactcc    780

ggttccgttt ccaccccgta caacaacctg ctgaacgaat acgacgacct gctggctaaa    840

cacggtgaac tgctgtccga atacgacgct ctgaaagaaa aacaggacaa aaaccaggaa    900

gaaaactcca aaaacccggc tccggctccg gcttccgctg ttccggttaa aaaagaagct    960
```

```
accaaactgt ccgaagctga actgtacaac aaaatccagg aactggaaga aggtaaagct   1020

gaactgttcg acaaactgga aaaagttgaa gaagacaacc cgcgttacac cgacgctcac   1080

aacgctgtta cccagggtcg taccgttccg ctgcagaacc tgctgcacga aatggacaaa   1140

aacggtaaac tgcgttccga aaacgaagaa ctgaaagctg acctgcagaa aaaagaacag   1200

gaatag                                                              1206
```

<210> SEQ ID NO 25
<211> LENGTH: 1353
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 25

```
aacggtgacg gtaacccgcg tgaagttatc gaagacctgg ctgctaacaa cccggctatc     60

cagaacatcc gtctgcgtca cgaaaacaaa gacctgaaag ctcgtctgga aaacgctatg    120

gaagttgctg gtcgtgactt caaacgtgct ctgctggacc aggttaccca gctgtacacc    180

aaacacaact ccaactacca gcagtacaac gctcaggctg gtcgtctgga cctgcgtcag    240

aaagctgaat acctgaaagg tctgaacgac tgggctgaac gtctgctgca ggaactgaac    300

cgtgttttcc cgcgtggtac cgttgaaaac ccggacaaag ctcgtgaact gctgaacaaa    360

tacgacgttg aaaaccgtgt tttcccgcgt ggtaccgttg aaaacccgga caaagctcgt    420

gaactgctga acaaatacga cgttgaaaac tccaaaaacc cggttccggt taaaaaagaa    480

gctaaactgt ccgaagctga actgcacgac aaaatcaaaa acctgtccaa aaacccggtt    540

ccggttaaaa aagaagctaa actgtccgaa gctgaactgc acgacaaaat caaaaacctg    600

gctccgctga cccgtgctac cgctgacaac aaagacgaac tgatcaaacg tgctaacgac    660

tacgaaatcc agaaccacca gctgaccgtt gaaaacaaaa aactgaaaac cgacaaagaa    720

cagctgacca aagaaaacga cgacctgaaa gctgaatccc cgaaatccac cgaaacctcc    780

gctaacggtg ctgacaaact ggctgacgct tacaacaccc tgctgaccga acacgaaaaa    840

ctgcgtgacg aatactacac cctgatcgac gctaaagaag aagaaccgcg ttacaaagct    900

gaccactccg acctggttgc tgaaaaacag cgtctggaag acctgggtca gaaattcgaa    960

cgtctgaaac agcgttccga actgtacctg cagcagtact acgacaacaa atccaacggt   1020

tacaaaggtg actggtacgt tcagcagctg gactccgttt ccggtctgga agttgctgac   1080

ccgtccgact ccaaaaaact gatcgaactg ggtctggcta aatacctgaa cgacaaactg   1140

ccgttcaaaa ccaaagaaga ctccgaaatc ctgtccgaac tgcgtgacgt tctgaaaaac   1200

aacggtgacg gtaacccgcg tgaagttatc gaagacctgg ctgctaacaa cccggctatc   1260

cagaacatcc gtctgcgtca cgaaaacaaa gacctgaaag ctcgtctgga aaacgctatg   1320

gaagttgctg gtcgtgactt caaacgtgct tag                                1353
```

<210> SEQ ID NO 26
<211> LENGTH: 1353
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 26

```
gctgaaatca aaaaaccgca ggctgactcc gcttggaact ggccgaaaga atacaacgct     60
```

```
ctgctgaaag aaaacgaaga actgaaagtt gaacgtgaaa aatacctgtc ctacgctgac    120

gacaaagaaa aagacccgca gtaccgtgct gctgttaccc gtggtaccat caacgacccg    180

cagcgtgcta aagaagctct ggacaaatac gaactggaaa accacgctgt tacccgtggt    240

accatcaacg acccgcagcg tgctaaagaa gctctggaca aatacgaact ggaaaaccac    300

accgaagtta aagctgctgg tcagtccgct ccgaaaggta ccaacgtttc cgctgacctg    360

tacaactccc tgtgggacga aaacaaaacc ctgcgtgaaa aacaggaaga atacatcacc    420

aaaatccaga acgaagaaac caaaaacaaa gaagaagaac gtaccttcac cgaactgccg    480

tacgaagctc gttacaaagc ttggaaatcc gaaaacgacg aactgcgtga aaactaccgt    540

cgtaccctgg acaaattcaa caccgaacag ggtaaaacca cccgtctgga agaacagaac    600

cgtgttcgtt acacccgtca caccccggaa gacaaactga aaaaaatcat cgacgacctg    660

gacgctaaag aacaccgtgt tcgttacacc cgtcacaccc cggaagacaa actgaaaaaa    720

atcatcgacg acctggacgc taaagaacac cgtgtttaca tcacccgtcg tatgaccaaa    780

gaagacgttg aaaaaatcgc taacgacctg gacaccgaaa accacggtct gaaacagcag    840

aacgaacagc tgtccaccga aaaacagggt ctggaagaac agaacaaaca gctgtccacc    900

gaccgtgttt cccgttccat gtcccgtgac gacctgctga accgtgctca ggacctggaa    960

gctaaaaacc acggtctgga acaccagaac accaaactgt ccaccgaaaa caaaaccctg   1020

caggaacagg ctgaagctcg tcagaaagaa gttgctaccc gttcccagac cgacaccctg   1080

gaaaaagttc aggaacgtgc tgacaaattc gaaatcgaaa acaacaccct gaaactgaaa   1140

aactccgacc tgtccttcaa caacaaagct ctgaaagacc acaacgacga actgaccgaa   1200

gctgaaatca aaaaaccgca ggctgactcc gcttggaact ggccgaaaga atacaacgct   1260

ctgctgaaag aaaacgaaga actgaaagtt gaacgtgaaa aatacctgtc ctacgctgac   1320

gacaaagaaa aagacccgca gtaccgtgct tag                                1353
```

<210> SEQ ID NO 27
<211> LENGTH: 1353
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 27

```
gaaggtgttt ccgttggttc cgacgcttcc ctgcacaacc gtatcaccga cctggaagaa     60

gaacgtgaaa aactgctgaa caaactggac aaagttgaag aagaacacaa aaaagaccac    120

gaacagctgg aaaaaaaatc cgaagacgtt gaatcctcca acaacgctga atcctccaac    180

atctcccagg aatccaaact gatcaacacc ctgaccgacg aaaacgaaaa actgcgtgaa    240

gaactgcagc agtactacgc tctgtccgac gctaaagaag aagaaccgcg ttacaaagct    300

gacaaccagt ccccggctcc ggttaaaaaa gaagctaaaa aactgaacga agctgaactg    360

tacaacaaaa tccaggaact ggaagaaggt aaagctgaac tgttcgacaa actggaaaaa    420

gttgaagaag aaaacaaaaa agttaaagaa gactccgaca acatcaaccg ttccgtttcc    480

gttaaagaca acgaaaaaga actgcacaac aaaatcgctg acctggaaga agaacgtggt    540

gaacacctgg acaaaatcga cgaactgaaa gaagaactga aagctaaaga aaaatcctcc    600

gactcctccc gtgaagttac caacgaactg accgcttcca tgtggaaagc tcaggctgac    660

tccgctaaag ctaaagctaa agaactggaa aaacaggttg aagaatacaa aaaaaactac    720
```

```
gaaaccctgg aaaaaggtta cgacgacctg gctgaatccc gttccgtttc ccagggttcc    780

gtttccctgg aactgtacga caaactgtcc gacgaaaacg acatcctgcg tgaaaaacag    840

gacgaatacc tgaccaaaat cgacggtctg gacaaagaaa acaaagaata cgcttcccag    900

gaatcccaga actcccgttc catcaccaac gaacagctga tcgacaaact ggttgaagaa    960

aacaacgacc tgaaagaaga acgtgctaaa tacctggacc tgctggacaa ccgtgaaaaa   1020

gacccgcagt accgtgctct gatgggtgaa gctgaaaaaa aagttgaagt tgctgactcc   1080

aacgcttcct ccgttgctaa actgtacaac cagatcgctg acctgaccga caaaaacggt   1140

gaatacctgg aacgtatcga agaactggaa gaacgtcaga aaaacctgga aaaactggaa   1200

gaaggtgttt ccgttggttc cgacgcttcc ctgcacaacc gtatcaccga cctggaagaa   1260

gaacgtgaaa aactgctgaa caaactggac aaagttgaag aagaacacaa aaaagaccac   1320

gaacagctgg aaaaaaaatc cgaagacgtt tag                                1353
```

<210> SEQ ID NO 28
<211> LENGTH: 1203
<212> TYPE: DNA
<213> ORGANISM: Artificial Sequence
<220> FEATURE:
<223> OTHER INFORMATION: Polynucleotide encoding a fusion protein of group A streptococcus M proteins.

<400> SEQUENCE: 28

```
gacaacccgc gttacaccga cgctcacaac gctgttaccc agggtcgtac cgttccgctg     60

cagaacctgc tgcacgaaat ggacaaaaac ggtaaactgc gttccgaaaa cgaagaactg    120

aaagctgacc tgcagaaaaa agaacaggaa gactcctcct cccgtgacat caccgaagct    180

ggtgtttcca aattctggaa atccaaattc gacgctgaac agaaccgtgc taacgaactg    240

gaaaaaaaac tgtccggtta cgaaaaagac tacaaaaccc tggaacagga atacgaaaac    300

gctggttccg aagaaaacgt tccgaaacag cagtacaacg ctctgtggga agaaaacgaa    360

gacctgcgtg gtcgtgaacg taaatacatc gctaaactgg aaaaagaaga aatccagaac    420

ggtgaactga acgaaaaaaa ccgtaaactg gaatccccgc gtgaagttac caacgaactg    480

gctgcttccg tttggaaaaa aaaagttgaa gaagctaaag aaaaagcttc caaactggaa    540

aaacagctgg aagaagctca gaaagactac tccgaaatcg aaggtaaact ggaacagttc    600

gttgaaaaaa aagttgaagc tgctgaaaac aacgtttcct ccgttgctcg tcgtgaaaaa    660

gaactgtacg accagatcgc tgacctgacc gacaaaaacg gtgaatacct ggaacgtatc    720

ggtgaactgg aagaacgtca gaaaaacctg gacgaccgtt ccgtttccac caactccggt    780

tccgtttcca ccccgtacaa caacctgctg aacgaatacg acgacctgct ggctaaacac    840

ggtgaactgc tgtccgaata cgacgctctg aaagaaaaac aggacaaaaa ccaggaagaa    900

aactccaaaa acccggctcc ggctccggct tccgctgttc cggttaaaaa agaagctacc    960

aaactgtccg aagctgaact gtacaacaaa atccaggaac tggaagaagg taaagctgaa   1020

ctgttcgaca aactggaaaa agttgaagaa gacaacccgc gttacaccga cgctcacaac   1080

gctgttaccc agggtcgtac cgttccgctg cagaacctgc tgcacgaaat ggacaaaaac   1140

ggtaaactgc gttccgaaaa cgaagaactg aaagctgacc tgcagaaaaa agaacaggaa   1200

tag                                                                 1203
```

<210> SEQ ID NO 29
<211> LENGTH: 50
<212> TYPE: PRT
<213> ORGANISM: Streptococcus pyogenes

<400> SEQUENCE: 29

Asn Gly Asp Gly Asn Pro Arg Glu Val Ile Glu Asp Leu Ala Ala Asn
1 5 10 15

Asn Pro Ala Ile Gln Asn Ile Arg Leu Arg His Glu Asn Lys Asp Leu
20 25 30

Lys Ala Arg Leu Glu Asn Ala Met Glu Val Ala Gly Arg Asp Phe Lys
35 40 45

Arg Ala
50

<210> SEQ ID NO 30
<211> LENGTH: 50
<212> TYPE: PRT
<213> ORGANISM: Streptococcus pyogenes

<400> SEQUENCE: 30

Leu Leu Asp Gln Val Thr Gln Leu Tyr Thr Lys His Asn Ser Asn Tyr
1 5 10 15

Gln Gln Tyr Asn Ala Gln Ala Gly Arg Leu Asp Leu Arg Gln Lys Ala
20 25 30

Glu Tyr Leu Lys Gly Leu Asn Asp Trp Ala Glu Arg Leu Leu Gln Glu
35 40 45

Leu Asn
50

<210> SEQ ID NO 31
<211> LENGTH: 50
<212> TYPE: PRT
<213> ORGANISM: Streptococcus pyogenes

<400> SEQUENCE: 31

Arg Val Phe Pro Arg Gly Thr Val Glu Asn Pro Asp Lys Ala Arg Glu
1 5 10 15

Leu Leu Asn Lys Tyr Asp Val Glu Asn Arg Val Phe Pro Arg Gly Thr
20 25 30

Val Glu Asn Pro Asp Lys Ala Arg Glu Leu Leu Asn Lys Tyr Asp Val
35 40 45

Glu Asn
50

<210> SEQ ID NO 32
<211> LENGTH: 50
<212> TYPE: PRT
<213> ORGANISM: Streptococcus pyogenes

<400> SEQUENCE: 32

Ser Lys Asn Pro Val Pro Val Lys Lys Glu Ala Lys Leu Ser Glu Ala
1 5 10 15

Glu Leu His Asp Lys Ile Lys Asn Leu Ser Lys Asn Pro Val Pro Val
20 25 30

Lys Lys Glu Ala Lys Leu Ser Glu Ala Glu Leu His Asp Lys Ile Lys
35 40 45

Asn Leu
50

<210> SEQ ID NO 33
<211> LENGTH: 50
<212> TYPE: PRT
<213> ORGANISM: Streptococcus pyogenes

<400> SEQUENCE: 33

Ala Pro Leu Thr Arg Ala Thr Ala Asp Asn Lys Asp Glu Leu Ile Lys
1               5                   10                  15

Arg Ala Asn Asp Tyr Glu Ile Gln Asn His Gln Leu Thr Val Glu Asn
            20                  25                  30

Lys Lys Leu Lys Thr Asp Lys Glu Gln Leu Thr Lys Glu Asn Asp Asp
        35                  40                  45

Leu Lys
    50

<210> SEQ ID NO 34
<211> LENGTH: 50
<212> TYPE: PRT
<213> ORGANISM: Streptococcus pyogenes

<400> SEQUENCE: 34

Ala Glu Ser Pro Lys Ser Thr Glu Thr Ser Ala Asn Gly Ala Asp Lys
1               5                   10                  15

Leu Ala Asp Ala Tyr Asn Thr Leu Leu Thr Glu His Glu Lys Leu Arg
            20                  25                  30

Asp Glu Tyr Tyr Thr Leu Ile Asp Ala Lys Glu Glu Glu Pro Arg Tyr
        35                  40                  45

Lys Ala
    50

<210> SEQ ID NO 35
<211> LENGTH: 50
<212> TYPE: PRT
<213> ORGANISM: Streptococcus pyogenes

<400> SEQUENCE: 35

Asp His Ser Asp Leu Val Ala Glu Lys Gln Arg Leu Glu Asp Leu Gly
1               5                   10                  15

Gln Lys Phe Glu Arg Leu Lys Gln Arg Ser Glu Leu Tyr Leu Gln Gln
            20                  25                  30

Tyr Tyr Asp Asn Lys Ser Asn Gly Tyr Lys Gly Asp Trp Tyr Val Gln
        35                  40                  45

Gln Leu
    50

<210> SEQ ID NO 36
<211> LENGTH: 50
<212> TYPE: PRT
<213> ORGANISM: Streptococcus pyogenes

<400> SEQUENCE: 36

Asp Ser Val Ser Gly Leu Glu Val Ala Asp Pro Ser Asp Ser Lys Lys
1               5                   10                  15

Leu Ile Glu Leu Gly Leu Ala Lys Tyr Leu Asn Asp Lys Leu Pro Phe
            20                  25                  30

Lys Thr Lys Glu Asp Ser Glu Ile Leu Ser Glu Leu Arg Asp Val Leu
        35                  40                  45

Lys Asn
    50

<210> SEQ ID NO 37
<211> LENGTH: 50
<212> TYPE: PRT
<213> ORGANISM: Streptococcus pyogenes

<400> SEQUENCE: 37

```
Ala Glu Ile Lys Lys Pro Gln Ala Asp Ser Ala Trp Asn Trp Pro Lys
1               5                   10                  15

Glu Tyr Asn Ala Leu Leu Lys Glu Asn Glu Glu Leu Lys Val Glu Arg
            20                  25                  30

Glu Lys Tyr Leu Ser Tyr Ala Asp Asp Lys Glu Lys Asp Pro Gln Tyr
        35                  40                  45

Arg Ala
    50
```

<210> SEQ ID NO 38
<211> LENGTH: 50
<212> TYPE: PRT
<213> ORGANISM: Streptococcus pyogenes

<400> SEQUENCE: 38

```
Ala Val Thr Arg Gly Thr Ile Asn Asp Pro Gln Arg Ala Lys Glu Ala
1               5                   10                  15

Leu Asp Lys Tyr Glu Leu Glu Asn His Ala Val Thr Arg Gly Thr Ile
            20                  25                  30

Asn Asp Pro Gln Arg Ala Lys Glu Ala Leu Asp Lys Tyr Glu Leu Glu
        35                  40                  45

Asn His
    50
```

<210> SEQ ID NO 39
<211> LENGTH: 50
<212> TYPE: PRT
<213> ORGANISM: Streptococcus pyogenes

<400> SEQUENCE: 39

```
Thr Glu Val Lys Ala Ala Gly Gln Ser Ala Pro Lys Gly Thr Asn Val
1               5                   10                  15

Ser Ala Asp Leu Tyr Asn Ser Leu Trp Asp Glu Asn Lys Thr Leu Arg
            20                  25                  30

Glu Lys Gln Glu Glu Tyr Ile Thr Lys Ile Gln Asn Glu Glu Thr Lys
        35                  40                  45

Asn Lys
    50
```

<210> SEQ ID NO 40
<211> LENGTH: 50
<212> TYPE: PRT
<213> ORGANISM: Streptococcus pyogenes

<400> SEQUENCE: 40

```
Glu Glu Glu Arg Thr Phe Thr Glu Leu Pro Tyr Glu Ala Arg Tyr Lys
1               5                   10                  15

Ala Trp Lys Ser Glu Asn Asp Glu Leu Arg Glu Asn Tyr Arg Arg Thr
            20                  25                  30

Leu Asp Lys Phe Asn Thr Glu Gln Gly Lys Thr Thr Arg Leu Glu Glu
        35                  40                  45

Gln Asn
    50
```

<210> SEQ ID NO 41
<211> LENGTH: 50
<212> TYPE: PRT
<213> ORGANISM: Streptococcus pyogenes

<400> SEQUENCE: 41

```
Arg Val Arg Tyr Thr Arg His Thr Pro Glu Asp Lys Leu Lys Lys Ile
1               5                   10                  15

Ile Asp Asp Leu Asp Ala Lys Glu His Arg Val Arg Tyr Thr Arg His
            20                  25                  30

Thr Pro Glu Asp Lys Leu Lys Lys Ile Ile Asp Asp Leu Asp Ala Lys
        35                  40                  45

Glu His
    50
```

<210> SEQ ID NO 42
<211> LENGTH: 50
<212> TYPE: PRT
<213> ORGANISM: Streptococcus pyogenes

<400> SEQUENCE: 42

```
Arg Val Tyr Ile Thr Arg Arg Met Thr Lys Glu Asp Val Glu Lys Ile
1               5                   10                  15

Ala Asn Asp Leu Asp Thr Glu Asn His Gly Leu Lys Gln Gln Asn Glu
            20                  25                  30

Gln Leu Ser Thr Glu Lys Gln Gly Leu Glu Glu Gln Asn Lys Gln Leu
        35                  40                  45

Ser Thr
    50
```

<210> SEQ ID NO 43
<211> LENGTH: 50
<212> TYPE: PRT
<213> ORGANISM: Streptococcus pyogenes

<400> SEQUENCE: 43

```
Asp Arg Val Ser Arg Ser Met Ser Arg Asp Asp Leu Leu Asn Arg Ala
1               5                   10                  15

Gln Asp Leu Glu Ala Lys Asn His Gly Leu Glu His Gln Asn Thr Lys
            20                  25                  30

Leu Ser Thr Glu Asn Lys Thr Leu Gln Glu Gln Ala Glu Ala Arg Gln
        35                  40                  45

Lys Glu
    50
```

<210> SEQ ID NO 44
<211> LENGTH: 50
<212> TYPE: PRT
<213> ORGANISM: Streptococcus pyogenes

<400> SEQUENCE: 44

```
Val Ala Thr Arg Ser Gln Thr Asp Thr Leu Glu Lys Val Gln Glu Arg
1               5                   10                  15

Ala Asp Lys Phe Glu Ile Glu Asn Asn Thr Leu Lys Leu Lys Asn Ser
            20                  25                  30

Asp Leu Ser Phe Asn Asn Lys Ala Leu Lys Asp His Asn Asp Glu Leu
        35                  40                  45

Thr Glu
    50
```

<210> SEQ ID NO 45
<211> LENGTH: 50
<212> TYPE: PRT
<213> ORGANISM: Streptococcus pyogenes

<400> SEQUENCE: 45

Glu Gly Val Ser Val Gly Ser Asp Ala Ser Leu His Asn Arg Ile Thr
1 5 10 15

Asp Leu Glu Glu Glu Arg Glu Lys Leu Leu Asn Lys Leu Asp Lys Val
20 25 30

Glu Glu Glu His Lys Lys Asp His Glu Gln Leu Glu Lys Lys Ser Glu
35 40 45

Asp Val
50

<210> SEQ ID NO 46
<211> LENGTH: 50
<212> TYPE: PRT
<213> ORGANISM: Streptococcus pyogenes

<400> SEQUENCE: 46

Glu Ser Ser Asn Asn Ala Glu Ser Ser Asn Ile Ser Gln Glu Ser Lys
1 5 10 15

Leu Ile Asn Thr Leu Thr Asp Glu Asn Glu Lys Leu Arg Glu Glu Leu
20 25 30

Gln Gln Tyr Tyr Ala Leu Ser Asp Ala Lys Glu Glu Glu Pro Arg Tyr
35 40 45

Lys Ala
50

<210> SEQ ID NO 47
<211> LENGTH: 50
<212> TYPE: PRT
<213> ORGANISM: Streptococcus pyogenes

<400> SEQUENCE: 47

Asp Asn Gln Ser Pro Ala Pro Val Lys Lys Glu Ala Lys Lys Leu Asn
1 5 10 15

Glu Ala Glu Leu Tyr Asn Lys Ile Gln Glu Leu Glu Glu Gly Lys Ala
20 25 30

Glu Leu Phe Asp Lys Leu Glu Lys Val Glu Glu Glu Asn Lys Lys Val
35 40 45

Lys Glu
50

<210> SEQ ID NO 48
<211> LENGTH: 50
<212> TYPE: PRT
<213> ORGANISM: Streptococcus pyogenes

<400> SEQUENCE: 48

Asp Ser Asp Asn Ile Asn Arg Ser Val Ser Val Lys Asp Asn Glu Lys
1 5 10 15

Glu Leu His Asn Lys Ile Ala Asp Leu Glu Glu Glu Arg Gly Glu His
20 25 30

Leu Asp Lys Ile Asp Glu Leu Lys Glu Glu Leu Lys Ala Lys Glu Lys
35 40 45

Ser Ser
50

<210> SEQ ID NO 49
<211> LENGTH: 50
<212> TYPE: PRT
<213> ORGANISM: Streptococcus pyogenes

<400> SEQUENCE: 49

Asp Ser Ser Arg Glu Val Thr Asn Glu Leu Thr Ala Ser Met Trp Lys
1 5 10 15

Ala Gln Ala Asp Ser Ala Lys Ala Lys Ala Lys Glu Leu Glu Lys Gln
20 25 30

Val Glu Glu Tyr Lys Lys Asn Tyr Glu Thr Leu Glu Lys Gly Tyr Asp
35 40 45

Asp Leu
50

<210> SEQ ID NO 50
<211> LENGTH: 50
<212> TYPE: PRT
<213> ORGANISM: Streptococcus pyogenes

<400> SEQUENCE: 50

Ala Glu Ser Arg Ser Val Ser Gln Gly Ser Val Ser Leu Glu Leu Tyr
1 5 10 15

Asp Lys Leu Ser Asp Glu Asn Asp Ile Leu Arg Glu Lys Gln Asp Glu
20 25 30

Tyr Leu Thr Lys Ile Asp Gly Leu Asp Lys Glu Asn Lys Glu Tyr Ala
35 40 45

Ser Gln
50

<210> SEQ ID NO 51
<211> LENGTH: 50
<212> TYPE: PRT
<213> ORGANISM: Streptococcus pyogenes

<400> SEQUENCE: 51

Glu Ser Gln Asn Ser Arg Ser Ile Thr Asn Glu Gln Leu Ile Asp Lys
1 5 10 15

Leu Val Glu Glu Asn Asn Asp Leu Lys Glu Glu Arg Ala Lys Tyr Leu
20 25 30

Asp Leu Leu Asp Asn Arg Glu Lys Asp Pro Gln Tyr Arg Ala Leu Met
35 40 45

Gly Glu
50

<210> SEQ ID NO 52
<211> LENGTH: 50
<212> TYPE: PRT
<213> ORGANISM: Streptococcus pyogenes

<400> SEQUENCE: 52

Ala Glu Lys Lys Val Glu Val Ala Asp Ser Asn Ala Ser Ser Val Ala
1 5 10 15

Lys Leu Tyr Asn Gln Ile Ala Asp Leu Thr Asp Lys Asn Gly Glu Tyr
20 25 30

Leu Glu Arg Ile Glu Glu Leu Glu Glu Arg Gln Lys Asn Leu Glu Lys
35 40 45

Leu Glu
50

<210> SEQ ID NO 53
<211> LENGTH: 50
<212> TYPE: PRT
<213> ORGANISM: Streptococcus pyogenes

<400> SEQUENCE: 53

```
Asp Asn Pro Arg Tyr Thr Asp Ala His Asn Ala Val Thr Gln Gly Arg
1               5                   10                  15

Thr Val Pro Leu Gln Asn Leu Leu His Glu Met Asp Lys Asn Gly Lys
            20                  25                  30

Leu Arg Ser Glu Asn Glu Glu Leu Lys Ala Asp Leu Gln Lys Lys Glu
        35                  40                  45

Gln Glu
    50
```

<210> SEQ ID NO 54
<211> LENGTH: 50
<212> TYPE: PRT
<213> ORGANISM: Streptococcus pyogenes

<400> SEQUENCE: 54

```
Asp Ser Ser Ser Arg Asp Ile Thr Glu Ala Gly Val Ser Lys Phe Trp
1               5                   10                  15

Lys Ser Lys Phe Asp Ala Glu Gln Asn Arg Ala Asn Glu Leu Glu Lys
            20                  25                  30

Lys Leu Ser Gly Tyr Glu Lys Asp Tyr Lys Thr Leu Glu Gln Glu Tyr
        35                  40                  45

Glu Asn
    50
```

<210> SEQ ID NO 55
<211> LENGTH: 50
<212> TYPE: PRT
<213> ORGANISM: Streptococcus pyogenes

<400> SEQUENCE: 55

```
Ala Gly Ser Glu Glu Asn Val Pro Lys Gln Gln Tyr Asn Ala Leu Trp
1               5                   10                  15

Glu Glu Asn Glu Asp Leu Arg Gly Arg Glu Arg Lys Tyr Ile Ala Lys
            20                  25                  30

Leu Glu Lys Glu Glu Ile Gln Asn Gly Glu Leu Asn Glu Lys Asn Arg
        35                  40                  45

Lys Leu
    50
```

<210> SEQ ID NO 56
<211> LENGTH: 50
<212> TYPE: PRT
<213> ORGANISM: Streptococcus pyogenes

<400> SEQUENCE: 56

```
Glu Ser Pro Arg Glu Val Thr Asn Glu Leu Ala Ala Ser Val Trp Lys
1               5                   10                  15

Lys Lys Val Glu Glu Ala Lys Glu Lys Ala Ser Lys Leu Glu Lys Gln
            20                  25                  30

Leu Glu Glu Ala Gln Lys Asp Tyr Ser Glu Ile Glu Gly Lys Leu Glu
        35                  40                  45

Gln Phe
    50
```

<210> SEQ ID NO 57
<211> LENGTH: 50
<212> TYPE: PRT
<213> ORGANISM: Streptococcus pyogenes

<400> SEQUENCE: 57

```
Val Glu Lys Lys Val Glu Ala Ala Glu Asn Asn Val Ser Ser Val Ala
1               5                   10                  15

Arg Arg Glu Lys Glu Leu Tyr Asp Gln Ile Ala Asp Leu Thr Asp Lys
            20                  25                  30

Asn Gly Glu Tyr Leu Glu Arg Ile Gly Glu Leu Glu Glu Arg Gln Lys
        35                  40                  45

Asn Leu
    50
```

<210> SEQ ID NO 58
<211> LENGTH: 50
<212> TYPE: PRT
<213> ORGANISM: Streptococcus pyogenes

<400> SEQUENCE: 58

```
Asp Asp Arg Ser Val Ser Thr Asn Ser Gly Ser Val Ser Thr Pro Tyr
1               5                   10                  15

Asn Asn Leu Leu Asn Glu Tyr Asp Asp Leu Leu Ala Lys His Gly Glu
            20                  25                  30

Leu Leu Ser Glu Tyr Asp Ala Leu Lys Glu Lys Gln Asp Lys Asn Gln
        35                  40                  45

Glu Glu
    50
```

<210> SEQ ID NO 59
<211> LENGTH: 50
<212> TYPE: PRT
<213> ORGANISM: Streptococcus pyogenes

<400> SEQUENCE: 59

```
Asn Ser Lys Asn Pro Ala Pro Ala Pro Ala Ser Ala Val Pro Val Lys
1               5                   10                  15

Lys Glu Ala Thr Lys Leu Ser Glu Ala Glu Leu Tyr Asn Lys Ile Gln
            20                  25                  30

Glu Leu Glu Glu Gly Lys Ala Glu Leu Phe Asp Lys Leu Glu Lys Val
        35                  40                  45

Glu Glu
    50
```

<210> SEQ ID NO 60
<211> LENGTH: 8
<212> TYPE: PRT
<213> ORGANISM: Artificial Sequence
<220> FEATURE:
<223> OTHER INFORMATION: Epitope tag sequence

<400> SEQUENCE: 60

```
Asp Tyr Lys Asp Asp Asp Asp Lys
1               5
```

<210> SEQ ID NO 61
<211> LENGTH: 8
<212> TYPE: PRT
<213> ORGANISM: Artificial Sequence
<220> FEATURE:
<223> OTHER INFORMATION: Epitope tag sequence -continued

<400> SEQUENCE: 61

```
Asp Tyr Lys Asp Asp Asp Asp Lys
1               5
```